US008565860B2

(12) United States Patent  
Kimchy et al.

(10) Patent No.: US 8,565,860 B2  
(45) Date of Patent: Oct. 22, 2013

(54) RADIOACTIVE EMISSION DETECTOR EQUIPPED WITH A POSITION TRACKING SYSTEM

(75) Inventors: Yoav Kimchy, Haifa (IL); Roni Amrami, Yokneam (IL); Yona Bouskila, Maidenhead (GB); Udi Antebi, Kiryat Bialik (IL); Nick Sidorenko, Acre (IL); Gal Ben-David, Mitzpe Adi (IL); Yoel Zilberstein, Haifa (IL)

(73) Assignee: Biosensors International Group, Ltd., HaMilton (BM)

( * ) Notice: Subject to any disclaimer, the term of this patent is extended or adjusted under 35 U.S.C. 154(b) by 1641 days.

(21) Appl. No.: 10/616,307

(22) Filed: Jul. 10, 2003

(65) Prior Publication Data

US 2004/0054248 A1 Mar. 18, 2004

Related U.S. Application Data

(63) Continuation-in-part of application No. 10/343,792, filed as application No. PCT/IL01/00638 on Jul. 11, 2001, which is a continuation-in-part of application No. 09/727,464, filed on Dec. 4, 2000, now Pat. No. 7,826,889, which is a continuation-in-part of application No. 09/714,164, filed on Nov. 17, 2000, now abandoned, which is a continuation-in-part of application No. 09/641,973, filed on Aug. 21, 2000.

(60) Provisional application No. 60/394,936, filed on Jul. 11, 2002.

(51) Int. Cl.  
*A61B 6/00* (2006.01)

(52) U.S. Cl.  
USPC ...... 600/436; 606/130; 382/300; 250/363.02; 250/363.01

(58) Field of Classification Search  
USPC ......... 600/410, 411, 413–415, 417, 420, 424, 600/427, 431, 425, 429, 436; 606/130; 250/363.02–363.01, 559.47; 382/299, 382/300  
See application file for complete search history.

(56) References Cited

U.S. PATENT DOCUMENTS

| 630,611 A | 8/1899 | Knapp et al. |
| 2,776,377 A | 1/1957 | Anger |

(Continued)

FOREIGN PATENT DOCUMENTS

| DE | 1516429 | 12/1969 |
| DE | 19814199 | 7/1999 |

(Continued)

OTHER PUBLICATIONS

Bromiley et al. "Attenuation Correction in PET Using Consistency Conditions and a Three-Dimensional Template", IEEE Transactions on Nuclear Science, 48(4): 1371-1377, 2001. p. 1376, col. 2, § 2.

(Continued)

*Primary Examiner* — Parikha Mehta

(57) ABSTRACT

A radioactive emission probe in communication with a position tracking system and the use thereof in a variety of systems and methods of medical imaging and procedures, are provided. Specifically, wide aperture collimation—deconvolution algorithms are provided, for obtaining a high-efficiency, high resolution image of a radioactivity emitting source, by scanning the radioactivity emitting source with a probe of a wide-aperture collimator, and at the same time, monitoring the position of the radioactive emission probe, at very fine time intervals, to obtain the equivalence of fine-aperture collimation. The blurring effect of the wide aperture is then corrected mathematically. Furthermore, an imaging method by depth calculations is provided, based on the attenuation of photons of different energies, which are emitted from the same source, coupled with position monitoring.

29 Claims, 34 Drawing Sheets

(56) References Cited

U.S. PATENT DOCUMENTS

| | | |
|---|---|---|
| 3,340,866 A | 9/1967 | Nöller |
| 3,446,965 A | 5/1969 | Ogier et al. |
| 3,535,085 A | 10/1970 | Shumate et al. |
| 3,684,887 A | 8/1972 | Hugonin |
| 3,690,309 A | 9/1972 | Pluzhnikov et al. |
| 3,719,183 A | 3/1973 | Schwartz |
| 3,739,279 A | 6/1973 | Hollis |
| 3,971,362 A | 7/1976 | Pope et al. |
| 3,978,337 A | 8/1976 | Nickles et al. |
| 3,988,585 A | 10/1976 | O'Neill et al. |
| 4,000,502 A | 12/1976 | Butler et al. |
| 4,015,592 A | 4/1977 | Bradley-Moore |
| 4,055,765 A | 10/1977 | Gerber et al. |
| 4,061,919 A | 12/1977 | Miller et al. |
| 4,095,107 A | 6/1978 | Genna et al. |
| 4,165,462 A | 8/1979 | Macovski et al. |
| 4,181,856 A | 1/1980 | Bone |
| 4,278,077 A | 7/1981 | Mizumoto |
| 4,289,969 A | 9/1981 | Cooperstein et al. |
| 4,291,708 A | 9/1981 | Frei et al. |
| 4,296,785 A | 10/1981 | Vitello et al. |
| 4,302,675 A | 11/1981 | Wake et al. |
| 4,364,377 A | 12/1982 | Smith |
| 4,383,327 A | 5/1983 | Kruger |
| 4,476,381 A | 10/1984 | Rubin |
| 4,503,331 A | 3/1985 | Kovacs, Jr. et al. |
| 4,521,688 A | 6/1985 | Yin |
| H12 H | 1/1986 | Bennett et al. |
| 4,580,054 A | 4/1986 | Shimoni |
| 4,595,014 A | 6/1986 | Barrett et al. |
| 4,674,107 A | 6/1987 | Urban et al. |
| 4,679,142 A | 7/1987 | Lee |
| 4,689,041 A | 8/1987 | Corday et al. |
| 4,689,621 A | 8/1987 | Kleinberg |
| 4,709,382 A | 11/1987 | Sones |
| 4,710,624 A | 12/1987 | Alvarez et al. |
| 4,731,536 A | 3/1988 | Rische et al. |
| 4,773,430 A | 9/1988 | Porath |
| 4,782,840 A | 11/1988 | Martin, Jr. et al. |
| 4,791,934 A | 12/1988 | Brunnett |
| 4,801,803 A | 1/1989 | Denen et al. |
| 4,828,841 A | 5/1989 | Porter et al. |
| 4,834,112 A | 5/1989 | Machek et al. |
| 4,844,067 A | 7/1989 | Ikada et al. |
| 4,844,076 A | 7/1989 | Lesho et al. |
| 4,853,546 A | 8/1989 | Abe et al. |
| 4,854,324 A | 8/1989 | Hirschman et al. |
| 4,854,330 A | 8/1989 | Evans, III et al. |
| 4,893,013 A | 1/1990 | Denen et al. |
| 4,893,322 A | 1/1990 | Hellmick et al. |
| 4,919,146 A | 4/1990 | Rhinehart et al. |
| 4,924,486 A | 5/1990 | Weber et al. |
| 4,928,250 A | 5/1990 | Greenberg et al. |
| 4,929,832 A | 5/1990 | Ledley |
| 4,938,230 A | 7/1990 | Machek et al. |
| 4,951,653 A | 8/1990 | Fry et al. |
| 4,959,547 A | 9/1990 | Carroll et al. |
| 4,970,391 A | 11/1990 | Uber, III |
| 4,995,396 A | 2/1991 | Inaba et al. |
| 5,014,708 A | 5/1991 | Hayashi et al. |
| 5,018,182 A | 5/1991 | Cowan et al. |
| 5,032,729 A | 7/1991 | Charpak |
| 5,033,998 A | 7/1991 | Corday et al. |
| 5,039,863 A | 8/1991 | Matsuno et al. |
| 5,042,056 A | 8/1991 | Hellmick et al. |
| 5,070,878 A | 12/1991 | Denen |
| 5,088,492 A * | 2/1992 | Takayama et al. ............ 600/431 |
| 5,115,137 A | 5/1992 | Andersson-Engels et al. |
| 5,119,818 A | 6/1992 | Carroll et al. |
| 5,132,542 A | 7/1992 | Bassalleck et al. |
| 5,145,163 A | 9/1992 | Cowan et al. |
| 5,151,598 A | 9/1992 | Denen |
| 5,170,055 A | 12/1992 | Carroll et al. |
| 5,170,439 A | 12/1992 | Zeng et al. |
| 5,170,789 A | 12/1992 | Narayan et al. |
| 5,196,796 A | 3/1993 | Misic et al. |
| 5,210,421 A | 5/1993 | Gullberg et al. |
| 5,243,988 A | 9/1993 | Sieben et al. |
| 5,246,005 A | 9/1993 | Carroll et al. |
| 5,249,124 A | 9/1993 | DeVito |
| 5,252,830 A | 10/1993 | Weinberg |
| 5,254,101 A | 10/1993 | Trombley, III |
| 5,258,717 A | 11/1993 | Misic et al. |
| 5,263,077 A | 11/1993 | Cowan et al. |
| 5,279,607 A | 1/1994 | Schentag et al. |
| 5,284,147 A | 2/1994 | Hanaoka et al. |
| 5,299,253 A | 3/1994 | Wessels |
| 5,304,165 A | 4/1994 | Haber et al. |
| 5,307,808 A | 5/1994 | Dumoulin et al. |
| 5,307,814 A | 5/1994 | Kressel et al. |
| 5,309,959 A | 5/1994 | Shaw et al. |
| 5,317,506 A | 5/1994 | Coutre et al. |
| 5,317,619 A | 5/1994 | Hellmick et al. |
| 5,323,006 A | 6/1994 | Thompson et al. |
| 5,329,976 A | 7/1994 | Haber et al. |
| 5,334,141 A | 8/1994 | Carr et al. |
| 5,349,190 A | 9/1994 | Hines et al. |
| 5,355,087 A | 10/1994 | Claiborne et al. |
| 5,365,069 A | 11/1994 | Eisen et al. |
| 5,365,928 A | 11/1994 | Rhinehart et al. |
| 5,367,552 A | 11/1994 | Peschmann |
| 5,377,681 A | 1/1995 | Drane |
| 5,381,791 A | 1/1995 | Qian |
| 5,383,456 A | 1/1995 | Arnold et al. |
| 5,383,858 A | 1/1995 | Reilly et al. |
| 5,386,446 A | 1/1995 | Fujimoto et al. |
| 5,387,409 A | 2/1995 | Nunn et al. |
| 5,391,877 A | 2/1995 | Marks |
| 5,395,366 A | 3/1995 | D'Andrea et al. |
| 5,399,868 A | 3/1995 | Jones et al. |
| 5,404,293 A | 4/1995 | Weng et al. |
| 5,415,181 A | 5/1995 | Hogrefe et al. |
| 5,431,161 A | 7/1995 | Ryals et al. |
| 5,435,302 A | 7/1995 | Lenkinski et al. |
| 5,436,458 A | 7/1995 | Tran et al. |
| 5,441,050 A | 8/1995 | Thurston et al. |
| 5,448,073 A | 9/1995 | Jeanguillaume |
| 5,451,232 A | 9/1995 | Rhinehart et al. |
| 5,472,403 A | 12/1995 | Cornacchia et al. |
| 5,475,219 A | 12/1995 | Olson |
| 5,475,232 A | 12/1995 | Powers et al. |
| 5,476,095 A | 12/1995 | Schnall et al. |
| 5,479,969 A | 1/1996 | Hardie et al. |
| 5,481,115 A | 1/1996 | Hsieh et al. |
| 5,484,384 A | 1/1996 | Fearnot |
| 5,489,782 A | 2/1996 | Wernikoff |
| 5,493,595 A | 2/1996 | Schoolman |
| 5,493,805 A | 2/1996 | Penuela et al. |
| 5,494,036 A | 2/1996 | Uber, III et al. |
| 5,501,674 A | 3/1996 | Trombley, III et al. |
| 5,517,120 A | 5/1996 | Misic et al. |
| 5,519,221 A | 5/1996 | Weinberg |
| 5,519,222 A | 5/1996 | Besett |
| 5,519,931 A | 5/1996 | Reich |
| 5,520,182 A | 5/1996 | Leighton et al. |
| 5,520,653 A | 5/1996 | Reilly et al. |
| 5,521,506 A | 5/1996 | Misic et al. |
| 5,536,945 A | 7/1996 | Reich |
| 5,545,899 A | 8/1996 | Tran et al. |
| 5,559,335 A | 9/1996 | Zeng et al. |
| 5,565,684 A | 10/1996 | Gullberg et al. |
| 5,569,181 A | 10/1996 | Heilman et al. |
| 5,572,132 A | 11/1996 | Pulyer et al. |
| 5,572,999 A | 11/1996 | Funda et al. |
| 5,579,766 A | 12/1996 | Gray |
| 5,580,541 A | 12/1996 | Wells et al. |
| 5,585,637 A | 12/1996 | Bertelsen et al. |
| 5,587,585 A | 12/1996 | Eisen et al. |
| 5,591,143 A | 1/1997 | Trombley, III et al. |
| 5,600,145 A | 2/1997 | Plummer |
| 5,604,531 A | 2/1997 | Iddan et al. |
| 5,610,520 A | 3/1997 | Misic |
| 5,617,858 A | 4/1997 | Taverna et al. |
| 5,629,524 A | 5/1997 | Stettner et al. |

| | | | | | | |
|---|---|---|---|---|---|---|
| 5,635,717 A | 6/1997 | Popescu | | 5,997,502 A | 12/1999 | Reilly et al. |
| 5,657,759 A | 8/1997 | Essen-Moller | | 6,002,134 A | 12/1999 | Lingren |
| 5,672,877 A | 9/1997 | Liebig et al. | | 6,002,480 A | 12/1999 | Izatt et al. |
| 5,677,539 A | 10/1997 | Apotovsky et al. | | 6,017,330 A | 1/2000 | Hitchins et al. |
| 5,682,888 A | 11/1997 | Olson et al. | | 6,019,745 A | 2/2000 | Gray |
| 5,687,542 A | 11/1997 | Lawecki et al. | | 6,021,341 A | 2/2000 | Scibilia et al. |
| 5,690,691 A | 11/1997 | Chen et al. | | 6,037,595 A | 3/2000 | Lingren |
| 5,692,640 A | 12/1997 | Caulfield et al. | | 6,040,697 A | 3/2000 | Misic |
| 5,694,933 A | 12/1997 | Madden et al. | | 6,042,565 A | 3/2000 | Hirschman et al. |
| 5,695,500 A | 12/1997 | Taylor et al. | | RE36,648 E | 4/2000 | Uber, III et al. |
| 5,716,595 A | 2/1998 | Goldenberg | | 6,046,454 A | 4/2000 | Lingren et al. |
| 5,727,554 A | 3/1998 | Kalend et al. | | 6,048,334 A | 4/2000 | Hirschman et al. |
| 5,729,129 A | 3/1998 | Acker | | 6,052,618 A | 4/2000 | Dahlke et al. |
| 5,732,704 A | 3/1998 | Thurston et al. | | 6,055,450 A | 4/2000 | Ashburn |
| 5,739,508 A | 4/1998 | Uber, III | | 6,055,452 A | 4/2000 | Pearlman |
| 5,741,232 A | 4/1998 | Reilly et al. | | RE36,693 E | 5/2000 | Reich |
| 5,742,060 A | 4/1998 | Ashburn | | 6,063,052 A | 5/2000 | Uber et al. |
| 5,744,805 A | 4/1998 | Raylman et al. | | D426,891 S | 6/2000 | Beale et al. |
| 5,757,006 A | 5/1998 | De Vito et al. | | D426,892 S | 6/2000 | Beale et al. |
| 5,779,675 A | 7/1998 | Reilly et al. | | 6,072,177 A | 6/2000 | McCroskey et al. |
| 5,780,855 A | 7/1998 | Pare et al. | | 6,076,009 A | 6/2000 | Raylman et al. |
| 5,781,442 A | 7/1998 | Engleson et al. | | 6,080,984 A | 6/2000 | Friesenhahn |
| 5,784,432 A | 7/1998 | Kurtz et al. | | D428,491 S | 7/2000 | Beale et al. |
| 5,786,597 A | 7/1998 | Lingren et al. | | 6,082,366 A | 7/2000 | Andra et al. |
| 5,795,333 A | 8/1998 | Reilly et al. | | 6,090,064 A | 7/2000 | Reilly et al. |
| 5,800,355 A | 9/1998 | Hasegawa | | 6,091,070 A | 7/2000 | Lingren et al. |
| 5,803,914 A | 9/1998 | Ryals et al. | | 6,096,011 A | 8/2000 | Trombley, III et al. |
| 5,806,519 A | 9/1998 | Evans, III et al. | | 6,107,102 A | 8/2000 | Ferrari |
| 5,808,203 A | 9/1998 | Nolan, Jr. et al. | | 6,115,635 A | 9/2000 | Bourgeois |
| 5,810,742 A | 9/1998 | Pearlman | | 6,129,670 A | 10/2000 | Burdette et al. |
| 5,811,814 A | 9/1998 | Leone et al. | | 6,132,372 A | 10/2000 | Essen-Moller |
| 5,813,985 A | 9/1998 | Carroll | | 6,135,955 A | 10/2000 | Madden et al. |
| 5,818,050 A | 10/1998 | Dilmanian et al. | | 6,135,968 A | 10/2000 | Brounstein |
| 5,821,541 A | 10/1998 | Tümer | | 6,137,109 A | 10/2000 | Hayes |
| 5,825,031 A | 10/1998 | Wong et al. | | 6,145,277 A | 11/2000 | Lawecki et al. |
| 5,827,219 A | 10/1998 | Uber, III et al. | | 6,147,352 A | 11/2000 | Ashburn |
| 5,828,073 A | 10/1998 | Zhu et al. | | 6,147,353 A | 11/2000 | Gagnon et al. |
| 5,833,603 A | 11/1998 | Kovacs et al. | | 6,148,229 A | 11/2000 | Morris, Sr. et al. |
| 5,838,009 A | 11/1998 | Plummer et al. | | 6,149,627 A | 11/2000 | Uber, III |
| 5,840,026 A | 11/1998 | Uber, III et al. | | 6,155,485 A | 12/2000 | Coughlin et al. |
| 5,841,141 A | 11/1998 | Gullberg et al. | | 6,160,398 A | 12/2000 | Walsh |
| 5,842,977 A | 12/1998 | Lesho et al. | | 6,162,198 A | 12/2000 | Coffey et al. |
| 5,843,037 A | 12/1998 | Uber, III | | 6,172,362 B1 | 1/2001 | Lingren et al. |
| 5,846,513 A | 12/1998 | Carroll et al. | | 6,173,201 B1 | 1/2001 | Front |
| 5,847,396 A | 12/1998 | Lingren et al. | | 6,184,530 B1 | 2/2001 | Hines et al. |
| 5,857,463 A | 1/1999 | Thurston et al. | | 6,189,195 B1 | 2/2001 | Reilly et al. |
| 5,871,013 A | 2/1999 | Wainer et al. | | 6,194,715 B1 | 2/2001 | Lingren et al. |
| 5,873,861 A | 2/1999 | Hitchins et al. | | 6,194,725 B1 | 2/2001 | Colsher et al. |
| 5,880,475 A | 3/1999 | Oka et al. | | 6,194,726 B1 | 2/2001 | Pi et al. |
| 5,882,338 A | 3/1999 | Gray | | 6,197,000 B1 | 3/2001 | Reilly et al. |
| 5,884,457 A | 3/1999 | Ortiz et al. | | 6,202,923 B1 | 3/2001 | Boyer et al. |
| 5,885,216 A | 3/1999 | Evans, III et al. | | 6,205,347 B1 | 3/2001 | Morgan et al. |
| 5,893,397 A | 4/1999 | Peterson et al. | | 6,212,423 B1 * | 4/2001 | Krakovitz .................. 600/473 |
| 5,899,885 A | 5/1999 | Reilly et al. | | 6,223,065 B1 | 4/2001 | Misic et al. |
| 5,900,533 A | 5/1999 | Chou | | 6,224,577 B1 | 5/2001 | Dedola et al. |
| 5,903,008 A | 5/1999 | Li | | 6,226,350 B1 | 5/2001 | Hsieh |
| 5,910,112 A | 6/1999 | Judd et al. | | 6,229,145 B1 | 5/2001 | Weinberg |
| 5,911,252 A | 6/1999 | Cassel | | 6,232,605 B1 | 5/2001 | Soluri et al. |
| 5,916,167 A | 6/1999 | Kramer et al. | | 6,233,304 B1 | 5/2001 | Hu et al. |
| 5,916,197 A | 6/1999 | Reilly et al. | | 6,236,050 B1 | 5/2001 | Tumer |
| 5,920,054 A | 7/1999 | Uber, III | | 6,236,878 B1 | 5/2001 | Taylor et al. |
| 5,927,351 A | 7/1999 | Zhu et al. | | 6,236,880 B1 | 5/2001 | Raylman et al. |
| 5,928,150 A | 7/1999 | Call | | 6,239,438 B1 | 5/2001 | Schubert |
| 5,932,879 A | 8/1999 | Raylman et al. | | 6,240,312 B1 | 5/2001 | Alfano et al. |
| 5,938,639 A | 8/1999 | Reilly et al. | | 6,241,708 B1 | 6/2001 | Reilly et al. |
| 5,939,724 A | 8/1999 | Eisen et al. | | 6,242,743 B1 | 6/2001 | DeVito et al. |
| 5,944,190 A | 8/1999 | Edelen | | 6,242,744 B1 | 6/2001 | Soluri et al. |
| 5,944,694 A | 8/1999 | Hitchins et al. | | 6,242,745 B1 | 6/2001 | Berlad et al. |
| 5,947,935 A | 9/1999 | Rhinehart et al. | | 6,246,901 B1 | 6/2001 | Benaron |
| 5,953,884 A | 9/1999 | Lawecki et al. | | 6,252,924 B1 | 6/2001 | Davantes et al. |
| 5,954,668 A | 9/1999 | Uber, III et al. | | 6,258,576 B1 | 7/2001 | Richards-Kortum et al. |
| 5,961,457 A | 10/1999 | Raylman et al. | | 6,259,095 B1 | 7/2001 | Bouton et al. |
| 5,967,983 A | 10/1999 | Ashburn | | 6,261,562 B1 | 7/2001 | Xu et al. |
| 5,973,598 A | 10/1999 | Beigel | | 6,263,229 B1 | 7/2001 | Atalar et al. |
| 5,974,165 A | 10/1999 | Giger et al. | | 6,269,340 B1 | 7/2001 | Ford et al. |
| 5,984,860 A | 11/1999 | Shan | | 6,270,463 B1 | 8/2001 | Morris, Sr. et al. |
| 5,987,350 A | 11/1999 | Thurston | | 6,271,524 B1 | 8/2001 | Wainer et al. |
| 5,993,378 A | 11/1999 | Lemelson | | 6,271,525 B1 | 8/2001 | Majewski et al. |
| | | | | 6,280,704 B1 | 8/2001 | Schutt et al. |

| | | |
|---|---|---|
| 6,281,505 B1 | 8/2001 | Hines et al. |
| 6,308,097 B1 | 10/2001 | Pearlman |
| 6,310,968 B1 | 10/2001 | Hawkins et al. |
| 6,315,981 B1 | 11/2001 | Unger |
| 6,317,623 B1 | 11/2001 | Griffiths et al. |
| 6,317,648 B1 | 11/2001 | Sleep et al. |
| 6,318,630 B1 | 11/2001 | Coughlin et al. |
| 6,322,535 B1 | 11/2001 | Hitchins et al. |
| 6,323,648 B1 | 11/2001 | Belt et al. |
| 6,324,418 B1 | 11/2001 | Crowley et al. |
| RE37,487 E | 12/2001 | Reilly et al. |
| D452,737 S | 1/2002 | Nolan, Jr. et al. |
| 6,336,913 B1 | 1/2002 | Spohn et al. |
| 6,339,652 B1 | 1/2002 | Hawkins et al. |
| 6,339,718 B1 | 1/2002 | Zatezalo et al. |
| 6,344,745 B1 | 2/2002 | Reisker et al. |
| 6,346,706 B1 | 2/2002 | Rogers et al. |
| 6,346,886 B1 | 2/2002 | de la Huerga |
| RE37,602 E | 3/2002 | Uber, III et al. |
| 6,353,227 B1 | 3/2002 | Boxen |
| 6,356,081 B1 | 3/2002 | Misic |
| 6,368,331 B1 | 4/2002 | Front et al. |
| 6,371,938 B1 | 4/2002 | Reilly et al. |
| 6,375,624 B1 | 4/2002 | Uber, III et al. |
| 6,377,838 B1 | 4/2002 | Iwanczyk et al. |
| 6,381,349 B1 | 4/2002 | Zeng et al. |
| 6,385,483 B1 | 5/2002 | Uber, III et al. |
| 6,388,244 B1 | 5/2002 | Gagnon |
| 6,388,258 B1 | 5/2002 | Berlad et al. |
| 6,392,235 B1 | 5/2002 | Barrett et al. |
| 6,396,273 B2 | 5/2002 | Misic |
| 6,397,098 B1 | 5/2002 | Uber, III et al. |
| 6,399,951 B1 | 6/2002 | Paulus et al. |
| 6,402,717 B1 | 6/2002 | Reilly et al. |
| 6,402,718 B1 | 6/2002 | Reilly et al. |
| 6,407,391 B1 | 6/2002 | Mastrippolito et al. |
| 6,408,204 B1 | 6/2002 | Hirschman |
| 6,409,987 B1 | 6/2002 | Cardin et al. |
| 6,420,711 B2 | 7/2002 | Tuemer |
| 6,425,174 B1 | 7/2002 | Reich |
| 6,426,917 B1 | 7/2002 | Tabanou et al. |
| 6,429,431 B1 | 8/2002 | Wilk |
| 6,431,175 B1 | 8/2002 | Penner et al. |
| 6,432,089 B1 | 8/2002 | Kakimi et al. |
| 6,438,401 B1 | 8/2002 | Cheng et al. |
| 6,439,444 B1 | 8/2002 | Shields, II |
| 6,440,107 B1 | 8/2002 | Trombley, III et al. |
| 6,442,418 B1 | 8/2002 | Evans, III et al. |
| 6,448,560 B1 | 9/2002 | Tumer |
| 6,453,199 B1 | 9/2002 | Kobozev |
| 6,459,925 B1 | 10/2002 | Nields et al. |
| 6,459,931 B1 | 10/2002 | Hirschman |
| 6,468,261 B1 | 10/2002 | Small et al. |
| 6,469,306 B1 | 10/2002 | Van Dulmen et al. |
| 6,471,674 B1 | 10/2002 | Emig et al. |
| 6,480,732 B1 | 11/2002 | Tanaka et al. |
| 6,484,051 B1 | 11/2002 | Daniel |
| 6,488,661 B1 | 12/2002 | Spohn et al. |
| 6,490,476 B1 | 12/2002 | Townsend et al. |
| 6,504,157 B2 | 1/2003 | Juhi |
| 6,504,178 B2 | 1/2003 | Carlson et al. |
| 6,504,899 B2 | 1/2003 | Pugachev et al. |
| 6,506,155 B2 | 1/2003 | Sluis et al. |
| 6,510,336 B1 * | 1/2003 | Daghighian et al. .......... 600/427 |
| 6,512,374 B1 | 1/2003 | Misic et al. |
| 6,516,213 B1 | 2/2003 | Nevo |
| 6,519,569 B1 | 2/2003 | White et al. |
| 6,520,930 B2 | 2/2003 | Critchlow et al. |
| 6,522,945 B2 | 2/2003 | Sleep et al. |
| 6,525,320 B1 | 2/2003 | Juni |
| 6,525,321 B1 | 2/2003 | Juni |
| 6,541,763 B2 | 4/2003 | Lingren et al. |
| 6,545,280 B2 | 4/2003 | Weinberg et al. |
| 6,549,646 B1 | 4/2003 | Yeh et al. |
| 6,560,354 B1 | 5/2003 | Maurer, Jr. et al. |
| 6,562,008 B1 | 5/2003 | Reilly et al. |
| 6,563,942 B2 | 5/2003 | Takeo et al. |
| 6,565,502 B1 | 5/2003 | Bede et al. |
| 6,567,687 B2 | 5/2003 | Front et al. |
| 6,575,930 B1 | 6/2003 | Trombley, III et al. |
| 6,576,918 B1 | 6/2003 | Fu et al. |
| 6,584,348 B2 | 6/2003 | Glukhovsky |
| 6,585,700 B1 | 7/2003 | Trocki et al. |
| 6,587,710 B1 | 7/2003 | Wainer |
| 6,589,158 B2 | 7/2003 | Winkler |
| 6,591,127 B1 | 7/2003 | McKinnon |
| 6,592,520 B1 | 7/2003 | Peszynski et al. |
| 6,602,488 B1 | 8/2003 | Daghighian |
| 6,607,301 B1 | 8/2003 | Glukhovsky et al. |
| 6,611,141 B1 | 8/2003 | Schulz et al. |
| 6,614,453 B1 | 9/2003 | Suri et al. |
| 6,620,134 B1 | 9/2003 | Trombley, III et al. |
| 6,627,893 B1 | 9/2003 | Zeng et al. |
| 6,628,983 B1 | 9/2003 | Gagnon |
| 6,628,984 B2 | 9/2003 | Weinberg |
| 6,630,735 B1 | 10/2003 | Carlson et al. |
| 6,631,284 B2 | 10/2003 | Nutt et al. |
| 6,632,216 B2 | 10/2003 | Houzego et al. |
| 6,638,752 B2 | 10/2003 | Contag et al. |
| 6,643,537 B1 | 11/2003 | Zatezalo et al. |
| 6,643,538 B1 | 11/2003 | Majewski et al. |
| 6,652,489 B2 | 11/2003 | Trocki et al. |
| 6,657,200 B2 | 12/2003 | Nygard et al. |
| 6,662,036 B2 | 12/2003 | Cosman |
| 6,664,542 B2 | 12/2003 | Ye et al. |
| 6,670,258 B2 | 12/2003 | Carlson et al. |
| 6,671,563 B1 | 12/2003 | Engelson et al. |
| 6,673,033 B1 | 1/2004 | Sciulli et al. |
| 6,674,834 B1 | 1/2004 | Acharya et al. |
| 6,676,634 B1 | 1/2004 | Spohn et al. |
| 6,677,182 B2 | 1/2004 | Carlson et al. |
| 6,677,755 B2 | 1/2004 | Belt et al. |
| 6,680,750 B1 * | 1/2004 | Tournier et al. ................ 348/294 |
| 6,694,172 B1 | 2/2004 | Gagnon et al. |
| 6,699,219 B2 | 3/2004 | Emig et al. |
| 6,704,592 B1 | 3/2004 | Reynolds et al. |
| 6,713,766 B2 | 3/2004 | Garrard et al. |
| 6,714,012 B2 | 3/2004 | Belt et al. |
| 6,714,013 B2 | 3/2004 | Misic |
| 6,716,195 B2 | 4/2004 | Nolan, Jr. et al. |
| 6,722,499 B2 | 4/2004 | Reich |
| 6,723,988 B1 | 4/2004 | Wainer |
| 6,726,657 B1 | 4/2004 | Dedig et al. |
| 6,728,583 B2 | 4/2004 | Hallett |
| 6,731,971 B2 | 5/2004 | Evans, III et al. |
| 6,731,989 B2 | 5/2004 | Engleson et al. |
| 6,733,477 B2 | 5/2004 | Cowan et al. |
| 6,733,478 B2 | 5/2004 | Reilly et al. |
| 6,734,416 B2 | 5/2004 | Carlson et al. |
| 6,734,430 B2 | 5/2004 | Soluri et al. |
| 6,737,652 B2 | 5/2004 | Lanza et al. |
| 6,737,866 B2 | 5/2004 | Belt et al. |
| 6,740,882 B2 | 5/2004 | Weinberg et al. |
| 6,743,202 B2 | 6/2004 | Hirschman et al. |
| 6,743,205 B2 | 6/2004 | Nolan, Jr. et al. |
| 6,747,454 B2 | 6/2004 | Belt |
| 6,748,259 B1 | 6/2004 | Benaron et al. |
| 6,751,500 B2 | 6/2004 | Hirschman et al. |
| 6,765,981 B2 | 7/2004 | Heumann |
| 6,766,048 B1 * | 7/2004 | Launay et al. ................ 382/154 |
| 6,771,802 B1 | 8/2004 | Patt et al. |
| 6,774,358 B2 | 8/2004 | Hamill et al. |
| 6,776,977 B2 | 8/2004 | Liu |
| 6,787,777 B1 | 9/2004 | Gagnon et al. |
| 6,788,758 B2 | 9/2004 | De Villiers |
| 6,798,206 B2 | 9/2004 | Misic |
| 6,808,513 B2 | 10/2004 | Reilly et al. |
| 6,813,868 B2 | 11/2004 | Baldwin et al. |
| 6,821,013 B2 | 11/2004 | Reilly et al. |
| 6,822,237 B2 | 11/2004 | Inoue et al. |
| 6,833,705 B2 | 12/2004 | Misic |
| 6,838,672 B2 | 1/2005 | Wagenaar et al. |
| 6,841,782 B1 | 1/2005 | Balan et al. |
| 6,843,357 B2 | 1/2005 | Bybee et al. |
| 6,851,615 B2 | 2/2005 | Jones |
| 6,866,654 B2 | 3/2005 | Callan et al. |
| 6,870,175 B2 | 3/2005 | Dell et al. |

| | | | |
|---|---|---|---|
| 6,881,043 B2 | 4/2005 | Barak | |
| 6,888,351 B2 | 5/2005 | Belt et al. | |
| 6,889,074 B2 | 5/2005 | Uber, III et al. | |
| 6,897,658 B2 | 5/2005 | Belt et al. | |
| 6,906,330 B2 | 6/2005 | Blevis et al. | |
| D507,832 S | 7/2005 | Yanniello et al. | |
| 6,915,170 B2 | 7/2005 | Engleson et al. | |
| 6,915,823 B2 | 7/2005 | Osborne et al. | |
| 6,917,828 B2 | 7/2005 | Fukuda | |
| 6,921,384 B2 | 7/2005 | Reilly et al. | |
| 6,935,560 B2 | 8/2005 | Andreasson et al. | |
| 6,936,030 B1 | 8/2005 | Pavlik et al. | |
| 6,937,750 B2 | 8/2005 | Natanzon et al. | |
| 6,939,302 B2 | 9/2005 | Griffiths et al. | |
| 6,940,070 B2 | 9/2005 | Tumer | |
| 6,943,355 B2 | 9/2005 | Shwartz et al. | |
| 6,957,522 B2 | 10/2005 | Baldwin et al. | |
| 6,958,053 B1 | 10/2005 | Reilly | |
| 6,963,770 B2 | 11/2005 | Scarantino et al. | |
| 6,970,735 B2 | 11/2005 | Uber, III et al. | |
| 6,972,001 B2 | 12/2005 | Emig et al. | |
| 6,974,443 B2 | 12/2005 | Reilly et al. | |
| 6,976,349 B2 | 12/2005 | Baldwin et al. | |
| 6,984,222 B1 | 1/2006 | Hitchins et al. | |
| 6,985,870 B2 | 1/2006 | Martucci et al. | |
| 6,988,981 B2 | 1/2006 | Hamazaki | |
| 6,994,249 B2 | 2/2006 | Peterka et al. | |
| 7,009,183 B2 | 3/2006 | Wainer et al. | |
| 7,011,814 B2 | 3/2006 | Suddarth et al. | |
| 7,012,430 B2 | 3/2006 | Misic | |
| 7,017,622 B2 | 3/2006 | Osborne et al. | |
| 7,018,363 B2 | 3/2006 | Cowan et al. | |
| 7,019,783 B2 | 3/2006 | Kindem et al. | |
| 7,025,757 B2 | 4/2006 | Reilly et al. | |
| 7,026,623 B2 | 4/2006 | Oaknin et al. | |
| 7,043,063 B1 | 5/2006 | Noble et al. | |
| 7,102,138 B2 | 9/2006 | Belvis et al. | |
| 7,103,204 B1 | 9/2006 | Celler et al. | |
| 7,127,026 B2 | 10/2006 | Amemiya et al. | |
| 7,142,634 B2 | 11/2006 | Engler et al. | |
| 7,145,986 B2 | 12/2006 | Wear et al. | |
| 7,147,372 B2 | 12/2006 | Nelson et al. | |
| 7,164,130 B2 | 1/2007 | Welsh et al. | |
| 7,176,466 B2 | 2/2007 | Rousso et al. | |
| 7,187,790 B2 | 3/2007 | Sabol et al. | |
| 7,217,953 B2 | 5/2007 | Carlson | |
| 7,256,386 B2 | 8/2007 | Carlson et al. | |
| 7,327,822 B2 | 2/2008 | Sauer et al. | |
| 7,359,535 B2 | 4/2008 | Salla et al. | |
| 7,373,197 B2 | 5/2008 | Daighighian et al. | |
| 7,394,923 B2 | 7/2008 | Zou et al. | |
| 7,444,010 B2 | 10/2008 | De Man | |
| 7,468,513 B2 | 12/2008 | Charron et al. | |
| 7,470,896 B2 | 12/2008 | Pawlak et al. | |
| 7,490,085 B2 | 2/2009 | Walker et al. | |
| 7,495,225 B2 | 2/2009 | Hefetz et al. | |
| 7,502,499 B2 | 3/2009 | Grady | |
| 7,570,732 B2 | 8/2009 | Stanton et al. | |
| 7,592,597 B2 | 9/2009 | Hefetz et al. | |
| 7,620,444 B2 | 11/2009 | Le et al. | |
| 7,627,084 B2 | 12/2009 | Jabri et al. | |
| 7,652,259 B2 | 1/2010 | Kimchy et al. | |
| 7,671,331 B2 | 3/2010 | Hefetz | |
| 7,672,491 B2 | 3/2010 | Krishnan et al. | |
| 7,680,240 B2 | 3/2010 | Manjeshwar et al. | |
| 7,705,316 B2 | 4/2010 | Rousso et al. | |
| 7,734,331 B2 | 6/2010 | Dhawale et al. | |
| 7,826,889 B2 | 11/2010 | David et al. | |
| 7,831,024 B2 | 11/2010 | Metzler et al. | |
| 7,835,927 B2 | 11/2010 | Schlotterbeck et al. | |
| 7,872,235 B2 | 1/2011 | Rousso et al. | |
| 7,894,650 B2 | 2/2011 | Weng et al. | |
| 7,968,851 B2 | 6/2011 | Rousso et al. | |
| 8,013,308 B2 | 9/2011 | Guerin et al. | |
| 8,055,329 B2 | 11/2011 | Kimchy et al. | |
| 8,111,886 B2 | 2/2012 | Rousso et al. | |
| 8,158,951 B2 | 4/2012 | Bal et al. | |
| 8,204,500 B2 | 6/2012 | Weintraub et al. | |
| 8,338,788 B2 | 12/2012 | Zilberstein et al. | |
| 2001/0016029 A1 | 8/2001 | Tumer | |
| 2001/0020131 A1 | 9/2001 | Kawagishi et al. | |
| 2001/0035902 A1 | 11/2001 | Iddan et al. | |
| 2001/0049608 A1 | 12/2001 | Hochman | |
| 2002/0072784 A1 | 6/2002 | Sheppard et al. | |
| 2002/0085748 A1 | 7/2002 | Baumberg | |
| 2002/0087101 A1 | 7/2002 | Barrick et al. | |
| 2002/0099295 A1 | 7/2002 | Gil et al. | |
| 2002/0099310 A1 | 7/2002 | Kimchy et al. | |
| 2002/0099334 A1 | 7/2002 | Hanson et al. | |
| 2002/0103429 A1 | 8/2002 | DeCharms | |
| 2002/0103431 A1 | 8/2002 | Toker et al. | |
| 2002/0145114 A1 | 10/2002 | Inoue et al. | |
| 2002/0148970 A1 | 10/2002 | Wong et al. | |
| 2002/0165491 A1 | 11/2002 | Reilly | |
| 2002/0168094 A1 | 11/2002 | Kaushikkar et al. | |
| 2002/0168317 A1 | 11/2002 | Daighighian et al. | |
| 2002/0172405 A1 | 11/2002 | Schultz | |
| 2002/0179843 A1 | 12/2002 | Tanaka et al. | |
| 2002/0183645 A1 | 12/2002 | Nachaliel | |
| 2002/0188197 A1 | 12/2002 | Bishop et al. | |
| 2002/0198738 A1 | 12/2002 | Osborne | |
| 2003/0001098 A1 | 1/2003 | Stoddart et al. | |
| 2003/0001837 A1 | 1/2003 | Baumberg | |
| 2003/0006376 A1 | 1/2003 | Tumer | |
| 2003/0013950 A1 | 1/2003 | Rollo et al. | |
| 2003/0013966 A1 | 1/2003 | Barnes et al. | |
| 2003/0038240 A1 | 2/2003 | Weinberg | |
| 2003/0055685 A1 | 3/2003 | Cobb et al. | |
| 2003/0063787 A1 | 4/2003 | Natanzon et al. | |
| 2003/0071219 A1 | 4/2003 | Motomura et al. | |
| 2003/0081716 A1 | 5/2003 | Tumer | |
| 2003/0135388 A1 | 7/2003 | Martucci et al. | |
| 2003/0136912 A1 | 7/2003 | Juni | |
| 2003/0144322 A1 | 7/2003 | Kozikowski et al. | |
| 2003/0158481 A1 | 8/2003 | Stotzka et al. | |
| 2003/0183226 A1 | 10/2003 | Brand et al. | |
| 2003/0189174 A1 | 10/2003 | Tanaka et al. | |
| 2003/0191430 A1 | 10/2003 | D'Andrea et al. | |
| 2003/0202629 A1 | 10/2003 | Dunham et al. | |
| 2003/0208117 A1 | 11/2003 | Shwartz et al. | |
| 2003/0215122 A1 | 11/2003 | Tanaka | |
| 2003/0215124 A1 | 11/2003 | Li | |
| 2003/0219149 A1 | 11/2003 | Vailaya et al. | |
| 2004/0003001 A1 | 1/2004 | Shimura | |
| 2004/0010397 A1 | 1/2004 | Barbour et al. | |
| 2004/0015075 A1 | 1/2004 | Kimchy et al. | |
| 2004/0021065 A1 | 2/2004 | Weber | |
| 2004/0044282 A1 | 3/2004 | Mixon et al. | |
| 2004/0051368 A1 | 3/2004 | Caputo et al. | |
| 2004/0054278 A1 | 3/2004 | Kimchy et al. | |
| 2004/0065838 A1 | 4/2004 | Tumer | |
| 2004/0075058 A1 | 4/2004 | Blevis et al. | |
| 2004/0081623 A1 | 4/2004 | Eriksen et al. | |
| 2004/0082918 A1 | 4/2004 | Evans et al. | |
| 2004/0084340 A1 | 5/2004 | Morelle et al. | |
| 2004/0086437 A1 | 5/2004 | Jackson et al. | |
| 2004/0101176 A1 | 5/2004 | Mendonca et al. | |
| 2004/0101177 A1 | 5/2004 | Zahlmann et al. | |
| 2004/0116807 A1 | 6/2004 | Amrami et al. | |
| 2004/0120557 A1 | 6/2004 | Sabol | |
| 2004/0122311 A1 | 6/2004 | Cosman | |
| 2004/0125918 A1 | 7/2004 | Shanmugavel et al. | |
| 2004/0138557 A1 | 7/2004 | Le et al. | |
| 2004/0143449 A1 | 7/2004 | Behrenbruch et al. | |
| 2004/0153128 A1 | 8/2004 | Suresh et al. | |
| 2004/0162492 A1 | 8/2004 | Kobayashi | |
| 2004/0171924 A1 | 9/2004 | Mire et al. | |
| 2004/0183022 A1 | 9/2004 | Weinberg | |
| 2004/0184644 A1 | 9/2004 | Leichter et al. | |
| 2004/0193453 A1 | 9/2004 | Butterfield et al. | |
| 2004/0204646 A1 | 10/2004 | Nagler et al. | |
| 2004/0205343 A1 | 10/2004 | Forth et al. | |
| 2004/0210126 A1 | 10/2004 | Hajaj et al. | |
| 2004/0238743 A1 | 12/2004 | Gravrand et al. | |
| 2004/0251419 A1 | 12/2004 | Nelson et al. | |
| 2004/0253177 A1 | 12/2004 | Elmaleh et al. | |
| 2004/0263865 A1 | 12/2004 | Pawlak et al. | |

| | | |
|---|---|---|
| 2005/0001170 A1 | 1/2005 | Juni |
| 2005/0006589 A1 | 1/2005 | Joung et al. |
| 2005/0020898 A1 | 1/2005 | Vosniak et al. |
| 2005/0020915 A1 | 1/2005 | Belardinelli et al. |
| 2005/0023474 A1 | 2/2005 | Persyk et al. |
| 2005/0029277 A1 | 2/2005 | Tachibana |
| 2005/0033157 A1 | 2/2005 | Klein et al. |
| 2005/0049487 A1 | 3/2005 | Johnson et al. |
| 2005/0055174 A1 | 3/2005 | David et al. |
| 2005/0056788 A1 | 3/2005 | Juni |
| 2005/0074402 A1 | 4/2005 | Cagnolini et al. |
| 2005/0107698 A1 | 5/2005 | Powers et al. |
| 2005/0107914 A1 | 5/2005 | Engleson et al. |
| 2005/0108044 A1 | 5/2005 | Koster |
| 2005/0113945 A1 | 5/2005 | Engleson et al. |
| 2005/0121505 A1 | 6/2005 | Metz et al. |
| 2005/0131270 A1 | 6/2005 | Weil et al. |
| 2005/0145797 A1 | 7/2005 | Oaknin et al. |
| 2005/0148869 A1 | 7/2005 | Masuda |
| 2005/0149350 A1 | 7/2005 | Kerr et al. |
| 2005/0156115 A1 | 7/2005 | Kobayashi et al. |
| 2005/0173643 A1 | 8/2005 | Tumer |
| 2005/0187465 A1 | 8/2005 | Motomura et al. |
| 2005/0198800 A1 | 9/2005 | Reich |
| 2005/0203389 A1 | 9/2005 | Williams |
| 2005/0205792 A1 | 9/2005 | Rousso et al. |
| 2005/0205796 A1 | 9/2005 | Bryman |
| 2005/0211909 A1 | 9/2005 | Smith |
| 2005/0215889 A1 | 9/2005 | Patterson, II |
| 2005/0234424 A1 | 10/2005 | Besing et al. |
| 2005/0247893 A1 | 11/2005 | Fu et al. |
| 2005/0253073 A1 | 11/2005 | Joram et al. |
| 2005/0261936 A1 | 11/2005 | Silverbrook et al. |
| 2005/0261937 A1 | 11/2005 | Silverbrook et al. |
| 2005/0261938 A1 | 11/2005 | Silverbrook et al. |
| 2005/0266074 A1 | 12/2005 | Zilberstein et al. |
| 2005/0277833 A1 | 12/2005 | Williams, Jr. |
| 2005/0277911 A1 | 12/2005 | Stewart et al. |
| 2005/0278066 A1 | 12/2005 | Graves et al. |
| 2005/0288869 A1 | 12/2005 | Kroll et al. |
| 2006/0000983 A1 | 1/2006 | Charron et al. |
| 2006/0033028 A1 | 2/2006 | Juni |
| 2006/0036157 A1 | 2/2006 | Tumer |
| 2006/0072799 A1 | 4/2006 | McLain |
| 2006/0104519 A1 | 5/2006 | Stoeckel et al. |
| 2006/0109950 A1 | 5/2006 | Arenson et al. |
| 2006/0122503 A1 | 6/2006 | Burbank et al. |
| 2006/0145081 A1 | 7/2006 | Hawman |
| 2006/0160157 A1 | 7/2006 | Zuckerman |
| 2006/0188136 A1 | 8/2006 | Ritt et al. |
| 2006/0214097 A1 | 9/2006 | Wang et al. |
| 2006/0237652 A1 | 10/2006 | Kimchy et al. |
| 2006/0257012 A1 | 11/2006 | Kaufman et al. |
| 2007/0116170 A1 | 5/2007 | De Man et al. |
| 2007/0133852 A1 | 6/2007 | Collins et al. |
| 2007/0156047 A1 | 7/2007 | Nagler et al. |
| 2007/0166227 A1 | 7/2007 | Liu et al. |
| 2007/0166297 A1 | 7/2007 | Liu et al. |
| 2007/0189436 A1 | 8/2007 | Goto et al. |
| 2007/0194241 A1 | 8/2007 | Rousso et al. |
| 2007/0265230 A1 | 11/2007 | Rousso et al. |
| 2008/0029704 A1 | 2/2008 | Hefetz et al. |
| 2008/0033291 A1 | 2/2008 | Rousso et al. |
| 2008/0036882 A1 | 2/2008 | Uemura et al. |
| 2008/0039721 A1 | 2/2008 | Shai et al. |
| 2008/0042067 A1 | 2/2008 | Rousso et al. |
| 2008/0128626 A1 | 6/2008 | Rousso et al. |
| 2008/0137938 A1 | 6/2008 | Zahniser |
| 2008/0230705 A1 | 9/2008 | Rousso et al. |
| 2008/0237482 A1 | 10/2008 | Shahar et al. |
| 2008/0260228 A1 | 10/2008 | Dichterman et al. |
| 2008/0260580 A1 | 10/2008 | Helle et al. |
| 2008/0260637 A1 | 10/2008 | Dickman |
| 2008/0277591 A1 | 11/2008 | Shahar et al. |
| 2009/0001273 A1 | 1/2009 | Hawman |
| 2009/0018412 A1 | 1/2009 | Schmitt |
| 2009/0078875 A1 | 3/2009 | Rousso et al. |
| 2009/0112086 A1 | 4/2009 | Melman |
| 2009/0152471 A1 | 6/2009 | Rousso et al. |
| 2009/0190807 A1 | 7/2009 | Rousso et al. |
| 2009/0201291 A1 | 8/2009 | Ziv et al. |
| 2009/0236532 A1 | 9/2009 | Frach et al. |
| 2010/0006770 A1 | 1/2010 | Balakin |
| 2010/0021378 A1 | 1/2010 | Rousso et al. |
| 2010/0102242 A1 | 4/2010 | Burr et al. |
| 2010/0121184 A1 | 5/2010 | Dhawale et al. |
| 2010/0140483 A1 | 6/2010 | Rousso et al. |
| 2010/0202664 A1 | 8/2010 | Busch et al. |
| 2010/0245354 A1 | 9/2010 | Rousso et al. |
| 2012/0172699 A1 | 7/2012 | Nagler et al. |
| 2012/0248320 A1 | 10/2012 | Wangerin et al. |
| 2012/0326034 A1 | 12/2012 | Sachs et al. |
| 2013/0114792 A1 | 5/2013 | Zilberstein et al. |

FOREIGN PATENT DOCUMENTS

| | | |
|---|---|---|
| DE | 19815362 | 10/1999 |
| EP | 0273257 | 7/1988 |
| EP | 0525954 | 2/1993 |
| EP | 0526970 | 2/1993 |
| EP | 0543626 | 5/1993 |
| EP | 0592093 | 4/1994 |
| EP | 0697193 | 2/1996 |
| EP | 0813692 | 12/1997 |
| EP | 0887661 | 12/1998 |
| EP | 1237013 | 9/2002 |
| GB | 2031142 | 4/1980 |
| JP | 59-141084 | 8/1984 |
| JP | 61-026879 | 2/1986 |
| JP | 01-324568 | 6/1986 |
| JP | 03-121549 | 5/1991 |
| JP | 04-151120 | 5/1992 |
| JP | 6-109848 | 4/1994 |
| JP | 06-109848 | 4/1994 |
| JP | 07-059763 | 3/1995 |
| JP | 07-141523 | 6/1995 |
| JP | 08-292268 | 11/1996 |
| JP | 10-260258 | 9/1998 |
| JP | 11-072564 | 3/1999 |
| WO | WO 92/00402 | 9/1992 |
| WO | WO 98/16852 | 4/1998 |
| WO | WO 99/03003 | 1/1999 |
| WO | WO 99/30610 | 6/1999 |
| WO | WO 99/39650 | 8/1999 |
| WO | WO 00/10034 | 2/2000 |
| WO | WO 00/31522 | 2/2000 |
| WO | WO 00/22975 | 4/2000 |
| WO | WO 00/25268 | 5/2000 |
| WO | WO 00/18294 | 6/2000 |
| WO | WO 00/38197 | 6/2000 |
| WO | WO 01/89384 | 11/2001 |
| WO | WO 02/58531 | 1/2002 |
| WO | WO 02/16965 | 2/2002 |
| WO | WO 02/075357 | 9/2002 |
| WO | WO 03/073938 | 9/2003 |
| WO | WO 03/086170 | 10/2003 |
| WO | WO 2004/004787 | 1/2004 |
| WO | WO 2004/032151 | 4/2004 |
| WO | WO 2004/042546 | 5/2004 |
| WO | WO 2004/113951 | 12/2004 |
| WO | WO 2005/002971 | 1/2005 |
| WO | WO 2005/059592 | 6/2005 |
| WO | WO 2005/059840 | 6/2005 |
| WO | WO 2005/067383 | 7/2005 |
| WO | WO 2005/104939 | 11/2005 |
| WO | WO 2005/118659 | 12/2005 |
| WO | WO 2005/119025 | 12/2005 |
| WO | WO 2006/042077 | 4/2006 |
| WO | WO 2006/051531 | 5/2006 |
| WO | WO 2006/054296 | 5/2006 |
| WO | WO 2006/075333 | 7/2006 |
| WO | WO 2006/129301 | 12/2006 |
| WO | WO 2007/010534 | 1/2007 |
| WO | WO 2007/010537 | 1/2007 |
| WO | WO 2007/054935 | 5/2007 |

(56) References Cited

FOREIGN PATENT DOCUMENTS

| WO | WO 2007/074467 | 7/2007 |
|---|---|---|
| WO | WO 2008/010227 | 1/2008 |
| WO | WO 2008/075362 | 6/2008 |

OTHER PUBLICATIONS

Lavallée et al. "Building a Hybrid Patient's Model for Augmented Reality in Surgery: A Registration Problem", Computing in Biological Medicine, 25(2): 149-164, 1995. p. 149-150.
Kojima et al. "Quantitative Planar Imaging Method for Measurement of Renal Activity by Using a Conjugate-Emission Image and Transmission Data", Medical Physics, 27(3): 608-615, 2000. p. 608.
Pardridge et al. "Tracer Kinetic Model of Blood-Brain Barrier Transport of Plasma Protein-Bound Ligands", Journal of Clinical Investigation, 74: 745-752, 1984.
Reutter et al. "Direct Least Squares Estimation of Spatiotemporal Distributions From Dynamic SPECT Projections Using a Spatial Segmentation and Temporal B-Splines", IEEE Transactions on Medical Imaging, 19(5): 434-450, 2000.
Huesman et al. "Kinetic Parameter Estimation From SPECT Cone-Beam Projection Measurements", Physics in Medicine and Biology, 43(4): 973-982, 1998.
Reutter et al. "Kinetic Parameter Estimation From Attenuated SPECT Projection Measurements", IEEE Transactions on Nuclear Science, 45(6): 3007-3013, 1998.
Garcia et al. "Accuracy of Dynamic SPECT Acquisition for Tc-99m Teboroxime Myocardial Perfusion Imaging: Preliminary Results", American College of Cardiology, 51st Annual Scientific Session, Atlanta, Georgia, USA, 8 P., 2002.
Piperno et al. "Breast Cancer Screening by Impedance Measurements", Frontiers Med. Biol. Engng., 2(2): 11-17, 1990.
Rajshekhar "Continuous Impedance Monitoring During CT-Guided Stereotactic Surgery: Relative Value in Cystic and Solid Lesions", British Journal of Neurosurgery, 6: 439-444, 1992.
Jessup "Tumor Markers—Prognostic and Therapeutic Implications for Colorectal Carcinoma", Surgical Oncology, 7: 139-151, 1998.
Corstens et al. "Nuclear Medicine's Role in Infection and Inflammation", The Lancet, 354: 765-770, 1999.
Mori et al. "Overexpression of Matrix Metalloproteinase-7mRNA in Human Colon Carcinomas", Cancer, 75: 1516-1519, 1995.
Erbil et al. "Use and Limitations of Serum Total and Lipid-Bound Sialic Acid Concentrations as Markers for Colorectal Cancer", Cancer, 55: 404-409, 1985.
Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.
Day et al. "Localization of Radioiodinated Rat Fibrogen in Transplanted Rat Tumors", J. Nat. Cancer Inst., 23: 799-812, 1959.
Aoi et al. "Absolute Quantitation of Regional Myocardial Blood Flow of Rats Using Dynamic Pinhole SPECT", IEEE Nuclear Science Symposium and Medical Imaging Conference Record, 3: 1780-1783, 2002. Abstract, Figs.
Hassan et al. "A Radiotelemetry Pill for the Measurement of Ionising Radiation Using a Mercuric Iodide Detector", Physics in Medicine and Biology, 23(2): 302-308, 1978.
Hoffman et al. "Intraoperative Probes and Imaging Probes", European Journal of Nuclear Medicine, 26(8): 913-935, 1999.
Zhang et al. "An Innovative High Efficiency and High Resolution Probe for Prostate Imaging", The Journal of Nuclear Medicine, 68: 18, 2000. Abstract.
Jeanguillaume et al, "From the Whole-Body Counting to Imaging: The Computert Aided Collimation Gamma Camera Project (CACAO)", Radiation Projection Dosimetry, 89(3-4):349-352, 2000.
Quartuccia et al, "Computer Assisted Collimation Gamma Camera: A New Approach to Imaging Contaminated Tissues", Radiation Projection Dosimetry, 89(3-4):343-348, 2000.

Communication Pursuant to Article 96(2) EPC Dated Jun. 19, 2006 From the European Patent Office Re.: Application No. 03810570.6.
Communication pursuant to Article 96(2) EPC Dated Aug. 30, 2007 From the European Patent Office Re.: Application No. 03810570.6.
Communication Relating to the Results of the Partial International Search Dated Apr. 18, 2007 From the International Searching Authority of the Patent Cooperation Treaty Re.: Application No. PCT/IL2006/001291.
Communication Relating to the Results of the Partial International Search Dated May 21, 2008 From the International Searching Authority of the Patent Cooperation Treaty Re.: Application No. PCT/IL2007/001588.
International Search Report Dated Jul. 11, 2008 From the International Searching Authority of the Patent Cooperation Treaty Re.: Application No. PCT/IL06/01511.
International Search Report May 24, 2007 From the International Searching Authority of the Patent Cooperation Treaty Re.: Application No. PCT/IL05/00575.
International Search Report Dated Nov. 1, 2007 From the International Searching Authority of the Patent Cooperation Treaty Re.: Application No. PCT/IL06/00840.
International Search Report Dated Jul. 25, 2008 From the International Searching Authority of the Patent Cooperation Treaty Re.: Application No. PCT/IL2007/001588.
International Search Report Dated Feb. 1, 2006 From the International Searching Authority of the Patent Cooperation Treaty Re.: Application No. PCT/IL05/00048.
International Search Report Dated Jul. 1, 2008 From the International Searching Authority of the Patent Cooperation Treaty Re.: Application No. PCT/IL06/00834.
International Search Report Dated Jul. 2, 2007 From the International Searching Authority of the Patent Cooperation Treaty Re.: Application No. PCT/IL2006/001291.
International Search Report Dated Aug. 3, 2006 From the International Searching Authority of the Patent Cooperation Treaty Re.: Application No. PCT/IL05/001173.
International Search Report Dated May 11, 2006 From the International Searching Authority of the Patent Cooperation Treaty Re.: Application No. PCT/IL05/001215.
International Search Report Dated Sep. 11, 2002 From the International Searching Authority of the Patent Cooperation Treaty Re.: Application No. PCT/IL01/00638.
International Search Report Dated Mar. 18, 2004 From the International Searching Authority of the Patent Cooperation Treaty Re.: Application No. PCT/IL03/00917.
International Search Report Dated Mar. 23, 2006 From the International Searching Authority of the Patent Cooperation Treaty Re.: Application No. PCT/IL05/00572.
International Search Report Dated Mar. 26, 2007 From the International Searching Authority of the Patent Cooperation Treaty Re.: Application No. PCT/IL05/00394.
Official Action Dated Jun. 1, 2006 From the United States Patent and Trademark Office Re.: U.S. Appl. No. 10/686,536.
Official Action Dated Dec. 2, 2007 From the Israeli Patent Office Re.: Application No. 158442.
Official Action Dated May 3, 2007 From the United States Patent and Trademark Office Re.: U.S. Appl. No. 10/240,239.
Official Action Dated Sep. 4, 2008 From the US Patent and Trademark Office Re.: U.S. Appl. No. 10/533,568.
Official Action Dated Sep. 5, 2002 From the United States Patent and Trademark Office Re.: U.S. Appl. No. 12/084,559.
Official Action Dated Oct. 7, 2008 From the US Patent Office Re.: U.S. Appl. No. 10/616,301.
Official Action Dated Aug. 10, 2007 From the United States Patent and Trademark Office Re.: U.S. Appl. No. 10/836,223.
Official Action Dated Jul. 12, 2007 From the US Patent and Trademark Office Re.: U.S. Appl. No. 10/616,301.
Official Action Dated Dec. 13, 2007 From the US Patent and Trademark Office Re.: U.S. Appl. No. 10/616,301.
Official Action Dated Dec. 15, 2006 From the US Patent Office Re.: U.S. Appl. No. 10/616,301.
Official Action Dated Apr. 15, 2008 From the United States Patent and Trademark Office Re.: U.S. Appl. No. 09/641,973.

(56) References Cited

OTHER PUBLICATIONS

Official Action Dated Feb. 15, 2008 From the United States Patent and Trademark Office Re.: U.S. Appl. No. 10/343,792.
Official Action Dated Jul. 15, 2008 From the United States Patent and Trademark Office Re.: U.S. Appl. No. 09/641,973.
Official Action Dated Mar. 15, 2004 From the United States Patent and Trademark Office Re.: U.S. Appl. No. 09/725,316.
Official Action Dated Jan. 17, 2006 From the United States Patent and Trademark Office Re.: U.S. Appl. No. 11/034,007.
Official Action Dated Jul. 17, 2007 From the Israeli Patent Office Re.: Application No. 154323.
Official Action Dated Apr. 20, 2006 From the United States Patent and Trademark Office Re.: U.S. Appl. No. 10/240,239.
Official Action Dated Mar. 21, 2008 From the US Patent and Trademark Office Re.: U.S. Appl. No. 10/533,568.
Official Action Dated Jun. 23, 2006 From the United States Patent and Trademark Office Re.: U.S. Appl. No. 09/727,464.
Official Action Dated Jun. 25, 2008 From the US Patent and Trademark Office Re.: U.S. Appl. No. 10/616,301.
Official Action Dated Sep. 25, 2006 From the US Patent and Trademark Office Re.: U.S. Appl. No. 10/616,301.
Official Action Dated Sep. 30, 2008 From the US Patent and Trademark Office Re.: U.S. Appl. No. 10/616,301.
Supplementary European Search Report Dated Dec. 12, 2005 From the European Patent Office Re.: Application No. 03810570.6.
Supplementary Partial European Search Report Dated Nov. 11, 2008 From the European Patent Office Re.: Application No. 01951883.6.
Written Opinion Dated Feb. 1, 2006 From the International Searching Authority of the Patent Cooperation Treaty Re.: Application No. PCT/IL05/00048.
Written Opinion Dated Jul. 1, 2008 From the International Searching Authority of the Patent Cooperation Treaty Re.: Application No. PCT/IL06/00834.
Written Opinion Dated Oct. 10, 2006 From the International Searching Authority of the Patent Cooperation Treaty Re.: Application No. PCT/IL06/00059.
Written Opinion Dated Mar. 23, 2006 From the International Searching Authority of the Patent Cooperation Treaty Re.: Application No. PCT/IL05/00572.
Written Opinion Dated May 24, 2007 From the International Searching Authority of the Patent Cooperation Treaty Re.: Application No. PCT/IL05/00575.
Written Opinion Dated Jul. 25, 2008 From the International Searching Authority of the Patent Cooperation Treaty Re.: Application No. PCT/IL05/001173.
Written Opinion Dated Mar. 26, 2007 From the International Searching Authority of the Patent Cooperation Treaty Re.: Application No. PCT/IL05/00394.
Gugnin et al "Radiocapsule for Recording the Ionizing Radiation in the Gastrointestinal Tract", UDC 615. 417:616.34-005.1-073.916-71 (All-Union Scientific-Research Institute of medical Instrument Design, Moscow. Translated from Meditsinskaya Tekhnika, 1:21-25, Jan.-Feb. 1972).
Stoddart et al. "New Multi-Dimensional Reconstructions for the 12-Detector, Scanned Focal Point, Single-Photon Tomograph", Physics in Medicine and Biology, XP020021960, 37(3): 579-586, Mar. 1, 1992. p. 582, § 2—p. 585, § 1.
Summons to Attend Oral Proceedings Pursuant to Rule 115(1) EPC Dated Jan. 16, 2009 From the European Patent Office Re.: Application No. 03810570.6.
Supplementary Partial European Search Report Dated Sep. 4, 2007 From the European Patent Office Re.: Application No. 0 2716285.8.
Supplementary Partial European Search Report Dated Nov. 20, 2007 From the European Patent Office Re.: Application No. 02716285.8.
Kinahan et al. "Attenuation Correction for a Combined 3D PET/CT Scanner", Medical Physics, 25(10): 2046-2053, Oct. 1998.
Takahashi et al. "Attenuation Correction of Myocardial SPECT Images With X-Ray CT: Effects of Registration Errors Between X-Ray CT and SPECT", Annals of Nuclear Medicine, 16(6): 431-435, Sep. 2002.
Yu et al. "Using Correlated CT Images in Compensation for Attenuation in PET Image Reconstruction", Proceedings of the SPIE, Applications of Optical Engineering: Proceedings of OE/Midwest '90, 1396: 56-58, 1991.
Zaidi et al. "Magenetic Resonance Imaging-Guided Attenuation and Scatter Corrections in Three-Dimensional Brain Positron Emission Tomography", Medical Physics, 30(5): 937-948, May 2003.
Zaidi et al. "MRI-Guided Attenuation Correction in 3D Brain PET", Neuroimage Human Brain Mapping 2002 Meeting, 16(2): Abstract 504, Jun. 2002.
Final OA dated Jul. 12, 2007.
Invitation to Pay Additional Fees.
Invitation to pay additional fees dated Apr. 18, 2007.
OA dated Sep. 4, 2008.
OA of Jun. 1, 2006.
OA of Aug. 10, 2007.
OA of Jan. 17, 2006.
OA of Jun. 19, 2006.
OA of Dec. 2, 2007.
OA of Jan. 7, 2009.
Official Action Dated May 3, 2007 From the US Patent and Trademark Office Re.: U.S. Appl. No. 10/240,239.
Official Action Dated Oct. 7, 2008 From the US Patent and Trademark Office Re.: U.S. Appl. No. 10/616,301.
Official Action Dated Apr. 15, 2008 From the US Patent and Trademark Office Re.: U.S. Appl. No. 09/727,464.
Official Action Dated Dec. 15, 2006 From the US Patent and Trademark Office Re.: U.S. Appl. No. 10/616,301.
Official Action Dated Feb. 15, 2008 From the US Patent and Trademark Office Re.: U.S. Appl. No. 10/343,792.
Official Action Dated Jul. 15, 2008 From the US Patent and Trademark Office Re.: U.S. Appl. No. 09/641,973.
Official Action Dated Apr. 20, 2006 From the US Patent and Trademark Office Re.: U.S. Appl. No. 10/240,239.
Official Action Dated Dec. 23, 2008 From the US Patent and Trademark Office Re.: U.S. Appl. No. 09/727,464.
Official Action Dated Jun. 23, 2006 From the US Patent and Trademark Office Re.: U.S. Appl. No. 09/727,464.
International Preliminary Report on Patentability Dated Apr. 16, 2009 From the International Bureau of WIPO Re.: Application No. PCT/IL2007/000918.
International Preliminary Report on Patentability Dated Jun. 21, 2007 From the International Bureau of WIPO Re.: Application No. PCT/IL2005/000575.
International Preliminary Report on Patentability Dated Jan. 22, 2009 From the International Bureau of WIPO Re.: Application No. PCT/IL2006/000834.
International Preliminary Report on Patentability Dated Jan. 22, 2009 From the International Bureau of WIPO Re.: Application No. PCT/IL2006/001511.
International Preliminary Report on Patentability Dated May 22, 2007 From the International Preliminary Examining Authority Re.: Application No. PCT/IL06/00059.
International Preliminary Report on Patentability Dated May 22, 2008 From the International Bureau of WIPO Re.: Application No. PCT/IL2006/001291.
International Preliminary Report on Patentability Dated May 24, 2007 From the International Bureau of WIPO Re.: Application No. PCT/IL2005/001173.
International Preliminary Report on Patentability Dated Apr. 26, 2007 From the International Bureau of WIPO Re.: Application No. PCT/IL2005/000394.
International Preliminary Report on Patentability Dated Jan. 31, 2008 From the International Bureau of WIPO Re.: Application No. PCT/IL2006/000840.
International Search Report dated Sep. 12, 2002 from the International Searching Authority of the Patent Cooperation Treaty Re: Application No. PCT/IL02/00057.
International Search Report Dated Oct. 15, 2008 From the International Searching Authority Re.: Application No. PCT/IL07/00918.
Invitation to Pay Additional Fees Dated Jul. 10, 2008 From the International Searching Authority Re.: Application No. PCT/IL06/01511.

(56) References Cited

OTHER PUBLICATIONS

Invitation to Pay Additional Fees Dated Feb. 15, 2007 From the International Searching Authority Re.: Application No. PCT/IL05/00575.
Official Action Dated Nov. 26, 2008 From the US Patent and Trademark Office Re.: U.S. Appl. No. 10/240,239.
Official Action Dated Apr. 29, 2009 From the US Patent and Trademark Office Re.: U.S. Appl. No. 11/980,690.
Response Dated Aug. 14, 2008 to Official Action of Apr. 15, 2008 From the US Patent and Trademark Office Re.: U.S. Appl. No. 09/727,464.
Response Dated Nov. 25, 2005 to Office Action of May 13, 2005 From the Patent Office of the People's Republic of China Re.: Application No. 1817689.5.
Response to the International Search Report and the Written Opinion of Oct. 10, 2006 From the International Searching Authority Re.: Appliction No. PCT/IL06/00059.
Translation of Office Action Dated May 13, 2005 From the Patent Office of the People's Republic of China Re.: Application No. 01817689.5.
Written Opinion Dated Oct. 15, 2008 From the International Searching Authority Re.: Application No. PCT/IL07/00918.
Official Action Dated Apr. 8, 2010 From the US Patent and Trademark Office Re.: U.S. Appl. No. 11/980,690.
Official Action Dated Apr. 28, 2010 From the US Patent and Trademark Office Re.: U.S. Appl. No. 10/616,301.
Response Dated May 10, 2010 to Official Action of Apr. 8, 2010 From the US Patent and Trademark Office Re.: U.S. Appl. No. 11/980,690.
Response Dated May 10, 2010 to Official Action of Jan. 8, 2010 From the US Patent and Trademark Office Re.: U.S. Appl. No. 11/656,548.
Communication Pursuant to Article 94(3) EPC Dated Oct. 21, 2009 From the European Patent Office Re.: Application No. 02716285.8.
Notice of Allowance Dated Sep. 17, 2009 From the US Patent and Trademark Office Re.: U.S. Appl. No. 10/533,568.
Official Action Dated Sep. 1, 2009 From the US Patent and Trademark Office Re.: U.S. Appl. No. 11/794,799.
Official Action Dated Jul. 2, 2004 From the US Patent and Trademark Office Re.: U.S. Appl. No. 09/641,973.
Official Action Dated Sep. 2, 2009 From the US Patent and Trademark Office Re.: U.S. Appl. No. 10/343,792.
Official Action Dated Aug. 11, 2009 From the US Patent and Trademark Office Re.: U.S. Appl. No. 09/641,973.
Official Action Dated Sep. 15, 2009 From the US Patent and Trademark Office Re.: U.S. Appl. No. 10/616,307.
Official Action Dated Sep. 15, 2009 From the US Patent and Trademark Office Re.: U.S. Appl. No. 10/836,223.
Official Action Dated Sep. 16, 2009 From the US Patent and Trademark Office Re.: U.S. Appl. No. 09/727,464.
Official Action Dated Sep. 21, 2009 From the US Patent and Trademark Office Re.: U.S. Appl. No. 11/798,017.
Official Action Dated Aug. 28, 2009 From the US Patent and Trademark Office Re.: U.S. Appl. No. 10/240,239.
Official Action Dated Oct. 30, 2009 From the US Patent and Trademark Office Re.: U.S. Appl. No. 11/980,690.
Response Dated Dec. 10, 2009 to Official Action of Aug. 11, 2009 From the US Patent and Trademark Office Re.: U.S. Appl. No. 09/641,973.
Response Dated Oct. 12, 2009 to Notice of Allowance of Jul. 16, 2009 From the US Patent and Trademark Office Re.: U.S. Appl. No. 12/084,559.
Response Dated Oct. 14, 2009 to Official Action of May 14, 2009 From the US Patent and Trademark Office Re.: U.S. Appl. No. 11/656,548.
Supplementary Partial European Search Report and the European Search Opinion Dated Oct. 16, 2009 From the European Patent Office Re.: Application No. 06756259.5.
Moore et al. "Quantitative Multi-Detector Emission Computerized Tomography Using Iterative Attenuation Compensation", Journal of Nuclear Medicine, XP002549083, 23(8): 706-714, Aug. 1982. Abstract, p. 707, Section 'The Multi-Detector Scanner', First §.
Qi et al. "Resolution and noise Properties of MAP Reconstruction for Fully 3-D PET", IEEE Transactions on Medical Imaging, XP002549082, 19(5): 493-506, May 2000. p. 493, col. 2, Lines 10-21, p. 495, col. 1, Last §.
Wilson et al. "Non-Stationary Noise Characteristics for SPECT Images", Proceedings of the Nuclear Science Symposium and Medical Imaging Conference, Santa Fe, CA, USA, Nov. 2-9, 1991, XP010058168, p. 1736-1740, Nov. 2, 1991. p. 1736, col. 2, Lines 4-6.
Appeal Brief Dated Jan. 19, 2010 to Notice of Appeal of Nov. 16, 2009 From the US Patent and Trademark Office Re.: U.S. Appl. No. 10/616,301.
Notice of Allowance Dated Nov. 23, 2009 From the US Patent and Trademark Office Re.: U.S. Appl. No. 12/084,559.
Notice of Appeal and Pre-Appeal Brief Dated Jan. 4, 2010 to Official Action of Sep. 2, 2009 From the US Patent and Trademark Office Re.: U.S. Appl. No. 10/343,792.
Official Action Dated Mar. 1, 2010 From the US Patent and Trademark Office Re.: U.S. Appl. No. 11/794,799.
Official Action Dated Mar. 2, 2010 From the US Patent and Trademark Office Re.: U.S. Appl. No. 10/836,223.
Official Action Dated Mar. 2, 2010 From the US Patent and Trademark Office Re.: U.S. Appl. No. 11/980,617.
Official Action Dated Dec. 8, 2009 From the US Patent and Trademark Office Re.: U.S. Appl. No. 11/132,320.
Official Action Dated Jan. 8, 2010 From the US Patent and Trademark Office Re.: U.S. Appl. No. 11/656,548.
Official Action Dated Mar. 11, 2010 From the US Patent and Trademark Office Re.: U.S. Appl. No. 11/607,075.
Official Action Dated Feb. 23, 2010 From the US Patent and Trademark Office Re.: U.S. Appl. No. 09/641,973.
Response Dated Jan. 14, 2010 to Official Action of Sep. 15, 2009 From the US Patent and Trademark Office Re.: U.S. Appl. No. 10/836,223.
Response Dated Jan. 21, 2010 to Official Action of Sep. 21, 2009 From the US Patent and Trademark Office Re.: U.S. Appl. No. 11/798,017.
Response Dated Feb. 22, 2010 to Communication Pursuant to Article 94(3) EPC of Oct. 21, 2009 From the European Patent Office Re.: Application No. 02716285.8.
Response Dated Dec. 28, 2009 to Official Action of Aug. 28, 2009 From the US Patent and Trademark Office Re.: U.S. Appl. No. 10/240,239.
Response Dated Dec. 30, 2009 to Official Action of Sep. 1, 2009 From the US Patent and Trademark Office Re.: U.S. Appl. No. 11/794,799.
Response Dated Dec. 30, 2009 to Official Action of Oct. 30, 2009 From the US Patent and Trademark Office Re.: U.S. Appl. No. 11/980,690.
Supplementary Partial European Search Report and the European Search Opinion Dated Dec. 15, 2009 From the European Patent Office Re.: Application No. 06832278.3.
Gilland et al. "A 3D Model of Non-Uniform Attenuation and Detector Response for Efficient Iterative Reconstruction in SPECT", Physics in Medicine and Biology, XP002558623, 39(3): 547-561, Mar. 1994. p. 549-550, Section 2.3 'Active Voxel Reconstruction', p. 551, Lines 4-8.
Gilland et al. "Simultaneous Reconstruction and Motion Estimation for Gated Cardiac ECT", IEEE Transactions on Nuclear Science, XP011077797, 49(5): 2344-2349, Oct. 1, 2002. p. 2344, Section 'Introduction', First §.
Kadrmas et al. "Static Versus Dynamic Teboroxime Myocardial Perfusion SPECT in Canines", IEEE Transactions on Nuclear Science, 47(3): 1112-1117, Jun. 2000.
Li et al. "A HOTLink/Networked PC Data Acquisition and Image Reconstruction System for a High Resolution Whole-Body PET With Respiratory or ECG-Gated Performance", IEEE Nuclear Sience Symposium and Medical Imaging Conference, Norfolk, VA, USA, Nov. 10-16, 2002, XP010663724, 2: 1135-1139, Nov. 10, 2002. p. 1137, First Col., 2nd §.

(56) References Cited

OTHER PUBLICATIONS

Written Opinion Dated Aug. 3, 2006 From the International Searching Authority of the Patent Cooperation Treaty Re.: Application No. CT/IL05/001173.
Notice of Appeal Dated Nov. 16, 2009 to Official Action of Jul. 15, 2009 From the US Patent and Trademark Office Re.: U.S. Appl. No. 10/616,301.
International Search Report Dated Oct. 10, 2006 From the International Searching Authority of the Patent Cooperation Treaty Re.: Application No. PCT/IL06/00059.
Rajshekhar, "Continuous Impedence Monitoring During CT-Guided Stereotactic Surgery: Relative Value in Cystic and Solid Lesions", British Journal of Neurosurgery, 6: 439-444, 1992.
Official Action Dated Apr. 9, 2010 From the US Patent and Trademark Office Re.: U.S. Appl. No. 11/798,017.
Communication Pursuant to Article 94(3) EPC Dated Mar. 8, 2010 From the European Patent Office Re.: Application No. 06832278.3.
Official Action Dated Mar. 19, 2010 From the US Patent and Trademark Office Re.: U.S. Appl. No. 10/240,239.
Response Dated Jun. 3, 2010 to Notice of Appeal and Pre-Appeal Brief of Jan. 4, 2010 to Official Action of Sep. 2, 2009 From the US Patent and Trademark Office Re.: U.S. Appl. No. 10/343,792.
Communication Pursuant to Article 93(3) EPC Dated Mar. 8, 2010 From the European Patent Office Re.: Application No. 06832278.3.
Written Opinion Dated Aug. 3, 2006 From the International Searching Authority of the Patent Cooperation Treaty Re.: Application No. PCT/IL05/001173.
Response Dated May 11, 2010 to Official Action of Mar. 11, 2010 From the US Patent and Trademark Office Re.: U.S. Appl. No. 11/607,075.
Response Dated May 26, 2010 to Official Action of Mar. 19, 2010 From the US Patent and Trademark Office Re.: U.S. Appl. No. 10/240,239.
Communication Pursuant to Article 94(3) EPC Dated Apr. 16, 2010 From the European Patent Office Re. Application No. 01951883.6.
Communication Pursuant to Article 94(3) EPC Dated Jul. 22, 2009 From the European Patent Office Re.: Application No. 06809851.6.
Notice of Allowance Dated Jul. 16, 2009 From the US Patent and Trademark Office Re.: U.S. Appl. No. 12/084,559.
Official Action Dated Jul. 7, 2009 From the US Patent and Trademark Office Re.: U.S. Appl. No. 10/533,568.
Official Action Dated May 13, 2009 From the US Patent and Trademark Office Re.: U.S. Appl. No. 11/798,017.
Official Action Dated May 14, 2009 From the US Patent and Trademark Office Re.: U.S. Appl. No. 11/656,548.
Official Action Dated Jul. 15, 2009 From the US Patent and Trademark Office Re.: U.S. Appl. No. 10/616,301.
Official Action Dated Dec. 16, 2008 From the US Patent and Trademark Office Re.: U.S. Appl. No. 10/343,792.
Official Action Dated Jul. 20, 2009 From the US Patent and Trademark Office Re.: U.S. Appl. No. 11/980,617.
Response Dated Mar. 13, 2008 to Official Action of Dec. 13, 2007 From the US Patent and Trademark Office Re.: U.S. Appl. No. 10/616,301.
Response Dated Mar. 15, 2007 to Official Action of Dec. 15, 2006 From the US Patent and Trademark Office Re.: U.S. Appl. No. 10/616,301.
Response Dated Sep. 22, 2008 to Official Action of Jun. 25, 2008 From US Patent and Trademark Office Re.: U.S. Appl. No. 10/616,301.
Response Dated Oct. 31, 2007 to Official Action of Jul. 12, 2007 From the US Patent and Trademark Office Re.: U.S. Appl. No. 10/616,301.
Second International Search Report Dated Jun. 1, 2009 From the International Searching Authority Re.: Application No. PCT/IL07/00918.
Second Written Opinion Dated Jun. 1, 2009 From the International Searching Authority Re.: Application No. PCT/IL07/00918.

Bloch et al. "Application of Computerized Tomography to Radiation Therapy and Surgical Planning", Proceedings of the IEEE, 71(3): 351-355, Mar. 1983.
Ogawa et al. "Ultra High Resoultion Pinhole SPECT", IEEE Nuclear Science Symposium, 2: 1600-1604, 1998.
Pellegrini et al. "Design of Compact Pinhole SPECT System Based on Flat Panel PMT", IEEE Nuclear Science Symposium Conference Record, 3: 1828-1832, 2003.
Wu et al. "ECG-Gated Pinhole SPECT in Mice With Millimeter Spatial Resolution", IEEE Transactions on Nuclear Science, 47(3): 1218-1221, Jun. 2000.
Amendment After Allowance Under 37 CFR 1.312 Dated Sep. 13, 2010 to Notice of Allowance of Jul. 22, 2010 From the US Patent and Trademark Office Re.: U.S. Appl. No. 11/794,799.
Response Dated Jul. 1, 2010 to Official Action of Mar. 2, 2010 From the US Patent and Trademark Office Re.: U.S. Appl. No. 11/980,617.
Response Dated Jun. 1, 2010 to Official Action of Mar. 1, 2010 From the US Patent and Trademark Office Re.: U.S. Appl. No. 11/794,799.
Response Dated Jul. 8, 2010 to Communication Pursuant to Article 94(3) EPC of Mar. 8, 2010 From the European Patent Office Re.: Application No. 06832278.3.
Response Dated Jul. 26, 2010 to Official Action of Apr. 28, 2010 From the US Patent and Trademark Office Re.: U.S. Appl. No. 10/616,301.
Notice of Allowance Dated Jun. 30, 2010 From the United States Patent and Trademark Office Re.: U.S. Appl. No. 09/727,464.
Official Action Dated Aug. 3, 2010 From the US Patent and Trademark Office Re.: U.S. Appl. No. 11/980,690.
Supplemental Response After Interview Dated Aug. 4, 2010 to Official Action of Mar. 2, 2010 From the US Patent and Trademark Office Re.: U.S. Appl. No. 11/980,617.
Notice of Allowance Dated Jul. 22, 2010 From the US Patent and Trademark Office Re.: U.S. Appl. No. 11/794,799.
Response Dated Aug. 16, 2010 to Communication Pursuant to Article 94(3) EPC of Apr. 16, 2010 From the European Patent Office Re. Application No. 01951883.6.
Supplemental Response Under 37 C.F.R. § 1.125 Dated Aug. 12, 2010 to Telephonic Interview of Aug. 6, 2010 From the US Patent and Trademark Office Re. U.S. Appl. No. 11/980,617.
Communication Pursuant to Article 94(3) EPC Dated May 12, 2010 From the European Patent Office Re.: Application No. 06809851.6.
Notice of Allowance Dated Aug. 25, 2010 From the US Patent and Trademark Office Re. U.S. Appl. No. 11/980,617.
Response Dated Sep. 8, 2010 to Communication Pursuant to Article 94(3) EPC Dated May 12, 2010 From the European Patent Office Re.: Application No. 06809851.6.
Official Action Dated Dec. 8, 2010 From the US Patent and Trademark Office Re.: U.S. Appl. No. 11/980,690.
Official Action Dated Nov. 10, 2010 From the US Patent and Trademark Office Re.: U.S. Appl. No. 10/836,223.
Official Action Dated Nov. 23, 2010 From the US Patent and Trademark Office Re.: U.S. Appl. No. 11/656,548.
Response Dated Nov. 18, 2010 to Official Action of Jul. 19, 2010 From the US Patent and Trademark Office Re.: U.S. Appl. No. 11/607,075.
Official Action Dated Jan. 28, 2011 From the US Patent and Trademark Office Re.: U.S. Appl. No. 09/641,973.
Response Dated Jan. 27, 2011 to Official Action of Nov. 1, 2010 From the US Patent and Trademark Office Re.: U.S. Appl. No. 11/980,690.
Response Dated Jan. 31, 2011 to Official Action of Sep. 30, 2010 From the US Patent and Trademark Office Re.: U.S. Appl. No. 11/798,017.
Response Dated Mar. 8, 2011 to Official Action of Dec. 8, 2010 From the US Patent and Trademark Office Re.: U.S. Appl. No. 11/980,690.
Notice of Allowance Dated Feb. 23, 2011 From the US Patent and Trademark Office Re.: U.S. Appl. No. 11/980,690.
Communication Pursuant to Rules 70(2) and 70a(2) EPC Dated Apr. 4, 2011 From the European Patent Office Re. Application No. 05803689.8.
Response Dated Mar. 31, 2011 to Official Action of Jan. 31, 2011 From the US Patent and Trademark Office Re. U.S. Appl. No. 11/667,793.

(56) References Cited

OTHER PUBLICATIONS

Official Action Dated Sep. 30, 2010 From the US Patent and Trademark Office Re.: U.S. Appl. No. 11/798,017.
Response Dated Oct. 5, 2010 to Official Action of Jul. 19, 2010 From the US Patent and Trademark Office Re.: U.S. Appl. No. 11/656,548.
Beekman et al. "Efficient Fully 3-D Iterative SPECT Reconstruction With Monte Carlo-Based Scatter Compensation", IEEE Transactions on Medical Imaging, 21(8): 867-877, Aug. 2002.
Brown et al. "Method for Segmenting Chest CT Image Data Using an Anatomical Model: Preliminary Results", IEEE Transactions on Medical Imaging, 16(6): 828-839, Dec. 1997.
Del Guerra et al. "An Integrated PET-SPECT Small Animal Imager: Preliminary Results", Nuclear Science Symposium, IEEE Records, 1: 541-544, 1999.
Office Action Dated Dec. 2, 2007 From the Israeli Patent Office Re.: Application No. 158442.
Office Action Dated Sep. 4, 2007 From the Israeli Patent Office Re.: Application No. 157007.
Office Action Dated Jul. 17, 2007 From the Israeli Patent Office Re.: Application No. 154323.
Response dated Sep. 1, 2010 to Official Action of Aug. 3, 2010 From the US Patent and Trademark Office Re.: U.S. Appl. No. 11/980,690.
Interview Summary Dated Mar. 25, 2011 From the US Patent and Trademark Office Re.: U.S. Appl. No. 10/836,223.
Mao et al. "Human Prostatic Carcinoma: An Electron Microscope Study", Cancer Research, XP002625777, 26(5): 955-973, May 1966.
Storey et al. "Tc-99m Sestamibi Uptake in Metastatic Prostate Carcinoma", Clinical Nuclear Medicine, XP009145398, 25(2): 133-134, Feb. 2000.
Response Dated Apr. 5, 2011 to Official Action of Nov. 10, 2010 From the US Patent and Trademark Office Re.: U.S. Appl. No. 10/836,223.
Supplementary European Search Report and the European Search Opinion Dated Mar. 16, 2011 From the European Patent Office Re. Application No. 05803689.8.
Herrmann et al. "Mitochondrial Proteome: Altered Cytochtrome C Oxidase Subunit Levels in Prostate Cancer", Proteomics, XP002625778, 3(9): 1801-1810, Sep. 2003.
Krieg et al. "Mitochondrial Proteome: Cancer-Altered Metabolism Associated With Cytochrome C Oxidase Subunit Level Variation", Proteomics, XP002625779, 4(9): 2789-2795, Sep. 2004.
Communication Pursuant to Article 94(3) EPC Dated Mar. 2, 2011 From the European Patent Office Re.: Application No. 06756259.5.
International Search Report Dated May 24, 2007 From the International Searching Authority of the Patent Cooperation Treaty Re.: Application No. PCT/IL05/00575.
Notice of Allowance Dated Nov. 15, 2010 From the US Patent and Trademark Office Re. U.S. Appl. No. 10/616,301.
Notice of Non-Compliant Amendment Dated Feb. 14, 2011 From the US Patent and Trademark Office Re.: U.S. Appl. No. 10/616,307.
Office Action Dated Jan. 2, 2006 From the Israeli Patent Office Re.: Application No. 154323.
Official Action Dated Jun. 1, 2006 From the US Patent and Trademark Office Re.: U.S. Appl. No. 10/686,536.
Official Action Dated Sep. 5, 2002 From the US Patent and Trademark Office Re.: U.S. Appl. No. 12/084,559.
Official Action Dated Jan. 7, 2009 From the US Patent and Trademark Office Re.: U.S. Appl. No. 10/616,307.
Official Action Dated Aug. 10, 2007 From the US Patent and Trademark Office Re.: U.S. Appl. No. 10/836,223.
Official Action Dated Apr. 15, 2008 From the US Patent and Trademark Office Re.: U.S. Appl. No. 09/641,973.
Official Action Dated Mar. 15, 2004 From the US Patent and Trademark Office Re.: U.S. Appl. No. 09/765,316.
Official Action Dated Mar. 15, 2011 From the US Patent and Trademark Office Re.: U.S. Appl. No. 10/343,792.
Response Dated Feb. 10, 2011 to Notice of Allowance of Nov. 15, 2010 From the US Patent and Trademark Office Re. U.S. Appl. No. 10/616,301.

Response Dated Mar. 24, 2011 to Official Action of Dec. 8, 2010 From the US Patent and Trademark Office Re.: U.S. Appl. No. 09/641,973.
Response Dated Jan. 27, 2011 to Official Action of Nov. 1, 2010 From the US Patent and Trademark Office Re.: U.S. Appl. No. 12/728,383.
Written Opinion Dated Jul. 2, 2007 From the International Searching Authority of the Patent Cooperation Treaty Re.: Application No. PCT/IL2006/001291.
Bromiley et al. "Attenuation Correction in PET Using Consistency Conditions and a Three-Dimensional Template", IEEE Transactions on Nuclear Science, XP002352920, 48(4): 1371-1377, 2001. p. 1376, col. 2, § 2.
Day et al. "Localization of Radioiodinated Rat Fibrogen in Transplanted Rat Tumors", Journal of the National Cancer Institute, 23(4): 799-812, 1959.
Hayakawa et al. "A PET-MRI Registration Technique for PET Studies of the Rat Brain", Nuclear Medicine & Biology, 27: 121-125, 2000. p. 121, col. 1.
Jeanguillaume et al. "From the Whole-Body Counting to Imaging: The Computer Aided Collimation Gamma Camera Project (CACAO)", Radiation Projection Dosimetry, 89(3-4): 349-352, 2000. & RSNA 2000 Infosystem, 87th Scientific Assembly and Annual Meeting, Chicago, Illinois, 2000.
Lavall?e et al. "Building a Hybrid Patient's Model for Augmented Reality in Surgery: A Registration Problem", Computing in Biological Medicine, 25(2): 149-164, 1995.
Lin et al. "Improved Sensor Pills for Physiological Monitoring", NASA Technical Brief, JPL New Technology Report, NPO-20652, 25(2), 2000.
Mettler et al. "Legal Requirements and Radiation Safety", Essentials of Nuclear Medicine Imaging, 2nd Ed., Chap.13: 323-331, 1985.
Quartuccia et al. "Computer Assisted Collimation Gama Camera: A New Approach to Imaging Contaminated Tissues", Radiation Projection Dosimetry, 89(3-4): 343-348, 2000.
Notice of Allowance Dated Dec. 17, 2010 From the US Patent and Trademark Office Re. U.S. Appl. No. 11/980,617.
Official Action Dated Dec. 8, 2010 From the US Patent and Trademark Office Re.: U.S. Appl. No. 09/641,973.
Official Action Dated Dec. 28, 2010 From the US Patent and Trademark Office Re.: U.S. Appl. No. 11/607,075.
Response Dated Dec. 15, 2010 to Official Action of Jul. 19, 2010 From the US Patent and Trademark Office Re.: U.S. Appl. No. 11/656,548.
Official Action Dated Jan. 31, 2011 From the US Patent and Trademark Office Re. U.S. Appl. No. 11/667,793.
Response Dated Dec. 8, 2011 to Restriction Official Action of Nov. 8, 2011 From the US Patent and Trademark Office Re. U.S. Appl. No. 12/309,479.
Communication Pursuant to Article 94(3) EPC Dated Nov. 18, 2011 From the European Patent Office Re. Application No. 05803689.8.
Response Dated Nov. 14, 2011 to Official Action of Jul. 12, 2011 From the US Patent and Trademark Office Re.: U.S. Appl. No. 09/641,973.
Response Dated Nov. 23, 2011 to Official Action of May 23, 2011 From the US Patent and Trademark Office Re.: U.S. Appl. No. 11/980,690.
Response Dated Nov. 28, 2011 to Official Action of Jun. 28, 2011 From the US Patent and Trademark Office Re. U.S. Appl. No. 11/628,074.
Official Action Dated Oct. 7, 2011 From the US Patent and Trademark Office Re. U.S. Appl. No. 11/750,057.
Official Action Dated Oct. 7, 2011 From the US Patent and Trademark Office Re. U.S. Appl. No. 11/932,872.
Interview Summary Dated May 31, 2011 From the US Patent and Trademark Office Re. U.S. Appl. No. 10/616,301.
Notice of Allowance Dated May 5,2011 From the US Patent and Trademark Office Re.: U.S. Appl. No. 10/240,239.
Notice of Allowance Dated May 6, 2011 From the US Patent and Trademark Office Re. U.S. Appl. No. 11/980,617.
Official Action Dated Apr. 20, 2011 From the US Patent and Trademark Office Re.: U.S. Appl. No. 11/798,017.
Official Action Dated May 23, 2011 From the US Patent and Trademark Office Re. U.S. Appl. No. 11/667,793.

(56) References Cited

OTHER PUBLICATIONS

Official Action Dated May 23, 2011 From the US Patent and Trademark Office Re.: U.S. Appl. No. 11/980,690.
Official Action Dated Apr. 27, 2011 From the US Patent and Trademark Office Re.: U.S. Appl. No. 10/836,223.
McJilton et al. "Protein Kinase C? Interacts With Bax and Promotes Survival of Human Prostate Cancer Cells", Oncogene, 22; 7958-7968, 2003.
Xu et al. "Quantitative Expression Profile of Androgen-Regulated Genes in Prostate Cancer Cells and Identification of Prostate-Specific Genes", International Journal of Cancer, 92: 322-328, 2001.
Notice of Allowance Dated Jun. 23, 2011 From the US Patent and Trademark Office Re.: U.S. Appl. No. 10/616,301.
Communication Pursuant to Article 94(3) EPC Dated Sep. 22, 2011 From the European Patent Office Re. Application No. 06756258.7.
Notice of Allowance Dated Sep. 16, 2011 From the US Patent and Trademark Office Re.: U.S. Appl. No. 11/607,075.
Official Action Dated Jul. 11, 2011 From the US Patent and Trademark Office Re.: U.S. Appl. No. 11/980,683.
Official Action Dated Jul. 12, 2011 From the US Patent and Trademark Office Re.: U.S. Appl. No. 09/641,973.
Official Action Dated Sep. 12, 2011 From the US Patent and Trademark Office Re. U.S. Appl. No. 11/980,653.
Official Action Dated Sep. 12, 2011 From the US Patent and Trademark Office Re. U.S. Appl. No. 12/087,150.
Official Action Dated Sep. 13, 2011 From the US Patent and Trademark Office Re. U.S. Appl. No. 11/976,852.
Response Dated Sep. 1, 2011 to Communication Pursuant to Article 94(3) EPC of Mar. 2, 2011 From the European Patent Office Re.: Application No. 06756259.5.
Response Dated Sep. 12, 2011 to Official Action of Jul. 11, 2011 From the US Patent and Trademark Office Re.: U.S. Appl. No. 11/980,683.
Response Dated Jul. 14, 2011 to Official Action of Mar. 15, 2011 From the US Patent and Trademark Office Re.: U.S. Appl. No. 10/343,792.
Response Dated Sep. 20, 2011 to Official Action of Apr. 20, 2011 From the US Patent and Trademark Office Re.: U.S. Appl. No. 11/798,017.
Response Dated Aug. 29, 2011 to Official Action of Apr. 27, 2011 From the US Patent and Trademark Office Re.: U.S. Appl. No. 10/836,223.
Ellestad "Stress Testing: Principles and Practice", XP008143015, 5th Edition, p. 432, Jan. 1, 2003.
Gilland et al. "Long Focal Length, Asymmetric Fan Beam Collimation for Transmission Acquisition With a Triple Camera SPECT System", IEEE Transactions on Nuclear Science, XP011087666, 44(3): 1191-1196, Jun. 1, 1997.
Meyers et al. "Age, Perfusion Test Results and Dipyridamole Reaction", Radiologic Technology, XP008142909, 73(5): 409-414, May 1, 2002.
Zhang et al. "Potential of a Compton Camera for High Performance Scintimammography", Physics in Medicine and Biology, XP020024019, 49(4): 617-638, Feb. 21, 2004.
Notice of Allowance Dated Oct. 11, 2011 From the US Patent and Trademark Office Re. U.S. Appl. No. 11/988,926.
Official Action Dated Oct. 26, 2011 From the US Patent and Trademark Office Re.: U.S. Appl. No. 10/836,223.
Official Action Dated Oct. 27, 2011 From the US Patent and Trademark Office Re.: U.S. Appl. No. 11/656,548.
Response Dated Oct. 14, 2011 to Communication Pursuant to Rules 70(2) and 70a(2) EPC of Apr. 4, 2011 From the European Patent Office Re. Application No. 05803689.8.
Response Dated Oct. 14, 2011 to Supplementary European Search Report and the European Search Opinion of Mar. 16, 2011 From the European Patent Office Re. Application No. 05803689.8.
Restriction Official Action Dated Nov. 8, 2011 From the US Patent and Trademark Office Re. U.S. Appl. No. 12/309,479.
Supplemental Notice of Allowability Dated Oct. 24, 2011 From the US Patent and Trademark Office Re.: U.S. Appl. No. 11/607,075.
Response Dated Nov. 14, 2011 to Official Action of Sep. 12, 2011 From the US Patent and Trademark Office Re. U.S. Appl. No. 12/087,150.
Response Dated Oct. 24, 2011 to Official Action of May 23, 2011 From the US Patent and Trademark Office Re. U.S. Appl. No. 11/667,793.
Restriction Official Action Dated Nov. 15, 2011 From the US Patent and Trademark Office Re. U.S. Appl. No. 11/980,683.
Official Action Dated Dec. 15, 2011 From the US Patent and Trademark Office Re.: U.S. Appl. No. 10/343,792.
Official Action Dated Dec. 20, 2011 From the US Patent and Trademark Office Re. U.S. Appl. No. 12/309,479.
Response Dated Nov. 13, 2011 to Official Action of Sep. 12, 2011 From the US Patent and Trademark Office Re. U.S. Appl. No. 11/980,653.
Response Dated Dec. 29, 2011 to Office Action of Jul. 17, 2007 From the Israeli Patent Office Re.: Application No. 154323.
Berman et al. "Dual-Isotope Myocardial Perfusion SPECT With Rest Thallium-201 and Stress Tc-99m Sestamibi", Cardiology Clinics, 12(2): 261-270, May 1994.
DeGrado et al. "Topics in Integrated Systems Physiology. Tracer Kinetic Modeling in Nuclear Cardiology", Journal of Nuclear Cardiology, 7: 686-700, 2000.
Links "Advances in SPECT and PET Imaging", Annals in Nuclear Medical Science, 13(2): 107-120, Jun. 2000.
Notice of Allowance Dated Oct. 26, 2012 From the US Patent and Trademark Office Re. U.S. Appl. No. 12/514,785.
Official Action Dated Nov. 30, 2012 From the US Patent and Trademark Office Re. U.S. Appl. No. 12/514,785.
Brzymialkiewicz et al. "Evaluation of Fully 3-D Emission Mammotomography With a Compact Cadmium Zinc Telluride Detector", IEEE Transactions on Medical Imaging, 24(7): 868-877, Jul. 2005.
Jan et al. "Preliminary Results From the AROPET", IEEE Nuclear Science Symposium Conference Record, Nov. 4-10, 2001, 3: 1607-1610, 2001.
Ohno et al. "Selection of Optimum Projection Angles in Three Dimensional Myocardial SPECT", IEEE Nuclear Science Symposium Conference Record 2001, 4: 2166-2169, 2001.
Seret et al. "Intrinsic Uniformity Requirements for Pinhole SPECT", Journal of Nuclear Medicine Technology, 34(1): 43-47, Mar. 2006.
Smither "High Resolution Medical Imaging System for 3-D Imaging of Radioactive Sources With 1 mm FWHM Spatial Resolution", Proceedings of the SPIE, Medical Imaging 2003: Physics of Medical Imaging, 5030: 1052-1060, Jun. 9, 2003.
Tornai et al. "A 3D Gantry Single Photon Emission Tomograph With Hemispherical Coverage for Dedicated Breast Imaging", Nuclear Instruments & Methods in Physics Research, Section A, 497: 157-167, 2003.
Official Action Dated Dec. 19, 2012 From the US Patent and Trademark Office Re. U.S. Appl. No. 12/448,473.
Notice of Allowance Dated Dec. 26, 2012 From the US Patent and Trademark Office Re.: U.S. Appl. No. 11/980,690.
Official Action Dated Dec. 28, 2012 From the US Patent and Trademark Office Re.: U.S. Appl. No. 10/343,792.
Charland et al. "The Use of Deconvolution and Total Least Squares in Recovering a Radiation Detector Linc Spread Function", Medical Physics, 25(2): 152-160, Feb. 1998. Abstract Only!
Notice of Panel Decision From Pre-Appeal Brief Review Dated Feb. 29, 2012 From the US Patent and Trademark Office Re.: U.S. Appl. No. 10/836,223.
Official Action Dated Mar. 6, 2012 From the US Patent and Trademark Office Re. U.S. Appl. No. 12/792,856.
Official Action Dated Apr. 16, 2012 From the US Patent and Trademark Office Re.: U.S. Appl. No. 10/836,223.
Official Action Dated Feb. 28, 2012 From the US Patent and Trademark Office Re.: U.S. Appl. No. 09/641,973.
Restriction Official Action Dated Mar. 9, 2012 From the US Patent and Trademark Office Re. U.S. Appl. No. 11/976,852.
Restriction Official Action Dated Apr. 13, 2012 From the US Patent and Trademark Office Re. U.S. Appl. No. 11/989,223.
Advisory Action Before the filing of an Appeal Brief Dated Jul. 12, 2012 From the US Patent and Trademark Office Re. U.S. Appl. No. 11/667,793.

(56) References Cited

OTHER PUBLICATIONS

Official Action Dated May 18, 2012 From the US Patent and Trademark Office Re. U.S. Appl. No. 12/514,785.
Official Action Dated Apr. 19, 2012 From the US Patent and Trademark Office Re. U.S. Appl. No. 11/750,057.
Official Action Dated Apr. 23, 2012 From the US Patent and Trademark Office Re. U.S. Appl. No. 11/932,987.
Examination Report Dated Jun. 22, 2011 From the Government of India, Patent Office, Intellectual Property Building Re. Application No. 2963/CHENP/2006.
International Search Report Dated Jul. 2, 2007 From the International Searching Authority Re. Application No. PCT/IL2006/001291.
Notice of Allowance Dated Feb. 23, 2011 From the US Patent and Trademark Office Re.: U.S. Appl. No. 12/728,383.
Official Action Dated Nov. 1, 2010 From the US Patent and Trademark Office Re.: U.S. Appl. No. 12/728,383.
Official Action Dated Mar. 9, 2011 From the US Patent and Trademark Office Re.: U.S. Appl. No. 10/616,301.
Official Action Dated Apr. 19, 2012 From the US Patent and Trademark Office Re. U.S. Appl. No. 11/750,057.
Official Action Dated Jun. 28, 2011 From the US Patent and Trademark Office Re. U.S. Appl. No. 11/628,074.
Official Action Dated Jul. 30, 2012 From the US Patent and Trademark Office Re.: U.S. Appl. No. 11/980,683.
Response Dated Apr. 7, 2009 to Official Action of Oct. 7, 2008 From the US Patent and Trademark Office Re.: U.S. Appl. No. 10/616,301.
Response Dated Jun. 7, 2011 to Official Action of Mar. 9, 2011 From the US Patent and Trademark Office Re.: U.S. Appl. No. 10/616,301.
Response Dated Jun. 28, 2011 to Official Action of Dec. 28, 2010 From the US Patent and Trademark Office Re.: U.S. Appl. No. 11/607,075.
Berman et al. "Dual-Isotope Myocardial Perfusion SPECT With Rest Thallium-201 and Stress Tc-99m Sestamibi", Nuclear Cardiology, 12(2): 261-270, May 1994.
Bowsher et al. "Treatment of Compton Scattering in Maximum-Likelihood, Expectation-Maximization Reconstructions of SPECT Images", Journal of Nuclear Medicine, 32(6): 1285-1291, 1991.
Chengazi et al. "Imaging Prostate Cancer With Technetium-99m-7E11-C5.3 (CYT-351)", Journal of Nuclear Medicine, 38: 675-682, 1997.
Official Action Dated Aug. 2, 2012 From the US Patent and Trademark Office Re. U.S. Appl. No. 12/087,150.
Handrick et al. "Evaluation of Binning Strategies for Tissue Classification in Computed Tomography Images", Medical Imaging 2006: Image Processing, Proceedings of the SPIE, 6144: 1476-1486, 2006.
Thorndyke et al. "Reducing Respiratory Motion Artifacts in Positron Emission Tomography Through Retrospective Stacking", Medical Physics, 33(7): 2632-2641, Jul. 2006.
Restriction Official Action Dated Aug. 16, 2012 From the US Patent and Trademark Office Re. U.S. Appl. No. 12/448,473.
Official Action Dated Aug. 31, 2012 From the US Patent and Trademark Office Re. U.S. Appl. No. 11/980,653.
Communication Pursuant to Article 94(3) EPC Dated Sep. 17, 2012 From the European Patent Office Re. Application No. 06832278.3.
Ouyang et al. "Incorporation of Correlated Structural Images in PET Image Reconstruction", IEEE Transactions of Medical Imaging, 13(4): 627-640, Dec. 1994.
Cancer Medicine "Radiolabeled Monoclonal Antibodies. Historical Perspective", Cancer Medicine, 5th Ed., Sec.16: Principles of Biotherapeutics, Chap.65: Monoclonal Serotherapy, 2000.
Lange et al. "EM Reconstruction Algorithms for Emission and Transmission Tomography", Journal of Computer Assisted Tomography, 8(2): 306-316, Apr. 1984.
Ohrvall et al. "Intraoperative Gamma Detection Reveals Abdominal Endocrine Tumors More Efficiently Than Somatostatin Receptor Scintigraphy", 6th Conference on Radioimmunodetection and Radioimmunotherapy of Cancer, Cancer, 80: 2490-2494, 1997.
Rockmore et al. "A Maximum Likelihood Approach to Emission Image Reconstruction From Projections", IEEE Transactions on Nuclear Science, 23(4): 1428-1432, Aug. 1976.
Shepp el al. "Maximum Likelihood Reconstruction for Emission Tomography", IEEE Transactions on Medical Imaging, MI-1: 113-122, Oct. 1982.
Sitek et al. "Reconstruction of Dynamic Renal Tomographic Data Acquired by Slow Rotation", The Journal of Nuclear Medicine, 42(11): 1704-1712, Nov. 2001.
Solanski "The Use of Automation in Radiopharmacy", Hospital Pharmacist, 7(4): 94-98, Apr. 2000.
Weldon et al. "Quantification of Inflammatory Bowel Disease Activity Using Technetium-99m HMPAO Labelled Leucocyte Single Photon Emission Computerised Tomography (SPECT)", Gut, 36: 243-250, 1995.
Official Action Dated Oct. 11, 2012 From the US Patent and Trademark Office Re. U.S. Appl. No. 11/976,852.
Official Action Dated Oct. 10, 2012 From the US Patent and Trademark Office Re. U.S. Appl. No. 11/798,017.
Communication Pursuant to Article 94(3) EPC Dated Oct. 26, 2012 From the European Patent Office Re. Application No. 05803689.8.
Communication Pursuant to Article 94(3) EPC Dated Nov. 12, 2012 From the European Patent Office Re. Application No. 06756258.7.
Notice of Allowance Dated Nov. 15, 2012 From the US Patent and Trademark Office Re.: U.S. Appl. No. 11/980,683.
Summons to Attend Oral Proceedings Pursuant to Rule 115(1) EPC Dated Nov. 29, 2012 From the European Patent Office Re. Application No. 06756259.5.
Supplementary European Search Report and the European Search Opinion Dated Nov. 13, 2012 From the European Patent Office Re. Application No. 06728347.3.
Applicant-Initiated Interview Summary Dated Jan. 28, 2013 From the US Patent and Trademark Office Re.: U.S. Appl. No. 11/798,017.
Official Action Dated Feb. 7, 2013 From the US Patent and Trademark Office Re. U.S. Appl. No. 11/980,653.
Advisory Action Before the Filing of an Appeal Brief Dated Feb. 26, 2013 From the US Patent and Trademark Office Re. U.S. Appl. No. 12/514,785.
Notice of Allowance Dated Feb. 21, 2013 From the US Patent and Trademark Office Re. U.S. Appl. No. 11/798,017.
Notice of Allowance Dated Feb. 2, 2012 From the US Patent and Trademark Office Re. U.S. Appl. No. 11/628,074.
Official Action Dated Jan. 19, 2012 From the US Patent and Trademark Office Re. U.S. Appl. No. 11/667,793.
Official Action Dated Jan. 23, 2012 From the US Patent and Trademark Office Re. U.S. Appl. No. 12/087,150.
Jin et al. "Reconstruction of Cardiac-Gated Dynamic SPECT Images", IEEE International Conference on Image Processing 2005, ICIP 2005, Sep. 11-14, 2005, 3: 1-4, 2005.
Toennies et al. "Scatter Segmentation in Dynamic SPECT Images Using Principal Component Analysis", Progress in Biomedical Optics and Imaging, 4(23): 507-516, 2003.
Advisory Action Before the Filing of an Appeal Brief Dated Feb. 26, 2013 From the US Patent and Trademark Office Re. U.S. Appl. No. 11/989,223.
Official Action Dated Nov. 30, 2012 From the US Patent and Trademark Office Re. U.S. Appl. No. 11/989,223.
Notice of Allowance Dated Mar. 14, 2013 From the US Patent and Trademark Office Re.: U.S. Appl. No. 11/798,017.
Official Action Dated Mar. 11, 2013 From the US Patent and Trademark Office Re. U.S. Appl. No. 13/345,719.
Studen "Compton Camera With Position-Sensitive Silicon Detectors", Doctoral Thesis, University of Ljubljana, Faculty of Mathematics and Physics, 36 P.
Applicant-Initiated Interview Summary Dated May 1, 2013 From the US Patent and Trademark Office Re. U.S. Appl. No. 10/343,792.
Applicant-Initiated Interview Summary Dated May 1, 2013 From the US Patent and Trademark Office Re. U.S. Appl. No. 11/980,653.
Advisory Action before the Filing of an Appeal Brief Dated May 21, 2013 From the US Patent and Trademark Office Re. U.S. Appl. No. 11/980,653.
Applicant-Initiated Interview Summary Dated May 9, 2013 From the US Patent and Trademark Office Re. U.S. Appl. No. 12/448,473.
Communication Pursuant to Article 94(3) EPC Dated Sep. 23, 2011 From the European Patent Office Re.: Application No. 06832278.3.

(56) References Cited

OTHER PUBLICATIONS

Written Opinion Dated Nov. 1, 2007 from the International Searching Authority of the Patent Cooperation Treaty Re.: Application No. PCT/IL06/00840.
Written Opinion Dated Jul. 11, 2008 from the International Searching Authority of the Patent Cooperation Treaty Re.: Application No. PCT/IL06/01511.
Communication Under Rule 71(3) EPC Dated Feb. 26, 2013 From the European Patent Office Re. Application No. 06756259.5.
Notice of Allowance Dated Jun. 21, 2013 From the US Patent and Trademark Office Re. U.S. Appl. No. 11/980,653.
Notice of Allowance Dated Jul. 15, 2013 From the US Patent and Trademark Office Re. U.S. Appl. No. 11/932,987.
Notice of Allowance Dated Jul. 19, 2013 From the US Patent and Trademark Office Re. U.S. Appl. No. 11/989,223.
Notice of Allowance Dated Jul. 25, 2013 From the US Patent and Trademark Office Re. U.S. Appl. No. 13/345,719.
Official Action Dated Aug. 5, 2013 From the US Patent and Trademark Office Re. U.S. Appl. No. 12/309,479.
Official Action Dated Jul. 5, 2013 From the US Patent and Trademark Office Re.: U.S. Appl. No. 11/656,548.
Official Action Dated Jun. 12, 2013 From the US Patent and Trademark Office Re. U.S. Appl. No. 12/087,150.
Official Action Dated Aug. 14, 2013 From the US Patent and Trademark Office Re. U.S. Appl. No. 12/448,473.
Official Action Dated Jul. 30, 2013 From the US Patent and Trademark Office Re. U.S. Appl. No. 10/343,792.
Official Action Dated Jul. 31, 2013 From the US Patent and Trademark Office Re. U.S. Appl. No. 11/667,793.
Bacharach et al. "Attenuation Correction in Cardiac Positron Emission Tomography and Single-Photon Emission Computed Tomography", Journal of Nucelar Cardiology, 2(3): 246-255, 1995.
Berman et al. "D-SPECT: A Novel Camera for High Speed Quantitative Molecular Imaging: Initial Clinical Results", The Journal of Nuclear Medicine, 47(Suppl.1): 131P, 2006.
Berman et al. "Myocardial Perfusion Imaging With Technetium-99m-Sestamibi: Comparative Analysis of Available Imaging Protocols", The Journal of Nuclear Medicine, 35: 681-688, 1994.
Borges-Neto et al. "Perfusion and Function at Rest and Treadmill Exercise Using Technetium-99m-Sestamibi: Comparison of One- and Two-Day Protocols in Normal Volunteers", The Journal of Nuclear Medicine, 31(7): 1128-1132, Jul. 1990.
Kwok et al. "Feasability of Simultaneous Dual-Isotope Myocardial Perfusion Acquisition Using a Lower Dose of Sestamibi", European Journal of Nuclear Medicine, 24(3): 281-285, Mar. 1997.
Patton et al. "D-Spect: A New Solid State Camera for High Speed Molecular Imaging", The Journal of Nuclear Medicine, 47(Suppl.1): 189P, 2006.
Uni Magdeburg "Attenuation Map", University of Magdeburg, Germany, Retrieved From the Internet, Archived on Jul. 31, 2002.
Zaidi et al. "Determination of the Attenuation Map in Emission Tomography", Journal of Nuclear Medicine, 44(2): 291-315, 2003.

\* cited by examiner

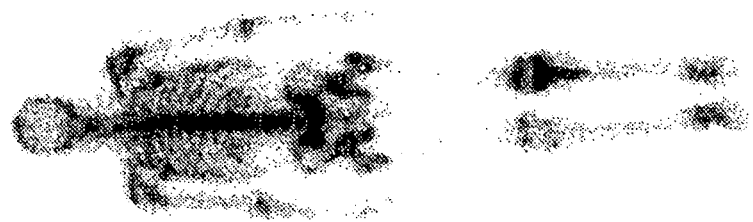
Fig. 26b
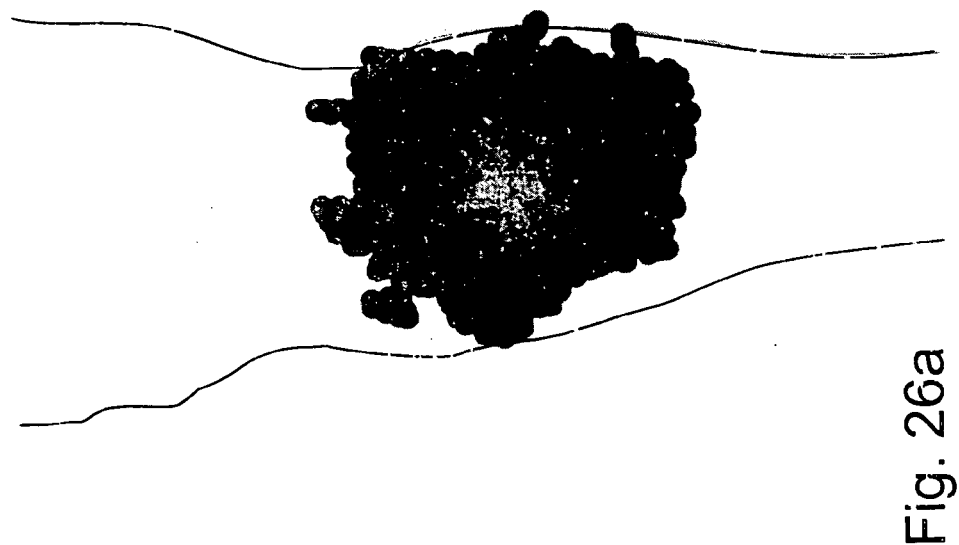
Fig. 26a

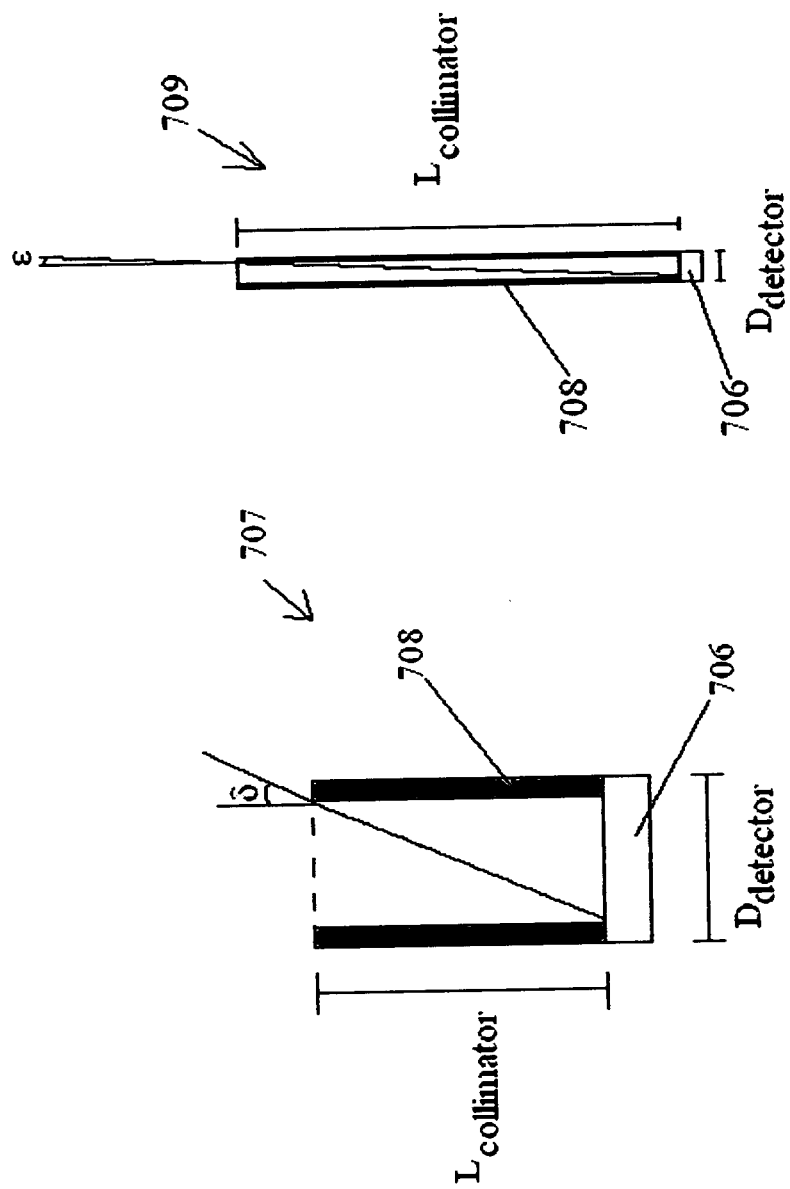

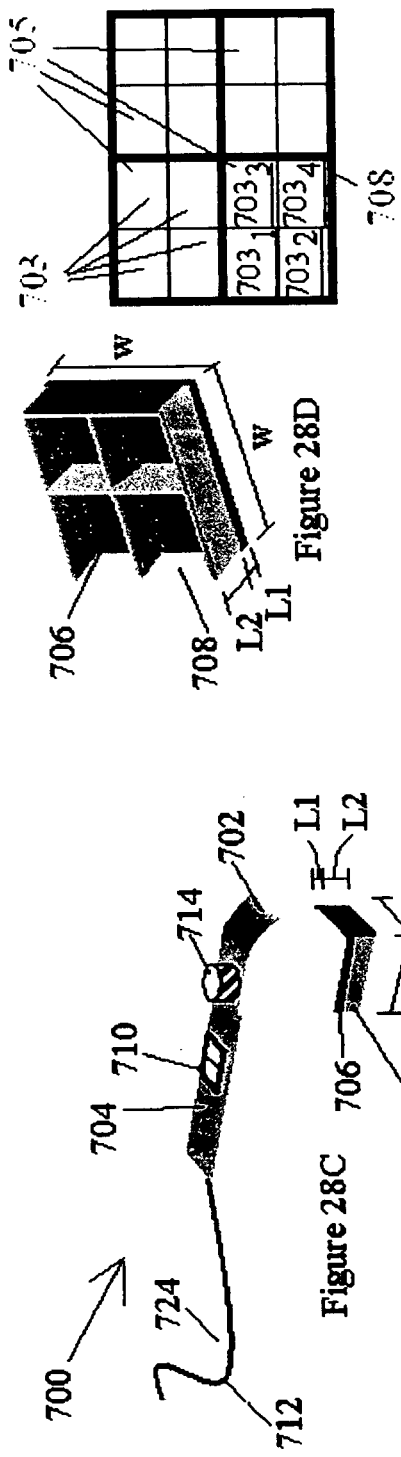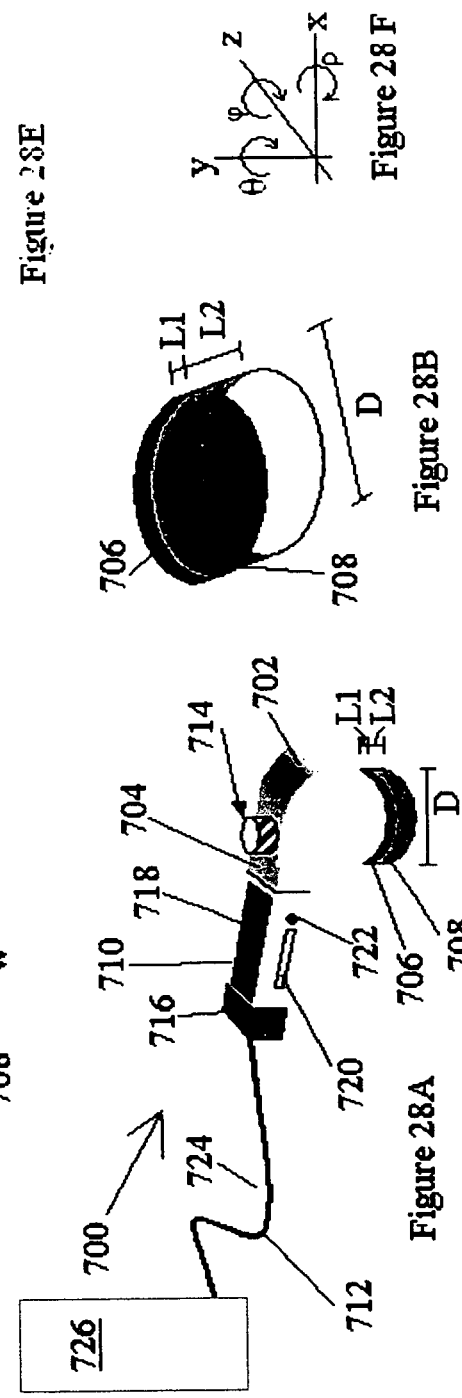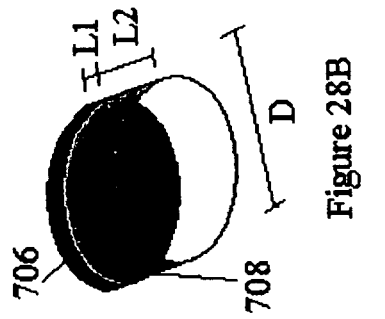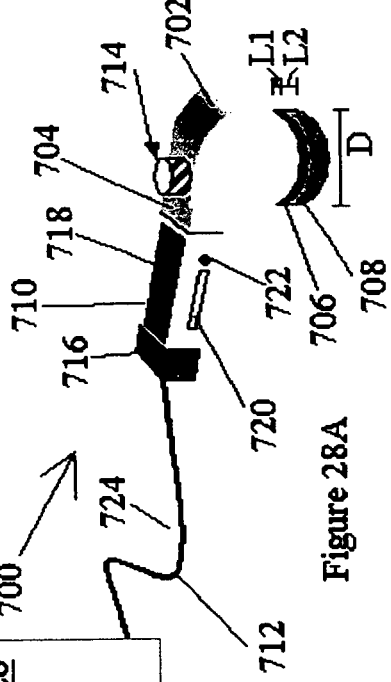

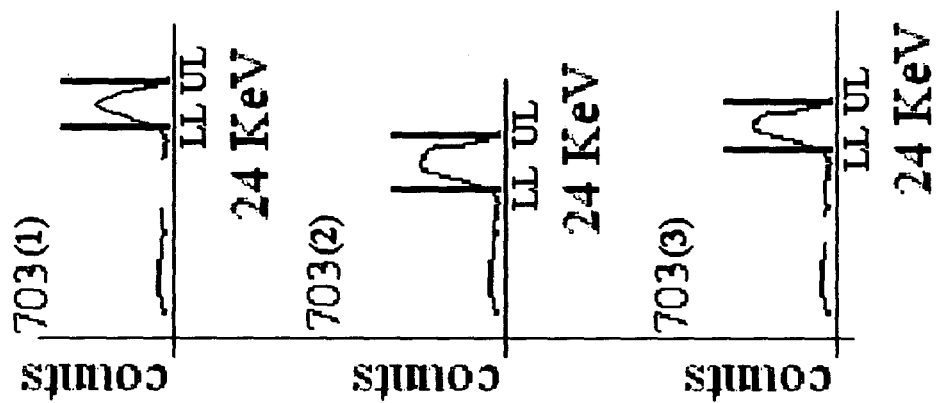
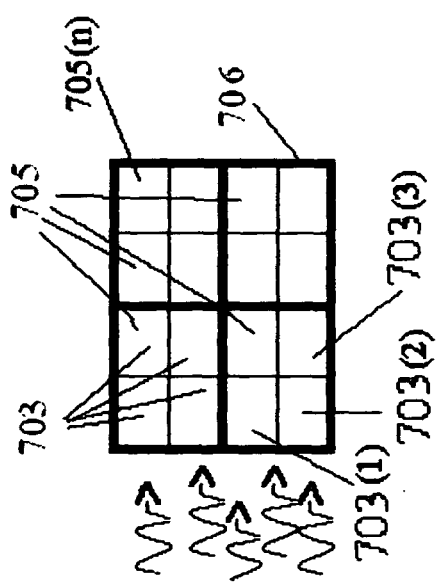
Figure 29B
Figure 29A

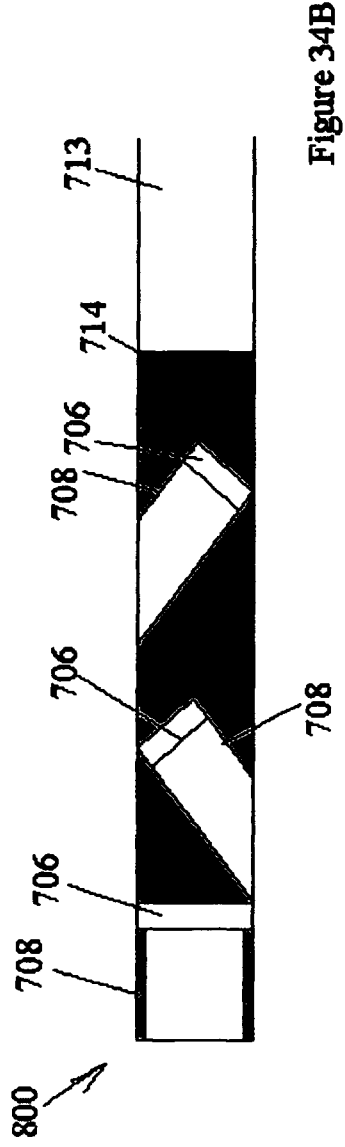
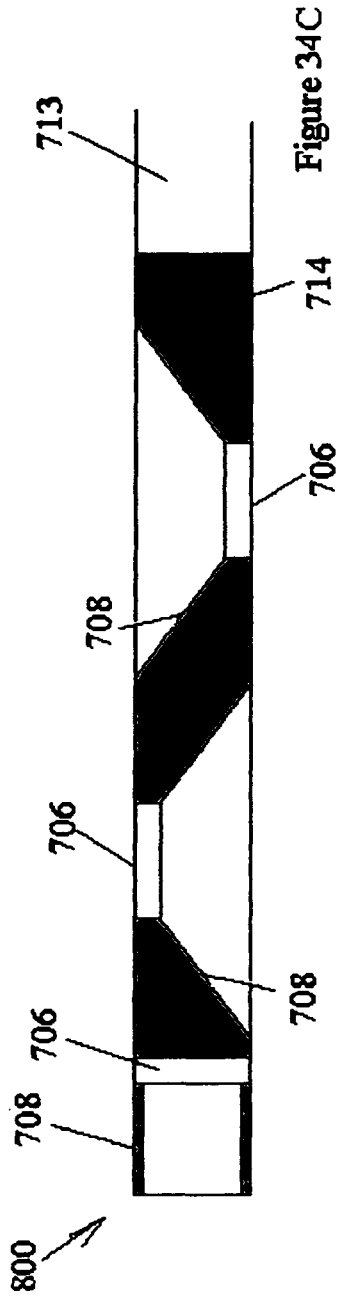

RADIOACTIVE EMISSION DETECTOR EQUIPPED WITH A POSITION TRACKING SYSTEM

This is a continuation-in-part of U.S. patent application Ser. No. 10/343,792, filed on Jul. 11, 2001, which is a National Phase application of PCT/IL01/00638, filed on Jul. 11, 2001, which is a continuation-in-part of U.S. patent application Ser. No. 09/727,464 filed Dec. 4, 2000, which is a continuation-in-part of U.S. patent application Ser. No. 09/714,164, filed Nov. 17, 2000, which is a continuation-in-part of U.S. patent application Ser. No. 09/641,973, filed Aug. 21, 2000. Additionally, this application is filed concurrently with co-pending application "INGESTIBLE PILL," whose disclosure is incorporated herein by reference, and both applications derive priority from U.S. Provisional application No. 60/394,936, filed on Jul. 11, 2002.

FIELD AND BACKGROUND OF THE INVENTION

The present invention relates to a radioactive emission probe equipped with a position tracking system. More particularly, the present invention relates to the functional integration of a radioactive emission probe equipped with a position tracking system as above with medical imaging modalities and (or) with guided minimally-invasive surgical instruments. The present invention is therefore useful for calculating the position of a concentrated radiopharmaceutical in the body in positional context of imaged portions of the body, which information can be used, for example, for performing an efficient minimally invasive surgical procedure. The present invention further relates to a surgical instrument equipped with a position tracking system and a radioactive emission probe for fine in situ localization during resection and (or) biopsy procedures, which surgical instrument is operated in concert with other aspects of the invention.

The use of minimally invasive surgical techniques has dramatically affected the methods and outcomes of surgical procedures. Physically cutting through tissue and organs to visually expose surgical sites in conventional "open surgical" procedures causes tremendous blunt trauma and blood loss. Exposure of internal tissues and organs in this manner also dramatically increases the risk of infection. Trauma, blood loss, and infection all combine to extend recovery times, increase the extent of complications, and require a more intensive care and monitoring regimen. The result of such open surgical procedures is more pain and suffering, higher procedural costs, and greater risk of adverse outcomes.

In sharp contrast, minimally invasive surgical procedures cause little blunt trauma or blood loss and minimize the risk of infection by maintaining the body's natural barriers to infection substantially intact. Minimally invasive surgical procedures result in faster recovery and cause fewer complications than conventional, open, surgical procedures. Minimally invasive surgical procedures, such as laparoscopic, endoscopic, or cystoscopic surgeries, have replaced more invasive surgical procedures in all areas of surgical medicine. Due to technological advancements in areas such as fiber optics, micro-tool fabrication, imaging and material science, the physician performing the operation has easier-to-operate and more cost-effective tools for use in minimally invasive procedures. However, there still exist a host of technical hurdles that limit the efficacy and increase the difficulty of minimally invasive procedures, some of which were overcome by the development of sophisticated imaging techniques. As is further detailed below, the present invention offers further advantages in this respect.

Radionuclide imaging is one of the most important applications of radioactivity in medicine. The purpose of radionuclide imaging is to obtain a distribution image of a radioactively labeled substance, e.g., a radiopharmaceutical, within the body following administration thereof to a patient. Examples of radiopharmaceuticals include monoclonal antibodies or other agents, e.g., fibrinogen or fluorodeoxyglucose, tagged with a radioactive isotope, e.g., $^{99M}$technetium, $^{67}$gallium, $^{201}$thallium, $^{111}$indium, $^{123}$iodine, $^{125}$iodine and $^{18}$fluorine, which may be administered orally or intravenously. The radiopharmaceuticals are designed to concentrate in the area of a tumor, and the uptake of such radiopharmaceuticals in the active part of a tumor, or other pathologies such as an inflammation, is higher and more rapid than in the tissue that neighbors the tumor. Thereafter, a radiation emission detector, typically an invasive detector or a gamma camera (see below), is employed for locating the position of the active area. Another application is the detection of blood clots with radiopharmaceuticals such as ACUTECT from Nycomed Amersham for the detection of newly formed thrombosis in veins, or clots in arteries of the heart or brain, in an emergency or operating room. Yet other applications include radioimaging of myocardial infarct using agents such as radioactive anti-myosin antibodies, radioimaging specific cell types using radioactively tagged molecules (also known as molecular imaging), etc.

The distribution image of the radiopharmaceutical in and around a tumor, or another body structure, is obtained by recording the radioactive emission of the radiopharmaceutical with an external radiation detector placed at different locations outside the patient. The usual preferred emission for such applications is that of gamma rays, which emission is in the energy range of approximately 20-511 KeV. When the probe is placed in contact with the tissue, beta radiation and positrons may also be detected.

The first attempts at radionuclide "imaging" were in the late 1940's. An array of radiation detectors was positioned mechanically on a matrix of measuring points around the head of a patient. Alternatively, a single detector was positioned mechanically for separate measurements at each point on the matrix.

A significant advance occurred in the early 1950's with the introduction of the rectilinear scanner by Ben Cassen. With this instrument, the detector was scanned mechanically in a predetermined pattern over the area of interest.

The first gamma camera capable of recording all points of the image at one time was described by Hal Anger in 1953. Anger used a detector comprising a NaI(Tl) screen and a sheet of X-ray film. In the late 1950's, Anger replaced the film screen with a photomultiplier tube assembly. The Anger camera is described in Hal O. Anger, "Radioisotope camera in Hine GJ", Instrumentation in Nuclear Medicine, New York, Academic Press 1967, chapter 19. U.S. Pat. No. 2,776,377 to Anger, issued in 1957, also describes such a radiation detector assembly.

U.S. Pat. No. 4,959,547 to Carroll et al. describes a probe used to map or provide imaging of radiation within a patient. The probe comprises a radiation detector and an adjustment mechanism for adjusting the solid angle through which radiation may pass to the detector, the solid angle being continuously variable. The probe is constructed so that the only radiation reaching the detector is that which is within the solid angle. By adjusting the solid angle from a maximum to a minimum while moving the probe adjacent the source of radiation and sensing the detected radiation, one is able to locate the probe at the source of radiation. The probe can be used to determine the location of the radioactivity and to provide a point-by-point image of the radiation source or data for mapping the same.

U.S. Pat. No. 5,246,005 to Carroll et al. describes a radiation detector or probe, which uses statistically valid signals to detect radiation signals from tissue. The output of a radiation detector is a series of pulses, which are counted for a predetermined amount of time. At least two count ranges are defined by circuitry in the apparatus and the count range which includes the input count is determined. For each count range, an audible signal is produced which is audibly distrainable from the audible signal produced for every other count range. The mean values of each count range are chosen to be statistically different, e.g., 1, 2, or 3 standard deviations, from the mean of adjacent lower or higher count ranges. The parameters of the audible signal, such as frequency, voice, repetition rate, and (or) intensity are changed for each count range to provide a signal which is discriminable from the signals of any other count range.

U.S. Pat. No. 5,475,219 to Olson describes a system for detecting photon emissions wherein a detector serves to derive electrical parameter signals having amplitudes corresponding with the detected energy of the photon emissions and other signal generating events. Two comparator networks employed within an energy window, which define a function to develop an output, L, when an event-based signal amplitude is equal to or above a threshold value, and to develop an output, H, when such signal amplitude additionally extends above an upper limit. Improved reliability and accuracy is achieved with a discriminator circuit which, in response to these outputs L and H, derives an event output upon the occurrence of an output L in the absence of an output H. This discriminator circuit is an asynchronous, sequential, fundamental mode discriminator circuit with three stable states.

U.S. Pat. Nos. 5,694,933 and 6,135,955 to Madden et al. describe a system and method for diagnostic testing of a structure within a patient's body that has been provided with a radioactive imaging agent, e.g., a radiotracer, to cause the structure to produce gamma rays, associated characteristic x rays, and a continuum of Compton-scattered photons. The system includes a radiation receiving device, e.g., a hand-held probe or camera, an associated signal processor, and an analyzer. The radiation receiving device is arranged to be located adjacent the body and the structure for receiving gamma rays and characteristic X-rays emitted from the structure and for providing a processed electrical signal representative thereof. The processed electrical signal includes a first portion representing the characteristic X-rays received and a second portion representing the gamma rays received. The signal processor removes the signal corresponding to the Compton-scattered photons from the electrical signal in the region of the full-energy gamma ray and the characteristic X-ray. The analyzer is arranged to selectively use the X-ray portion of the processed signal to provide near-field information about the structure, to selectively use both the X-ray and the gamma-ray portions of the processed signal to provide near-field and far-field information about the structure, and to selectively use the gamma-ray portion of the processed signal to provide extended field information about the structure.

U.S. Pat. No. 5,732,704 to Thurston et al. describes a method for identifying a sentinel lymph node located within a grouping of regional nodes at a lymph drainage basin associated with neoplastic tissue wherein a radiopharmaceutical is injected at the situs of the neoplastic tissue. This radiopharmaceutical migrates along a lymph duct towards the drainage basin containing the sentinel node. A hand-held probe with a forwardly disposed radiation detector crystal is maneuvered along the duct while the clinician observes a graphical readout of count rate amplitudes to determine when the probe is aligned with the duct. The region containing the sentinel node is identified when the count rate at the probe substantially increases. Following surgical incision, the probe is maneuvered utilizing a sound output in connection with actuation of the probe to establish increasing count rate thresholds followed by incremental movements until the threshold is not reached and no sound cue is given to the surgeon. At this point of the maneuvering of the probe, the probe detector will be in adjacency with the sentinel node, which then may be removed.

U.S. Pat. No. 5,857,463 to Thurston et al. describes further apparatus for tracking a radiopharmaceutical present within the lymph duct and for locating the sentinel node within which the radiopharmaceutical has concentrated. A smaller, straight, hand-held probe is employed carrying two hand actuable switches. For tracking procedures, the probe is moved in an undulatory manner, wherein the location of the radiopharmaceutical-containing duct is determined by observing a graphic readout. When the region of the sentinel node is approached, a switch on the probe device is actuated by the surgeon to carry out a sequence of squelching operations until a small node locating region is defined.

U.S. Pat. No. 5,916,167 to Kramer et al. and U.S. Pat. No. 5,987,350 to Thurston describe surgical probes wherein a heat-sterilizable and reusable detector component is combined with a disposable handle and cable assembly. The reusable detector component incorporates a detector crystal and associated mountings along with preamplifier components.

U.S. Pat. No. 5,928,150 to Call describes a system for detecting emissions from a radiopharmaceutical injected within a lymph duct wherein a hand-held probe is utilized. When employed to locate sentinel lymph nodes, supplementary features are provided including a function for treating validated photon event pulses to determine count rate level signals. The system includes a function for count-rate based ranging as well as an adjustable threshold feature. A post-threshold amplification circuit develops full-scale aural and visual outputs.

U.S. Pat. Nos. 5,932,879 and 6,076,009 to Raylman et al. describe an intraoperative system for preferentially detecting beta radiation over gamma radiation emitted from a radiopharmaceutical. The system has ion-implanted silicon charged-particle detectors for generating signals in response to received beta particles. A preamplifier is located in proximity to the detector filters and amplifies the signal. The probe is coupled to a processing unit for amplifying and filtering the signal.

U.S. Pat. No. 6,144,876 to Bouton describes a system for detecting and locating sources of radiation, with particular applicability to interoperative lymphatic mapping (ILM) procedures. The scanning probe employed with the system performs with both an audible as well as a visual perceptive output. A desirable stability is achieved in the readouts from the system through a signal processing approach which establishes a floating or dynamic window analysis of validated photon event counts. This floating window is defined between an upper edge and a lower edge. The values of these window edges vary during the analysis in response to compiled count sum values. In general, the upper and lower edges are spaced apart a value corresponding with about four standard deviations.

To compute these count sums, counts are collected over successive short scan intervals of 50 milliseconds and the count segments resulting therefrom are located in a succession of bins within a circular buffer memory. The count sum is generated as the sum of the memory segment count values of a certain number of the bins or segments of memory. Alteration of the floating window occurs when the count sum either exceeds its upper edge or falls below its lower edge. A reported mean, computed with respect to the window edge that is crossed, is developed for each scan interval which, in turn, is utilized to derive a mean count rate signal. The resulting perceptive output exhibits a desirable stability, particularly under conditions wherein the probe detector is in a direct confrontational geometry with a radiation source.

U.S. Pat. No. 5,846,513 teaches a system for detecting and destroying living tumor tissue within the body of a living being. The system is arranged to be used with a tumor localizing radiopharmaceutical. The system includes a percutaneously insertable radiation detecting probe, an associated analyzer, and a percutaneously insertable tumor removing instrument, e.g., a resectoscope. The radiation detecting probe includes a needle unit having a radiation sensor component therein and a handle to which the needle unit is releasably mounted. The needle is arranged to be inserted through a small percutaneous portal into the patient's body and is movable to various positions within the suspected tumor to detect the presence of radiation indicative of cancerous tissue. The probe can then be removed and the tumor removing instrument inserted through the portal to destroy and (or) remove the cancerous tissue. The instrument not only destroys the tagged tissue, but also removes it from the body of the being so that it can be assayed for radiation to confirm that the removed tissue is cancerous and not healthy tissue. A collimator may be used with the probe to establish the probe's field of view.

The main limitation of the system is that once the body is penetrated, scanning capabilities are limited to a translational movement along the line of penetration.

An effective collimator for gamma radiation must be several mm in thickness and therefore an effective collimator for high energy gamma radiation cannot be engaged with a fine surgical instrument such as a surgical needle. On the other hand, beta radiation is absorbed mainly due to its chemical reactivity after passage of about 0.2-3 mm through biological tissue. Thus, the system described in U.S. Pat. No. 5,846,513 cannot efficiently employ high energy gamma detection because directionality will to a great extent be lost and it also cannot efficiently employ beta radiation because too high proximity to the radioactive source is required, whereas body tissue limits the degree of maneuvering the instrument.

The manipulation of soft tissue organs requires visualization (imaging) techniques such as computerized tomography (CT), fluoroscopy (X-ray fluoroscopy), magnetic resonance imaging (MRI), optical endoscopy, mammography or ultrasound which distinguish the borders and shapes of soft tissue organs or masses. Over the years, medical imaging has become a vital part in the early detection, diagnosis and treatment of cancer and other diseases. In some cases medical imaging is the first step in preventing the spread of cancer through early detection and in many cases medical imaging makes it possible to cure or eliminate the cancer altogether via subsequent treatment.

An evaluation of the presence or absence of tumor metastasis or invasion has been a major determinant for the achievement of an effective treatment for cancer patients. Studies have determined that about 30% of patients with essentially newly diagnosed tumor will exhibit clinically detectable metastasis. Of the remaining 70% of such patients who are deemed "clinically free" of metastasis, about one-half are curable by local tumor therapy alone. However, some of these metastasis or even early stage primary tumors do not show with the imaging tools described above. Moreover often enough the most important part of a tumor to be removed for biopsy or surgically removed is the active, i.e., growing part, whereas using only conventional imaging cannot distinguish this specific part of a tumor from other parts thereof and (or) adjacent non affected tissue.

A common practice in order to locate this active part is to mark it with radioactivity tagged materials generally known as radiopharmaceuticals, which are administered orally or intravenously and which tend to concentrate in such areas, as the uptake of such radiopharmaceuticals in the active part of a tumor is higher and more rapid than in the neighboring tumor tissue. Thereafter, a radiation emission detector, typically an invasive detector, is employed for locating the position of the active area.

Medical imaging is often used to build computer models which allow doctors to, for example, guide exact radiation in the treatment of cancer, and to design minimally-invasive or open surgical procedures. Moreover, imaging modalities are also used to guide surgeons to the target area inside the patient's body, in the operation room during the surgical procedure. Such procedures may include, for example, biopsies, inserting a localized radiation source for direct treatment of a cancerous lesion, known as brachytherapy (so as to prevent radiation damage to tissues near the lesion), injecting a chemotherapy agent into the cancerous site or removing a cancerous or other lesions.

The aim of all such procedures is to pin-point the target area as precisely as possible in order to get the most precise biopsy results, preferably from the most active part of a tumor, or to remove such a tumor in its entirety, with minimal damage to the surrounding, non affected tissues.

This goal is yet to be achieved, as most of the common imaging modalities such as fluoroscopy, CT, MRI, mammography or ultrasound demonstrate the position and appearance of the entire lesion with anatomical modifications that the lesion causes to its surrounding tissue, without differentiating between the non-active mass from the physiologically active part thereof.

Furthermore, prior art radiation emission detectors and (or) biopsy probes, while being suitable for identifying the location of the radiation site, leave something to be desired from the standpoint of facilitating the removal or other destruction of the detected cancerous tissue, with minimal trauma.

The combination of modalities, as is offered by the present invention, can reduce the margin of error in locating such tumors. In addition, the possibility of demonstrating the position of the active part of a tumor superimposed on a scan from an imaging modality that shows the organ or tumor, coupled with the possibility to follow a surgical tool in reference to the afflicted area during a surgical procedure will allow for a more precise and controlled surgical procedures to take place, minimizing the aforementioned problems.

The present invention addresses these and other issues which are further elaborated hereinbelow, and offers the physicians and patients more reliable targeting, which in turn will result in less invasive and less destructive surgical procedures and fewer cases of mistaken diagnoses.

SUMMARY OF THE INVENTION

The present invention successfully addresses the shortcomings of the presently known configurations by providing a radioactive emission probe in communication with a position tracking system and the use thereof in a variety of systems and methods of medical imaging and procedures. Specifically, wide aperture collimation—deconvolution algorithms are provided, for obtaining a high-efficiency, high resolution image of a radioactivity emitting source, by scanning the radioactivity emitting source with a probe of a wide-aperture collimator, and at the same time, monitoring the position of the radioactive emission probe, at very fine time intervals, to obtain the equivalence of fine-aperture collimation. The blurring effect of the wide aperture is then corrected mathematically. Furthermore, an imaging method by depth calculations is provided, based on the attenuation of photons of different energies, which are emitted from the same source, coupled with position monitoring.

The present invention has many other applications in the direction of therapeutics, such as, but not limited to, implanting brachytherapy seeds, ultrasound microwave radio-frequency cryotherapy and localized radiation ablations.

Implementation of the methods and systems of the present invention involves performing or completing selected tasks or steps manually, automatically, or a combination thereof. Moreover, according to actual instrumentation and equipment of preferred embodiments of the methods and systems of the present invention, several selected steps could be implemented by hardware or by software on any operating system of any firmware or a combination thereof. For example, as hardware, selected steps of the invention could be implemented as a chip a circuit. As software, selected steps of the invention could be implemented as a plurality of software instructions being executed by a computer using any suitable algorithms. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 26A and 26B are illustrations of radiolabeled patterns observed in images produced by the system of the invention and by a conventional gamma camera, respectively, of skeletal metastasis from medulloblastoma;

FIGS. 27A-27I demonstrate the operation of an algorithm provided by the present invention for estimating the distribution of radiation sources in a control volume;

FIGS. 28A-28F schematically illustrate a handheld probe, in accordance with preferred embodiments of the present invention;

FIGS. 29A-29B schematically illustrate the manner of calibrating the handheld probe of FIGS. 28A-28F, in accordance with a preferred embodiment of the present invention;

FIGS. 34A-34C illustrate endoscopic radioactive emission probes, in accordance with the present invention;

DESCRIPTION OF THE PREFERRED EMBODIMENTS

Figure 1:
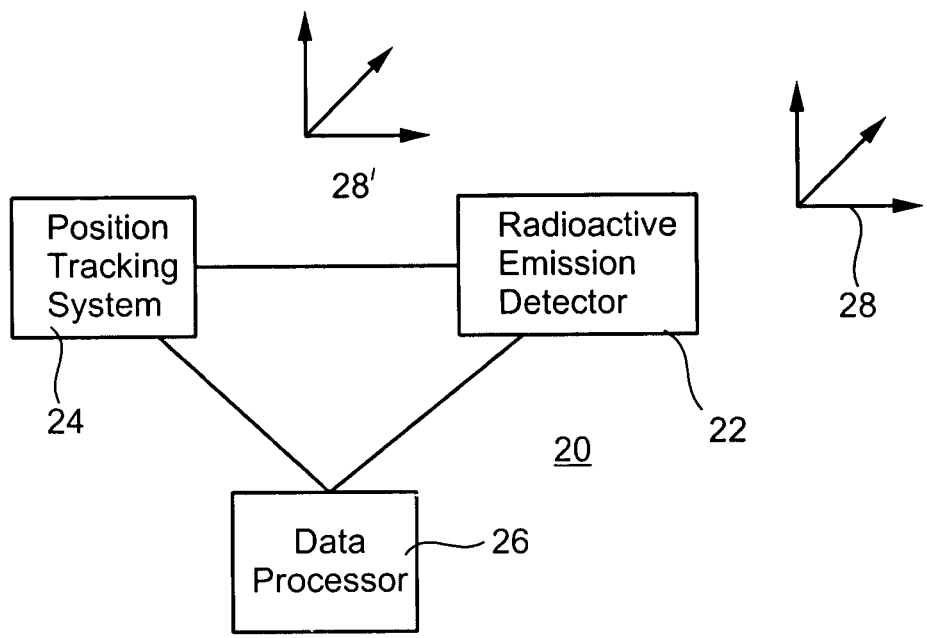
FIG. 1 is a black box diagram of a system according to the teachings of the present invention.

The present invention relates to a radioactive emission probe in communication with a position tracking system and the use thereof in a variety of systems and methods of medical imaging and procedures. Specifically, wide-aperture collimation—deconvolution algorithms are provided, for obtaining a high-efficiency, high resolution image of a radioactivity emitting source, by scanning the radioactivity emitting source with a probe of a wide-aperture collimator, and at the same time, monitoring the position of the radioactive emission probe, at very fine time intervals, to obtain the equivalence of fine-aperture collimation. The blurring effect of the wide aperture is then corrected mathematically. Furthermore, an imaging method by depth calculations is provided, based on the attenuation of photons of different energies, which are emitted from the same source, coupled with position monitoring.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Functional imaging, or the use of radioactive materials to tag physiologically active tissue within the body of a patient, for determining the tissue's localization and demarcation by radioactive emission probes has been disclosed in the medical literature for at least forty years. Functional imaging shows the metabolic activity of body tissue, since dying or damaged body tissue absorbs radiopharmaceuticals at a different rate from a healthy tissue. The functional image may be used for example, to study cardiac rhythm, or respiratory rhythm. However, a functional image may not show structural, or anatomic details.

Significant developments in the localization and demarcation of tissue bearing radioactive isotope tags for diagnostic and (or) therapeutic purposes have occurred since that time. In fact, it is now becoming an established practice in the diagnosis and (or) treatment of certain diseases, e.g., cancer, blood clots, myocardial infarct and abscesses, to introduce monoclonal antibodies or other agents, e.g., fibrinogen, fluorodeoxyglucose labeled with a radioactive isotope (e.g., $^{99M}$Technetium, $^{67}$Gallium, $^{201}$Thallium, $^{111}$Indium, $^{123}$Iodine, $^{18}$Fluorine and $^{125}$Iodine) into the body of the patient. Such radiopharmaceuticals tend to localize in particular tissue or cell type, whereas uptake or binding of the specific radiopharmaceutical is increased in more "physiologically active" tissue such as the active core of a cancerous tissue, so that the radiation emitted following nuclear disintegrations of the isotope can be detected by a radiation detector to better allocate the active portion of a tumor. Such radiation may be, for example, $\alpha$, $\beta^-$, $\beta^+$ and (or) $\gamma$ radiation.

In another type of applications radioactive substances are used to determine the level of flow of blood in blood vessels and the level of perfusion thereof into a tissue, e.g., coronary flow and myocardial perfusion.

Referring now to the drawings, FIG. 1 illustrates a system for calculating a position of a radioactivity emitting source in a system-of-coordinates, in accordance with the teachings of the present invention, which system is referred to hereinbelow as system 20.

Figure 10:
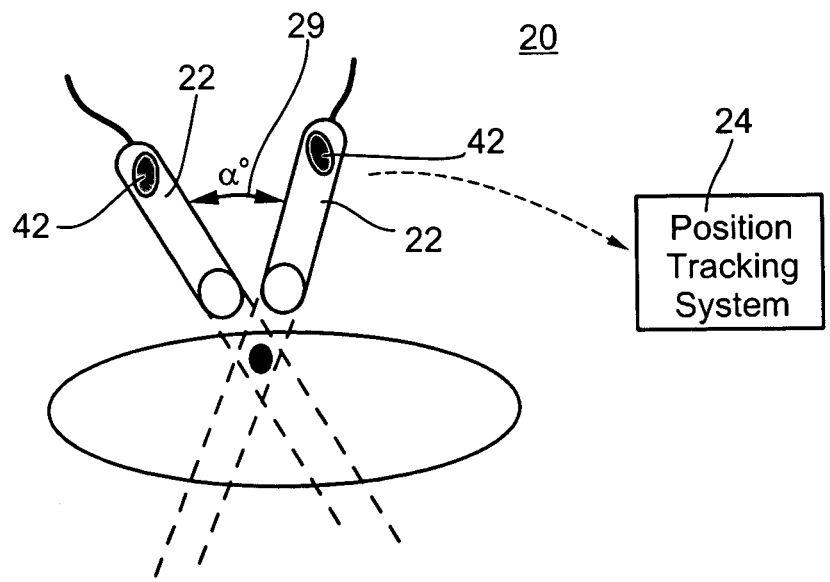
FIG. 10 demonstrates the use of a pair of radiation emission detectors connected therebetween via a connector, preferably a flexible connector or a flexible connection to the connector according to the present invention.

System 20 includes a radioactivity emission detector 22. System 20 according to the present invention further includes a position tracking system 24. System 24 is connected to and (or) communicating with radioactive emission probe 22 so as to monitor the position of detector 22 in a two- or three-dimensional space defined by a system-of-coordinates 28 in two, three or more, say four, five or preferably six degrees-of-freedom (X, Y, Z, $\rho$, $\theta$ and $\phi$). System 20 further includes a data processor 26. Data processor 26 is designed and configured for receiving data inputs from position tracking system 24 and from radioactive emission probe 22 and, as is further detailed below, for constructing the image of the radioactivity emitting source in system-of-coordinates 28. As shown in FIG. 10, a pair (or more) of detectors 22 connected therebetween via a physical connector, each of detectors 22 is position tracked, can be used for constructing the image of the radioactivity emitting source in system-of-coordinates 28. If more than a single detector 22 is used, detectors 22 are preferably connected there between via a connector 29. Connector 29 is preferably flexible. In the alternative, the connections of detectors 22 to connector 29 provide the required flexibility.

It will be appreciated that system 20 of radioactivity emission detector 22 and position tracking system 24 is inherently different from known SPECT and PET imaging systems, as well as from other imaging systems such as X-ray, Mammography, CT, and MRI, since the motion of detector 22 of the present invention is not limited to a predetermined track or tracks, with a respect to an immovable gantry. Rather, detector 22 of the present invention is adapted for a variable-course motion, which may be for example, free-hand scanning, variable-course motion on a linkage system, motion within a body lumen, endoscopic motion through a trocar valve, or another form of variable-course motion.

Position tracking systems per se are well known in the art and may use any one of a plurality of approaches for the determination of position in a two- or three-dimensional space as is defined by a system-of-coordinates in two, three and up to six degrees-of-freedom. Some position tracking systems employ movable physical connections and appropriate movement monitoring devices (e.g., potentiometers) to keep track of positional changes. Thus, such systems, once zeroed, keep track of position changes to thereby determine actual positions at all times. One example for such a position tracking system is an articulated arm.

Figure 2:
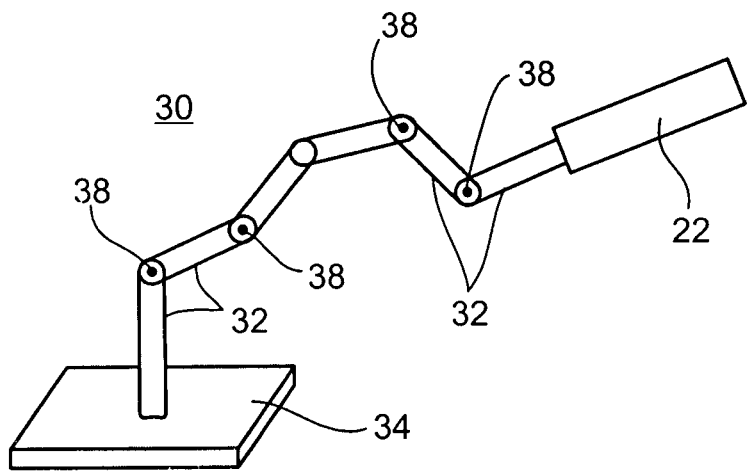
FIG. 2 is a perspective view of an articulated arm which serves as a position tracking system shown carrying a radioactive emission probe in accordance with the teachings of the present invention.

FIG. 2 shows an articulated arm 30 which includes six arm members 32 and a base 34, which can therefore provide positional data in six degrees-of-freedom. Monitoring positional changes may be effected in any one of s veral different ways. For example, providing each arm member 32 with, e.g., potentiometers or optical encoders 38 used to monitor the angle between adjacent arm members 32, to thereby monitor the angular change of each such arm member with respect to adjacent arm members, so as to determine the position in space of radioactive emission probe 22, which is physically connected to articulated arm 30.

Figure 3:
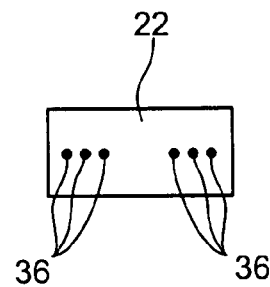
FIG. 3 is a schematic depiction of a radioactive emission probe carrying a pair of three coaxially aligned accelerometers which serve as a position tracking system in accordance with the teachings of the present invention.

As is shown in FIG. 3 other position tracking systems can be attached directly to radioactive emission probe 22 in order to monitor its position in space. An example of such a position tracking system is an assortment of three triaxially (e.g., co-orthogonally) oriented accelerometers 36 which may be used to monitor the positional changes of radioactive emission probe 22 with respect to a space. A pair of such assortments, as is specifically shown in FIG. 3, can be used to determine the position of detector 22 in six-degrees of freedom.

Figure 4:
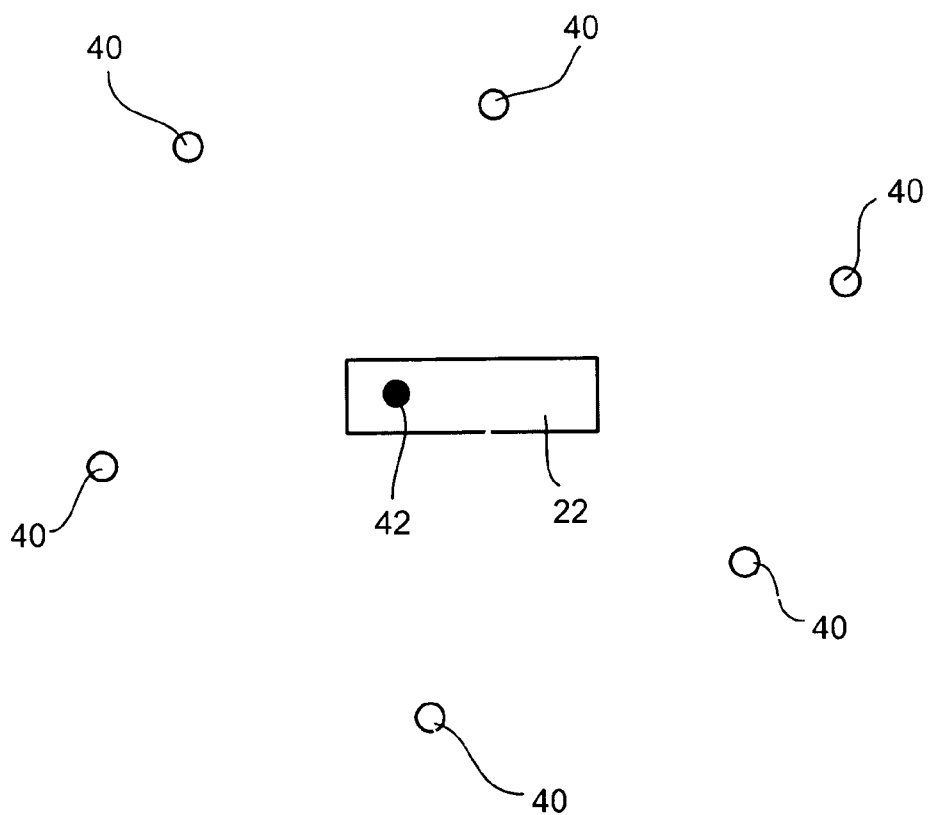
FIG. 4 is a schematic presentation of a radioactive emission probe communicating with yet another type of a position tracking system in accordance with the teachings of the present invention.

As is shown in FIGS. 4 and 10, other position tracking systems re-determine a position irrespective of previous positions, to keep track of positional changes. Such systems typically employ an array of receivers/transmitters 40 which are spread in known positions in a system-of-coordinates and transmitter(s)/receiver(s) 42, respectively, which are in physical connection with the object whose position being monitored. Time based triangulation and (or) phase shift triangulation are used in such cases to periodically determine the position of the monitored object, radioactive emission probe 22 in this case. Examples of such a position tracking systems employed in a variety of contexts using acoustic (e.g., ultrasound) electromagnetic radiation (e.g., infrared, radio frequency) or magnetic field and optical decoding are disclosed in, for example, U.S. Pat. Nos. 5,412,619; 6,083,170; 6,063,022; 5,954,665; 5,840,025; 5,718,241; 5,713,946; 5,694,945; 5,568,809; 5,546,951; 5,480,422 and 5,391,199, which are incorporated by reference as if fully set forth herein.

Radioactive emission probes are well known in the art and may use any one of a number of approaches for the determination of the amount of radioactive emission emanating from an object or portion thereof. Depending on the type of radiation, such detectors typically include substances which when interacting with radioactive decay emitted particles emit either electrons or photons in a level which is proportional over a wide linear range of operation to the level of radiation impinging thereon. The emission of electrons or photons is measurable and therefore serves to quantitatively determine radiation levels. Solid-state detectors in the form of N-type, P-type, PIN-type pixellated or unpixellated include, for example, Ge, Si, CdTe, CdZnTe, CdSe, CdZnSe, $HgI_2$, TlBrI, GaAs, InI, GaSe, Diamond, TlBr, $PbI_2$, InP, ZnTe, HgBrI, a-Si, a-Se, BP, GaP, CdS, SiC, AlSb, PbO, $BiI_3$ and ZnSe detectors. Gas (e.g., $CO_2$ $CH_4$) filled detectors include ionization chamber detectors, proportional chamber detectors and Geiger chamber detectors. Scintillation detectors include organic scintillator crystals and liquids, such as $C_{14}H_{10}$, $C_{14}H_{12}$, $C_{10}H_8$, etc., Plastics, NE102A, NE104, NE110, Pilot U and inorganic scintillator crystals, such as NaI, CsI, BGO, LSO, YSO, BaF, ZnS, ZnO, $CaWO_4$ and $CdWO_4$. Also known are scintillation fiber detectors. Scintillator coupling include photomultiplier tube (PMT) of the following types: side-on type, head-on type, hemispherical type, position sensitive type, icrochannel plate-photomultiplier (MCP-PMTs) and electron multipliers, or photodiodes (and photodiodes arrays), such as Si photodiodes, Si PIN photodiodes, Si APD, GaAs(P) photodiodes, GaP and CCD.

Figure 5:
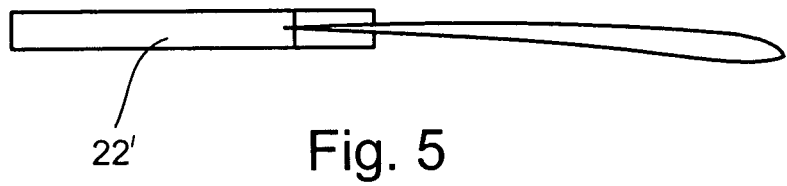
FIG. 5 is a simplified cross-sectional view of a narrow or wide angle radioactive emission probe used to implement an embodiment of the present invention.

FIG. 5 shows a narrow angle or wide angle radioactive emission probe 22'. Narrow or wide angle radioactive emission probe 22' includes a narrow slit (collimator) so as to allow only radiation arriving from a predetermined angular direction (e.g., 1°-280° wide angle, preferably 1°-80°—narrow angle) to enter the detector. Narrow or wide angle radioactive emission probes especially suitable for the configuration shown in FIG. 10 are manufactured, for example, by Neoprobe, Dublin, Ohio (www.neoprobe.com), USA, Nuclear Fields, USA (www.nufi.com) IntraMedical Imaging, Los Angeles, Calif., USA (www.gammaprobe.com).

Figure 6:
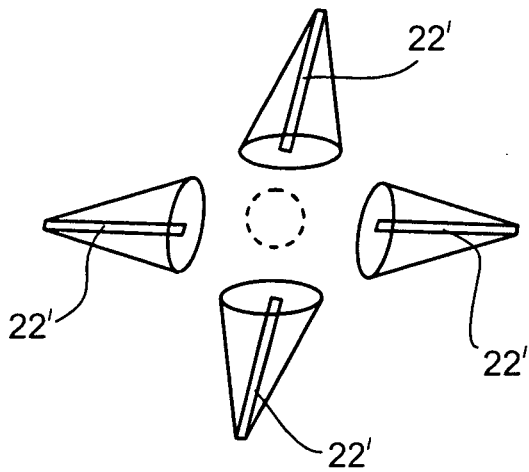
FIG. 6 is a presentation of a scanning protocol which can be effected with the detector of FIG. 5.

As is shown in FIG. 6, such a detector is typically used to measure radioactivity, point by point, by scanning over the surface of a radioactive object from a plurality of directions and distances. In the example shown, scans from four different directions are employed. It will be appreciated that if sufficient radioactivity records are collected from different angles and distances, and the orientation and position in space of detector 22' is simultaneously monitored and recorded during such scans, a three-dimensional model of a radioactive region can be reconstituted and its position in space determined. If two or more detectors are co-employed, as shown in the configuration of FIG. 10, the results may be collected faster.

Figure 7:
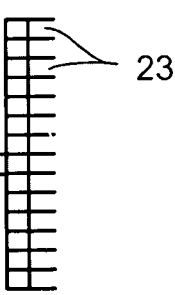
FIG. 7 is a simplified cross-sectional view of a spatially sensitive radioactive emission probe, e.g., a gamma camera, used to implement another embodiment of the present invention.
Figure 8:
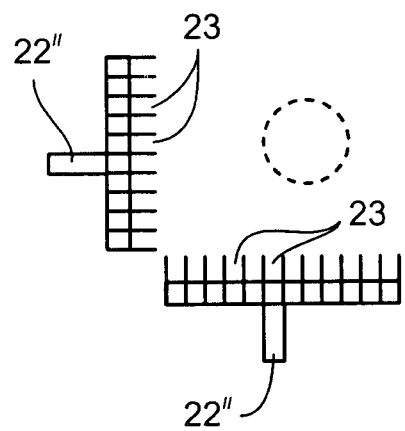
FIG. 8 is a presentation of a scanning protocol which can be effected with the detector of FIG. 7.

FIG. 7 shows another example of a radioactive emission probe, a spatially sensitive (pixellated) radioactive emission probe 22" (such as a gamma camera). Detector 22", in effect, includes an array of multitude narrow angle detector units 23. Such an arrangement is used in accordance with the teachings of the present invention to reduce the amount of measurements and angles necessary to acquire sufficient data so as to reconstitute a three-dimensional model of the radioactive object. Examples of spatially sensitive radioactive emission probes employed in a variety of contexts are disclosed in, for example, U.S. Pat. Nos. 4,019,057; 4,550,250; 4,831,262; and 5,521,373; which are incorporated by reference as if set forth herein. An additional example is the COMPTON detector (http://wvvw.ucl.ac.uk/MedPhys/posters/ giulia/giulia.htm). FIG. 8 shows a scan optionally made by spatially sensitive radioactive emission probe 22" (such as a gamma camera).

A radioactive emission detector of particular advantages for use in context of the present invention is the Compton gamma probe, since, in the Compton gamma probe, spatial resolution is independent of sensitivity and it appears possible to exceed the noise equivalent sensitivity of collimated imaging systems especially for systems with high spatial resolution. The Compton probe is a novel type of gamma-probe that makes use of the kinematics of Compton scattering to construct a source image without the aid of mechanical collimators. Compton imaging telescopes were first built in the 1970s for astronomical observations [V. Schoenfelder et al., Astrophysical Journal 217 (1977) 306]. The first medical imaging laboratory instrument was proposed in the early 1980s [M. Singh, Med. Phys. 10 (1983) 421]. The potential advantages of the Compton gamma probe include higher efficiency, 3-D imaging without detector motion, and more compact and lightweight system. In the Compton gamma probe, high-energy gamma rays are scattered from a first detector layer (or detectors array) into a second detector layer array. For each gamma, the deposited energy is measured in both detectors. Using a line drawn between these two detectors, the Compton scattering equation can be solved to determine the cone of possible direction about this axis on which the gamma ray must have entered the first detector. The intersection of cones from many events is then developed to locate gamma ray sources in the probe's field-of-view. Obviously only coincident events are considered, and the more accurately their energy can be determined, the less uncertainty there is in the spatial angle of the arrival cone. The probe's electronic system is combining coincidence measurements across many detectors and detectors layers with a very good energy resolution. The choice of the geometry and the material of the first layer detector plays a major role in the system imaging capability and depends on (i) material efficiency of single Compton events, in relation to other interactions; (ii) detector energy resolution; and (iii) detector position resolution. In particular, the overall angular resolution results from the combination of two components, related to the energy resolution and to the pixel volume of the detector.

Thus, as now afforded by the present invention, connecting a radioactive emission probe to a position tracking system, permits simultaneous radioactivity detecting and position tracking at the same time. This enables the accurate calculation of the shape, size and contour of the radiating object and its precise position in a system-of-coordinates.

The present invention thus provides a method for defining a position of a radioactivity emitting source in a system-of-coordinates. The method is effected by (a) providing a radioactive emission probe which is in communication with a position tracking system; and (b) monitoring radioactivity emitted from the radioactivity emitting source, while at the same time, monitoring the position of radioactive emission probe in the system-of-coordinates, thereby defining the image of the radioactivity emitting source in the system-of-coordinates.

It will be appreciated by one of skills in the art that the model produced by system 20 is projectable onto any of the other systems-of-coordinates, or alternatively, the system-of-coordinates defined by position tracking system 24 may be shared by other position tracking systems, as is further detailed hereinbelow, such that no such projection is required.

Thus, as is further shown in FIG. 1, system 20 of the present invention can be used for calculating a position of a radioactivity emitting source in a first system-of-coordinates 28 and further for projecting the image of the radioactivity emitting source onto a second system-of-coordinates 28'. The system includes radioactive emission probe 22, position tracking system 24 which is connected to and (or) communicating with radioactive emission probe 22, and data processor 26 which is designed and configured for (i) receiving data inputs from position tracking system 24 and from radioactive emission probe 22; (ii) constructing the image of the radioactivity emitting source in the first system-of-coordinates; and (iii) projecting the image of the radioactivity emitting source onto the second system-of-coordinates.

A method for calculating a position of a radioactivity emitting source in a first system-of-coordinates and for projecting the image of the radioactivity emitting source onto a second system-of-coordinates is also offered by the present invention. This method is effected by (a) providing a radioactive emission probe being in communication with a position tracking system; and (b) monitoring radioactivity being emitted from the radioactivity emitting source, while at the same time, monitoring the position of the radioactive emission probe in the first system-of-coordinates, thereby defining the image of the radioactivity emitting source in the first system-of-coordinates and projecting the image of the radioactivity emitting source onto the second system-of-coordinates.

It will be appreciated that the combination of a radioactive emission probe and a position tracking system connected thereto and (or) communicating therewith allows a suitable data processor to generate a two- or three-dimensional image of the radioactivity emitting source. An algorithm can be used to calculate image intensity based on, for example, a probability function which averages radiation counts and generates an image in which the shorter the time interval between radioactive counts, the brighter the image and vise versa, while down-compensating when a location is re-scanned. A free-hand scanning with a directional detector can be employed for this purpose.

In one embodiment, when scanning a body area with the detector, the detector is made to follow a three-dimensional surface, which defines the body curvature and in effect is used also as a position tracking pointer. This information can be used to define the position of the radioactive source with respect to the outer surface of the body, so as to create a three-dimensional map of both the radioactive source and of the body curvature. This approach can also be undertaken in open surgeries, such as open chest surgeries so as to provide the surgeon in real time with information concerning the functionality of a tissue.

The radioactive emission probe, which can be used in context of the present invention can be a beta emission detector, a gamma emission detector, a positron emission detector or any combination thereof. A detector that is sensitive to both beta and (or) positron and gamma emission can be used to improve localization by sensing for example gamma emission distant from the source and sensing beta or positrons emission closer to the source. A beta detector is dedicated for the detection of either electrons from sources such as $^{131}$Iodine, or positrons from sources such as $^{18}$Fluorine. A gamma detector can be designed as a single energy detector or as a detector that can distinguish between different types of energies, using the light intensity in the scintillator as a relative measure of the gamma energy. Also, the detector can be designed to utilize coincidence detection by using detectors facing one another (180 degrees) with the examined organ or tissue in-between. The radiation detector can have different collimators with different diameters. A large bore will be used for high sensitivity with lower resolution while a small bore collimator will have higher resolution at the expense of lower sensitivity.

Another possibility is to have a the collimator moving or rotating with the opening eccentric so that a different solid angle is exposed to the incoming photons at any one time, thus gathering the photons from overlapping volumes at different time intervals. The rest of the image processing is similar if the probe moves or if the collimator eccentric opening moves.

System 20 of the present invention can be used in concert with other medical devices, such as, but not limited to, any one of a variety of imaging modalities and (or) surgical instruments.

Structural imaging modalities, which provide anatomic, or structural maps of the body, are well known in the art. The main modalities that serve for two-(projectional or cross sectional) or three-(consecutive cross sectional) dimensional imaging are a planer X-ray imager, a fluoroscope, a computerized tomography scanner, a magnetic resonance imager an ultrasound imager, an impedance imager, and an optical camera.

Medical images taken of the human body are typically acquired or displayed in three main orientations (i) coronal orientation: in a cross section (plane), for example, across the shoulders, dividing the body into front and back halves; (ii) sagittal orientation: in a cross section (plane), for example, down the middle, dividing the body into left and right halves; and (iii) axial orientation: in a cross section (plane), perpendicular to the long axis of the body, dividing the body into upper and lower halves. Oblique views can also be acquired and displayed.

Various types of X-ray imaging are central to diagnosis of many types of cancer. Conventional X-ray imaging has evolved over the past 100 years, but the basic principal is still the same as in 1895, when first introduced. An X-ray source is turned on and X-rays are radiated through the body part of interest and onto a film cassette positioned under or behind the body part. The energy and wavelength of the X-rays allows them to pass through the body part and create the image of the internal structures like bones. As the X-rays pass through the hand, for instance, they are attenuated by the different density tissues they encounter. Bone attenuates a great deal more of the X-rays than the soft tissue surrounding it because of its grater density. It is these differences in absorption and the corresponding varying exposure level of the film that creates the images. In fact, X-ray imaging results in a projection of the integrated density of column-voxels defined by the X-rays as they pass through the body.

Fluoroscopy is a method based on the principals of film X-ray that is useful for detecting disorders and tumors in the upper gastrointestinal (GI) system (for example, the stomach and intestines). Fluoroscopic imaging yields a moving X-ray picture. The physician can watch the screen and see an image of the patient's body (for example the beating heart). Fluoroscopic technology improved greatly with the addition of television cameras and fluoroscopic "image intensifiers". Today, many conventional X-ray systems have the ability to switch back and forth between the radiographic and fluoroscopic modes. The latest X-ray systems have the ability to acquire the radiograph or fluoroscopic movie using digital acquisition.

Computed Tomography (CT) is based on the X-ray principal, where the film is replaced by a detector that measures the X-ray profile. Inside the covers of the CT scanner is a rotating frame which has an X-ray tube mounted on one side and the detector mounted on the opposite side. A fan beam of X-ray is created as the rotating frame spins the X-ray tube and detector around the patient. Each time the X-ray tube and detector make a 360° rotation, an image or "slice" has been acquired. This "slice" is collimated to a thickness between 1 mm and 10 mm using lead shutters in front of the X-ray tube and X-ray detector.

As the X-ray tube and detector make this 360° rotation, the detector takes numerous profiles of the attenuated X-ray beam. Typically, in one 360° lap, about 1,000 profiles are sampled. Each profile is subdivided spatially by the detectors and fed into about 700 individual channels. Each profile is then backwards reconstructed (or "back projected") by a dedicated computer into a two-dimensional image of the "slice" that was scanned.

The CT gantry and table have multiple microprocessors that control the rotation of the gantry, movement of the table (up/down and in/out), tilting of the gantry for angled images, and other functions such as turning the X-ray beam on an off. The CT contains a slip ring that allows electric power to be transferred from a stationary power source onto the continuously rotating gantry. The innovation of the power slip ring has created a renaissance in CT called spiral or helical scanning. These spiral CT scanners can now image entire anatomic regions like the lungs in a quick 20 to 30 second breath hold. Instead of acquiring a stack of individual slices which may be misaligned due to slight patient motion or breathing (and lung/abdomen motion) in between each slice acquisition, spiral CT acquires a volume of data with the patient anatomy all in one position. This volume data set can then be computer-reconstructed to provide three-dimensional models such as of complex blood vessels like the renal arteries or aorta. Spiral CT allows the acquisition of CT data that is perfectly suited for three-dimensional reconstruction.

MR Imaging is superior to CT in detecting soft tissue lesions such as tumors as it has excellent contrast resolution, meaning it can show subtle soft-tissue changes with exceptional clarity. Thus, MR is often the method of choice for diagnosing tumors and for searching for metastases. MR uses magnetic energy and radio waves to create single or consecutive cross-sectional images or "slices" of the human body. The main component of most MR systems is a large tube shaped or cylindrical magnet. Also, there are MR systems with a C-shaped magnet or other type of open designs. The strength of the MR systems magnetic field is measured in metric units called "Tesla". Most of the. cylindrical magnets have a strength between 0.5 and 1.5 Tesla and most of the open or C-shaped magnets have a magnetic strength between 0.01 and 0.35 Tesla.

Inside the MR system a magnetic field is created. Each total MR examination typically is comprised of a series of 2 to 6 sequences. An "MR sequence" is an acquisition of data that yields a specific image orientation and a specific type of image appearance or "contrast". During the examination, a radio signal is turned on and off, and subsequently the energy which is absorbed by different atoms in the body is echoed or reflected back out of the body. These echoes are continuously measured by "gradient coils" that are switched on and off to measure the MR signal reflecting back. In the rotating frame of reference, the net magnetization vector rotate from a longitudinal position a distance proportional to the time length of the radio frequency pulse. After a certain length of time, the net magnetization vector rotates 90 degrees and lies in the transverse or x-y plane. It is in this position that the net magnetization can be detected on MRI. The angle that the net magnetization vector rotates is commonly called the 'flip' or 'tip' angle. At angles greater than or less than 90 degrees there will still be a small component of the magnetization that will be in the x-y plane, and therefore be detected. Radio frequency coils are the "antenna" of the MRI system that broadcasts the RF signal to the patient and (or) receives the return signal. RF coils can be receive-only, in which case the body coil is used as a transmitter; or transmit and receive (transceiver). Surface coils are the simplest design of coil. They are simply a loop of wire, either circular or rectangular, that is placed over the region of interest.

A digital computer reconstructs these echoes into images of the body. A benefit of MRI is that it can easily acquire direct views of the body in almost any orientation, while CT scanners typically acquire cross-sectional images perpendicular or nearly perpendicular to the long body axis.

Ultrasound imaging is a versatile scanning technique that uses sound waves to create images of organs or anatomical structures in order to make a diagnosis. The ultrasound process involves placing a small device called a transducer, against the skin of the patient near the region of interest, for example, against the back to image the kidneys. The ultrasound transducer combines functions of emitting and receiving sound. This transducer produces a stream of inaudible, high frequency sound waves which penetrate into the body and echo off the organs inside. The transducer detects sound waves as they echo back from the internal structures and contours of the organs. Different tissues reflect these sound waves differently, causing a signature which can be measured and transformed into an image. These waves are received by the ultrasound machine and turned into live pictures with the use of computers and reconstruction software.

Ultrasound scanning has many uses, including: diagnosis of disease and structural abnormalities, helping to conduct other diagnostic procedures, such as needle biopsies etc.

There are limitations to some ultrasound techniques: good images may not be obtained in every case, and the scan may not produce as precise results as some other diagnostic imaging procedures. In addition, scan results may be affected by physical abnormalities, chronic disease, excessive movement, or incorrect transducer placement.

Both two-(cross sectional) and three-(consecutive cross-sectional) ultrasound imaging techniques are available nowadays. Worth mentioning is the Doppler three-dimensional ultrasound imaging.

In many cases imaging modalities either inherently include (e.g., fluoroscope, CT, MRI) and (or) are integrated with position-tracking-systems, which enable the use of such systems to reconstruct three-dimensional image models and provide their position in a system-of-coordinates.

It will be appreciated that, similar to the vision system, also an optical camera can be used to generate three-dimensional imagery date according to the present invention by imaging a body from a plurality (at least two) directions. This type of imaging is especially applicable in open chest surgeries or other open surgeries. Software for calculating a three-dimensional image from a pair of stereoscopic images is well known in the art.

Thus, as used herein and in the claims section that follows, the phrase "three-dimensional imaging modality" refers to any type of imaging equipment which includes software and hardware for generating a three-dimensional image. Such an equipment can generate a three-dimensional image by imaging successive cross-sections of a body, e.g., as if viewed from a single direction. Alternatively, such an equipment can generate a three-dimensional image by imaging successive cross-sections of a body, e.g., as if viewed from a single direction. Alternatively, such an equipment can generate a three-dimensional image by imaging a body from different angles or directions (typically two angles) and thereafter combining the data into a three-dimensional image.

In accordance with the present invention, a structural imaging probe, for example, an ultrasound probe, may be combined with a position tracking system, in a manner analogous to System 20 of radioactivity emission detector 22 and position tracking system 24 (FIG. 1). Similarly, a miniature MRI probe, for example, as taught by U.S. Pat. No. 5,572,132, to Pulyer, et al., entitled, "MRI probe for external imaging," whose disclosure is incorporated herein by reference, which teaches an MRI catheter for endoscopic imaging of tissue of the artery wall, rectum, urinal tract, intestine, esophagus, nasal passages, vagina and other biomedical applications, may be used.

Additionally, a structural imaging probe, for example, an ultrasound probe, may be combined with system 20 of radioactivity emission detector 22 and position tracking system 24 (FIG. 1), so as to have:

structural imaging;

functional imaging; and position tracking, simultaneously. Similarly, other structural imaging modalities, as known, may be combined with system 20 of FIG. 1.

Furthermore, the structural imaging modality may have an additional, dedicated position tracking system, or share position tracking system 24 of radioactivity emission detector 22.

Position tracking may also be accomplished by using imaging information from the structural imaging system. This may be accomplished by tracking relative changes from one image to another to determine relative motion.

Surgical instruments are also well known in the art and may use any one of a plurality of configurations in order to perform minimally-invasive surgical procedures. Examples include laser probes, cardiac and angioplastic catheters, endoscopic probes, biopsy needles, aspiration tubes or needles, resecting devices, ultrasonic probes, fiber optic scopes, laparoscopic prob s, thermal probes and suction/irrigation probes. Examples of such surgical instruments employed in a variety of medical cont xts are disclosed in, for example, U.S. Pat. Nos. 6,083,170; 6,063,022; 5,954,665; 5,840,025; 5,718,241; 5,713,946; 5,694,945; 5,568,809; 5,546,951; 5,480,422 5,391,199, 5,800,414; 5,843,017; 6,086,554; 5,766,234; 5,868,739; 5,911,719; 5,993,408; 6,007,497; 6,021,341; 6,066,151; 6,071,281; 6,083,166 and 5,746,738, which are incorporated by reference as if fully set forth herein.

For some applications, examples of which are provided in the list of patents above, surgical instruments are integrated with position-tracking-systems, which enable to monitor the position of such instruments while placed in and guided through the body of a treated patient.

According to a preferred embodiment of the present invention, the surgical instrument is equipped with an additional radioactive emission probe attached thereto or placed therein. This additional detector is used, according to preferred embodiments of the invention, to fine tune the location of radioactive emission from within the body, and in closer proximity to the radioactive source. Since the surgical tool is preferably in communication with a position-tracking system, the position of the additional detector can be monitored and its readouts used to fine tune the position of the radioactive source within the body. Thus, according to this aspect of the present invention, at least one extracorporeal detector and an intracorporeal detector are used in concert to determine the position of a radioactive source in the body in highest precision. The extracorporeal detector provides the general position of the source and is used for directing the surgical instrument thereto, whereas the intracorporeal detector is used for reassuring prior to application of treatment or retrieval of biopsy that indeed the source was correctly targeted at the highest precision.

While according to a presently preferred embodiment of the invention two detectors, one extracorporeal and one intracorporeal, are employed as described above, for some applications a single intracorporeal detector may be employed, which detector is attached to or integrated with a surgical instrument whose position is tracked.

The use of intracorporeal and extracorporeal detectors calls for careful choice of the radioactive isotope employed with the radiopharmaceutical. While the extracorporeal detector can be constructed with a suitable collimator for handling strong radiation, such as gamma radiation, the intracorporeal detector is miniature by nature and is limited in design and construction by the construction of the surgical instrument with which it is employed. Since collimators for high energy (80-511 KeV) gamma radiation are robust in nature, they are not readily engageable with miniature detectors. Electron (beta) and positron radiation are characterized by: (i) they highly absorbed by biological tissue as they are of lower energy and higher chemical reactivity; and (ii) they are readily collimated and focused by thin metal collimators. It is also possible to use low energy gamma radiation (10-30 KeV) for intracorporeal applications since the collimation of these gamma photons can be achieved with thin layers of Tantalum or Tungsten. As such, the radio pharmaceutical of choice is selected to emit both gamma and beta and (or) positron radiation, whereas the extracorporeal detector is set to detect the high energy gamma radiation, whereas the intracorporeal detector is set to detect the low energy gamma, beta and (or) positron radiation. Isotopes that emit both high energy gamma and (or) low energy gamma, beta and (or) positron radiation and which can be used per se or as a part of a compound as radiopharmaceuticals include, without limitation, $^{18}$F, $^{111}$In and $^{123}$I in radiopharmaceuticals, such as, but not limited to, 2-[$^{18}$F]fluoro-2-deoxy-D-glucose ($^{18}$FDG), $^{111}$In-Pentetreotide ([$^{111}$In-DTPA-D-Phe$^{1}$]-octreotide), L-3-[$^{123}$I]-Iodo-alpha-methyl-tyrosine (IMT), O-(2-[$^{18}$F]fluoroethyl)-L-tyrosine (L-[$^{18}$F]FET), $^{111}$In-Capromab Pendetide (CYT-356, Prostascint) and $^{111}$In-Satumomab Pendetide (Oncoscint).

Figure 11:
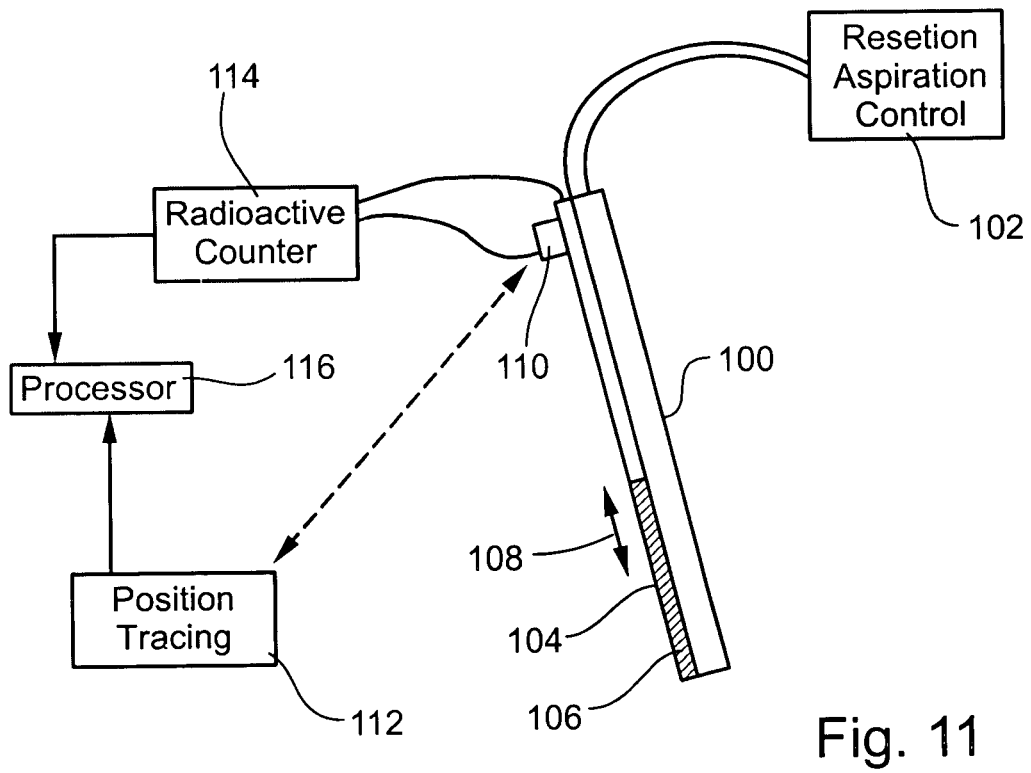
FIG. 11 is a schematic diagram of a surgical instrument and accompanying system elements according to the teachings of the present invention.

FIG. 11 illustrates a system in accordance with this aspect of the present invention. A surgical instrument 100 is shown connected to a resection/aspiration control element 102 as well known in the art. Surgical instrument 100 includes a radioactive emission probe 104, which has a collimator 106 for collimating low energy gamma, beta and (or) positron radiation. In some embodiments, as indicated by arrow 108, detector 104 may be translated within instrument 100. A position tracking system having one element thereof 110 attached to instrument 100 and another element thereof 112 at a fixed location serves to monitor the position of instrument 100 at all times in two, three and up to six degrees of freedom. Radioactive emission probe 104 communicates with a counter 114 for counting low energy gamma, beta and (or) positron radiation. All the data is communicated to, and processed by, a processor 116. The 2D or 3D data may be projected and displayed along with 2D or 3D imaging data derived from an imaging modality using a shared presentation device as described elsewhere herein. A real or virtual image of the surgical instrument itself may also be co-displayed. Examples of commercially available radiation emission detectors that can fit inside, for example, a biopsy needle include scintillating plastic optical fibers like S101 and S104, manufactured by PPLASTIFO or an optical fiber communicating with a scintillator (either detector paint or scintillation crystal) at the fiber edge. The level of detected radiation can be reported visually or by an audio signal, as is well known in the art.

Thus, a surgical instrument equipped with a radiation emission detector and which is connected to and (or) communicating with a position tracking system forms one embodiment of this aspect of the present invention. Such a design acting in concert with either conventional imaging modalities and (or) extracorporeal radiation emission detectors form other embodiments of this aspect of the invention. In all cases, a surgical instrument equipped with a radiation emission detector and which is connected to and (or) communicating with a position tracking system serves for in situ fine tuning of a radioactive source in the body.

It will be appreciated that in some minimally-invasive procedures even the position of the patient him or herself is monitored via a position tracking system, using, for example, electronic or physical fiducial markers attached at certain locations to the patient's body.

Thus, as is further detailed hereinbelow, by projecting the three-dimensional data and positions received from any of the above mentioned devices into a common system of coordinates, or alternatively, employing a common position tracking system for all of these devices, one can integrate the data into a far superior and comprehensive presentation.

Figure 9:
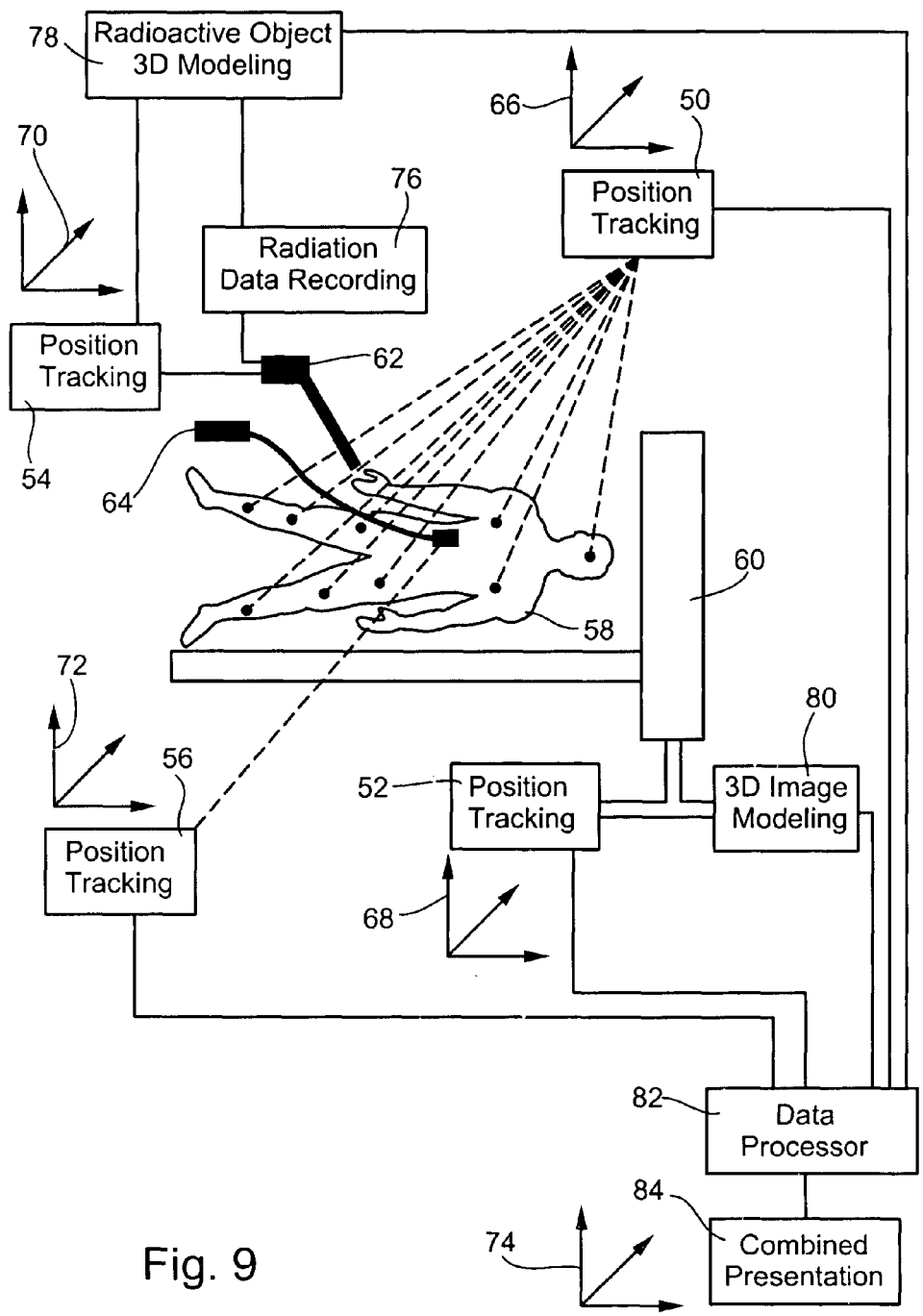
FIG. 9 demonstrates a system in accordance with the teachings of the present invention which employs four position tracking systems for co-tracking the positions of a patient, a radioactive emission probe, an imaging modality and a surgical instrument.

An example to this desired outcome is shown in FIG. 9. In the embodiment shown, four independent position tracking systems 50, 52, 54 and 56 are used to track the positions of a patient 58, an imaging modality 60, a radioactive emission probe 62 and a surgical instrument 64 in four independent systems-of-coordinates 66, 68, 70 and 72, respectively. If the patient is still, no tracking of the patient's position is required.

It will be appreciated that any subset or all of the position tracking systems employed may be integrated into one or more common position tracking systems, and (or) that any subset or all of the position tracking systems employed may share one or more systems-of-coordinates, and further that any positional data obtained by any of the position tracking systems described in any of the systems-of coordinates may be projected to any other system of coordinates or to an independent (fifth) system of coordinates 74. In one preferred embodiment, applicable for applications at the torso of the patient, the system of coordinates is a dynamic system of coordinates which takes into account the chest breathing movements of the patient during the procedure.

As indicated at 76, the raw data collected by detector 62 is recorded and, as indicated at 78, the position and the radioactive data records are used to generate a three-dimensional model of a radiopharmaceutical uptake portion of a body component of the patient.

Similarly, as indicated at 80, the imagery data collected by imaging modality 60 is recorded and the position and the imagery data records are used to generate a three-dimensional model of the imaged body component of the patient.

All the data collected is then fed into a data processor 82 which processes the data and, as indicated at 84, generates a combined or superimposed presentation of the radioactive data and the imagery data, which is in positional context with patient 58 and surgical instrument 64.

Instrument 64, which by itself can he presented in context of the combined presentation, may then be used to perform the procedure most accurately. Processor 82 may be a single entity or may include a plurality of data processing stations which directly communicate with, or even integral to, any one or more of the devices described.

Additionally or alternatively, a structural imaging probe, for example, an ultrasound probe, or another structural probe, as known, may be incorporated with the surgical instrument.

The present invention provides a major advantage over prior art designs because it positionally integrates data pertaining to a body portion as retrieved by two independent imaging techniques, conventional imaging and radioactive imaging, to thereby provide a surgeon with the ability the fine point the portion of the body to be sampled or treated.

It will be appreciated that subsets of the devices described in FIG. 9 may be used as stand-alone systems. For example, a combination of detector 62 with its position-tracking system and instrument 64 with its position-tracking-system may in some instances be sufficient to perform intrabody procedures. For mere diagnostic purposes, without biopsy, a combination of detector 62 position-tracking-system and modality 60 position-tracking-system are sufficient.

Figure 12:
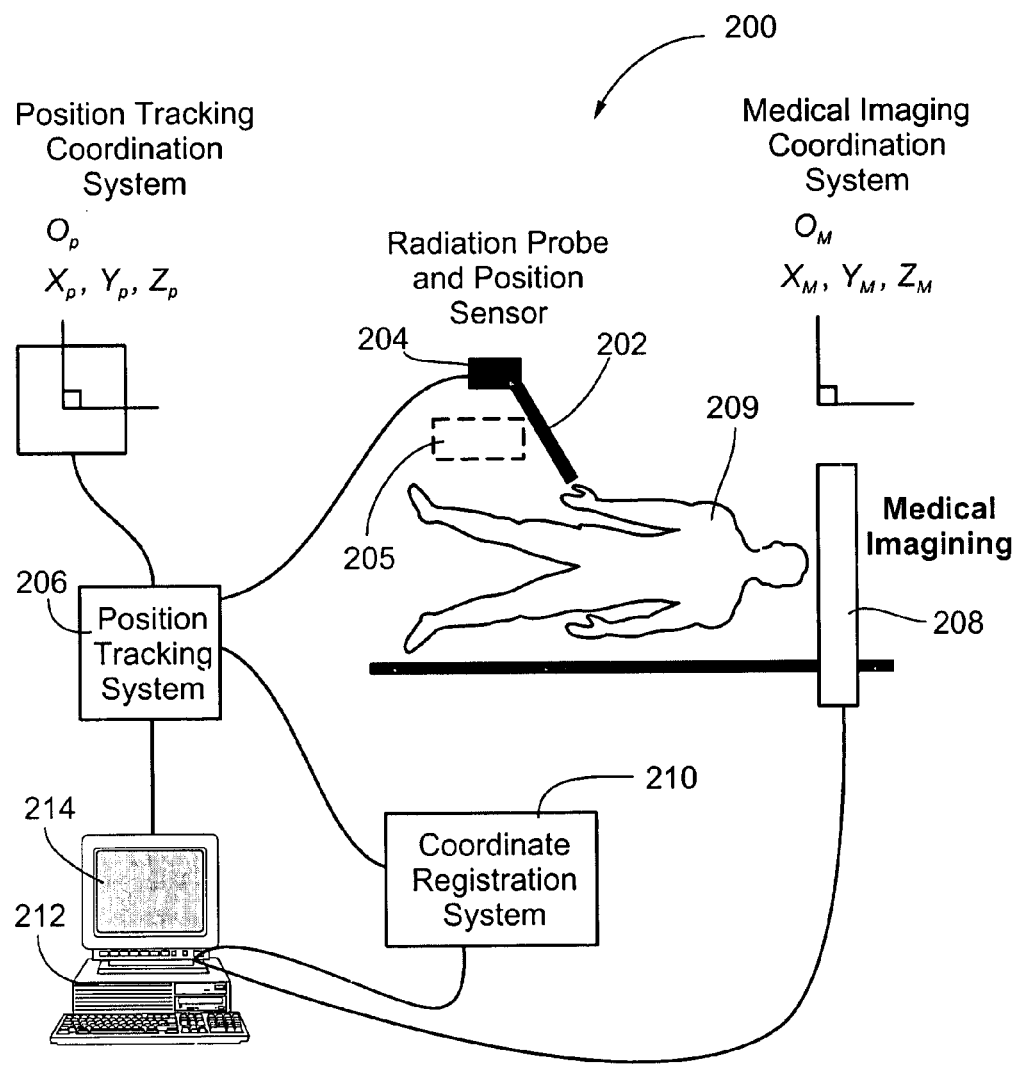
FIG. 12 is a simplified pictorial illustration of an imaging system constructed and operative in accordance with a preferred embodiment of the present invention, including a radiation probe and position sensor, position tracking system, medical imaging system and coordinate registration system.

Reference is now made to FIG. 12, which illustrates an imaging system 200 constructed and operative in accordance with a preferred embodiment of the present invention. Imaging system 200 preferably includes a radiation probe 202, such as the narrow angle radioactive emission probe 22' described hereinabove with reference to FIGS. 5 and 10.

A position sensor 204 is provided for sensing the position of radiation probe 202. Position sensor 204 may be physically attached to radiation probe 202, or may be distanced therefrom. Position sensor 204 transmits the sensed position data to a position tracking system 206 Position tracking system 206 may be a system like position tracking system 24, described hereinabove with reference to FIG. 1, and position sensor 204 may be any kind of sensor applicable for such position tracking systems.

Another method which can be used to locate the source of radiation emission is by using a small hand held gamma camera 205 (such as the DigiRad 2020 tc Imager™, 9350 Trade Place, San Diego, Calif. 92126-6334, USA), attached to position sensor 204.

Position tracking system 206 enables radiation probe 202 to freely scan back and forth in two- or three-dimensions over the area of interest of the patient, preferably incrementing a short distance between each scan pass. Position tracking system 206 tracks the position of radiation probe 202 with respect to a position tracking coordinate system, such as $X_p$, $Y_p$ and $Z_p$, with an origin $O_p$.

Imaging system 200 also includes a medical imaging system 208, such as, but not limited to, computed or computerized tomography (CT), magnetic resonance imaging (MRI), ultrasound imaging, positron emission tomography (PET) and single photon emission computed tomography (SPECT), for example. Medical imaging system 208 provides images of a patient 209 with respect to a medical imaging coordinate system, such as $X_m$, $Y_m$ and $Z_m$, with an origin $O_m$.

Imaging system 200 also includes a coordinate registration system 210, such as that described in commonly owned, now abandoned, U.S. patent application No. 09/610,490, entitled, "method for registering coordinate systems," the disclosure of which is incorporated herein by reference. Coordinate registration system 210 is adapted to register the coordinates of the position tracking coordinate system with those of the medical imaging coordinate system.

Position tracking system 206, medical imaging system 208 and coordinate registration system 210 are preferably in wired or wireless communication with a processing unit 212 (also referred to as a data processor 212).

In operation of imaging system 200, after administration of a radiopharmaceutical to patient 209, a clinician/physician/surgeon (not shown) may move or scan radiation probe 202 about a target area under examination. A physiological activity map of the target area is obtained by measuring the radiation count rate with radiation probe 202, and by correlating the count rate with the count rate direction with position tracking system 206, which follows the motion of the moving or scanning radiation probe 202.

Figure 13:
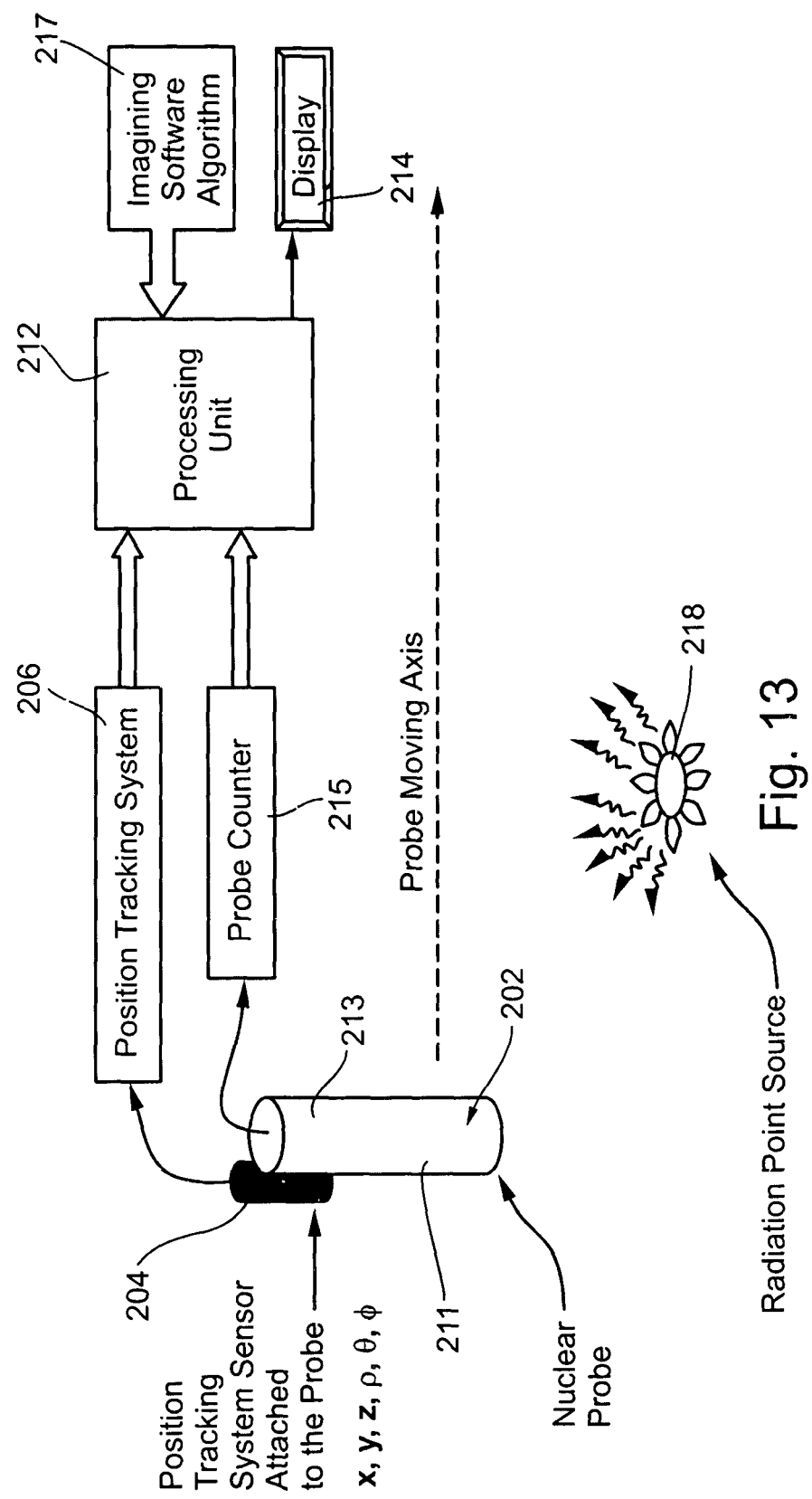
FIG. 13 is a simplified pictorial illustration of a single dimension image formation with a nuclear radiation probe attached to a position tracking system of the system of FIG. 12, in accordance with a preferred embodiment of the present invention.

Reference is now made to FIG. 13, which illustrates image formation with radiation probe 202, in accordance with a preferred embodiment of the present invention. For the purposes of simplicity, the example shown in FIG. 13 is for a single dimension image formation, but it is readily understood that the same principles hold true for any other dimensional image formation.

In one example of carrying out the invention, radiation probe 202 may be a gamma ray detector probe that comprises a collimator 211 and radiation detector 213. Gamma rays are projected through the probe collimator 211 onto radiation detector 213, which produces electronic signals in accordance with the radiation detected Radiation probe 202 sends pulses to a probe counter 215 which may include a pulse height analyzer circuit (not shown). The pulse height analyzer circuit analyzes the electronic signals produced by radiation detector 213. If the electronic signals are within a selected energy window, the level of radiation, i.e., number of radiation counts, is counted by probe counter 215.

Examples of suitable radiation detectors include a solid state detector (SSD) (CdZnTe, CdTe, HgI, Si, Ge, and the like), a scintillation detector (NaI(Tl), LSO, GSO, CsI, CaF, and the like), a gas detector, or a scintillating fiber detector (S101, S104, and the like).

The position sensor 204 associated with the radiation probe 202 senses the position of radiation probe 202, and position tracking system 206 calculates and monitors the motion of radiation probe 202 with respect to the position tracking coordinate system. The motion is calculated and monitored in two, three and up to six dimensions—the linear directions of the X, Y and Z axes as well as rotations about the X, Y and Z axes, i.e., rotational angles ρ, θ and φ, respectively.

Examples of suitable position tracking systems include a measurement mechanical arm (FaroArm, http://www.faro.com/products/faroarm.asp), optical tracking systems (Northern Digital Inc., Ontario, Canada NDI-POLARIS passive or active systems), magnetic tracking systems (NDI-AURORA), infared tracking systems (E-PEN system, http://www.e-pen.com), and ultrasonic tracking systems (E-PEN system), for example.

Processing unit 212 combines the radiation probe count rate from probe counter 215 together with the positional information from position tracking system 206, and uses an imaging software algorithm 217 to form a two-dimensional or three-dimensional radiotracer-spread image of the target area inside the patient's body. The spatial probe positions together with the spatial count rates may be stored in memory or displayed on a computer monitor 214 as a pattern of marks corresponding to the spatial and count rate position.

Figure 14:
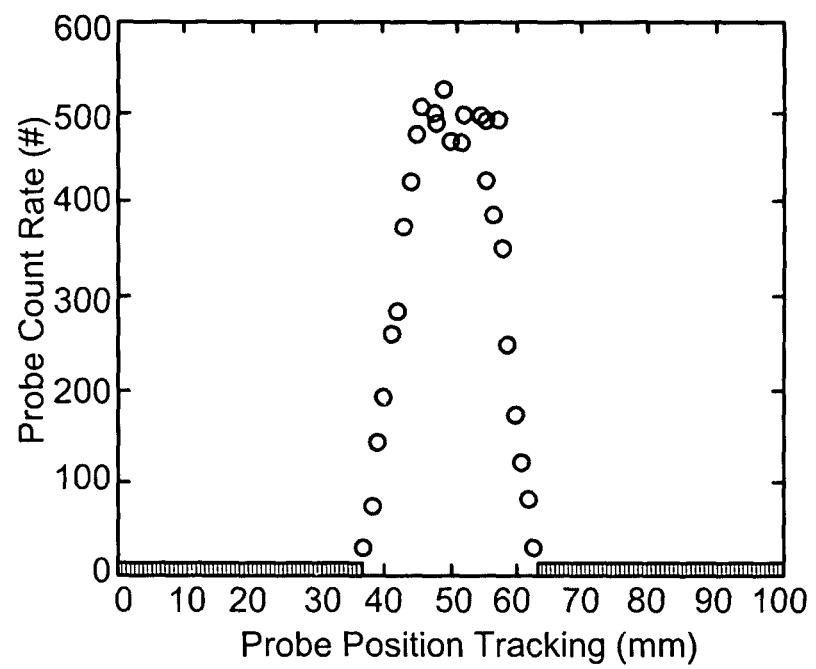
FIG. 14 is a simplified pictorial plot of detecting a radiation point source with the nuclear radiation probe of the system of FIG. 12, without further processing, in accordance with a preferred embodiment of the present invention.

An example of such a pattern is shown in FIG. 14, which illustrates a single-dimensional, unprocessed simulation of a radiation point source 218 (FIG. 13), 30 mm deep inside the human body, detected by using a 10 mm nuclear radiation probe 202 coupled to position tracking system 206. The graph of FIG. 14 indicates to a physician that there is a peak count rate of about 500 in the probe position of about 50 mm.

In one embodiment of the invention, the imaging software algorithm 217 employs an averaging process to refine the curve of FIG. 14. This averaging process will now be described with reference to FIG. 15.

Probe counter 215 feeds probe count rate information N(Xc, Yc, Zc, ρ, θ, φ) to processing unit 212 (step 301). Position sensor 204 feeds probe position information (Xc, Yc, Zc, ρ, θ, φ) to processing unit 212 (step 302). Probe parameters (such as its physical size, dx, dy, dz) are also input into processing unit 212 (step 303).

Processing unit 212 then finds all the voxels (i.e., volume pixels) that represent the probe volume in the processing unit memory (step 304), i.e., Xc+dx, Yc+dy, Zc+dz. Processing unit 212 calculates the number of times that the calculation process has been done in each voxel from the beginning of the image formation (step 305), i.e., M(Xc+dx, Yc+dy, Zc+dz). Processing unit 212 then calculates the new average count rate values in each voxel (step 306), in accordance with the formula:

$$N(Xc + dx, Yc + dy, Zc + dz) = [N(Xc + dx, Yc + dy, Zc + dz) + N(Xc, Yc, Zc, \rho, \theta, \varphi)] / [M(Xc + dx, Yc + dy, Zc + dz) + 1]$$

Processing unit 212 then corrects the display image that represents the perceived voxels at N(Xc+dx, Yc+dy, Zc+dz) (step 307). The algorithm then repeats itself for the next probe position (step 308).

Figure 15:
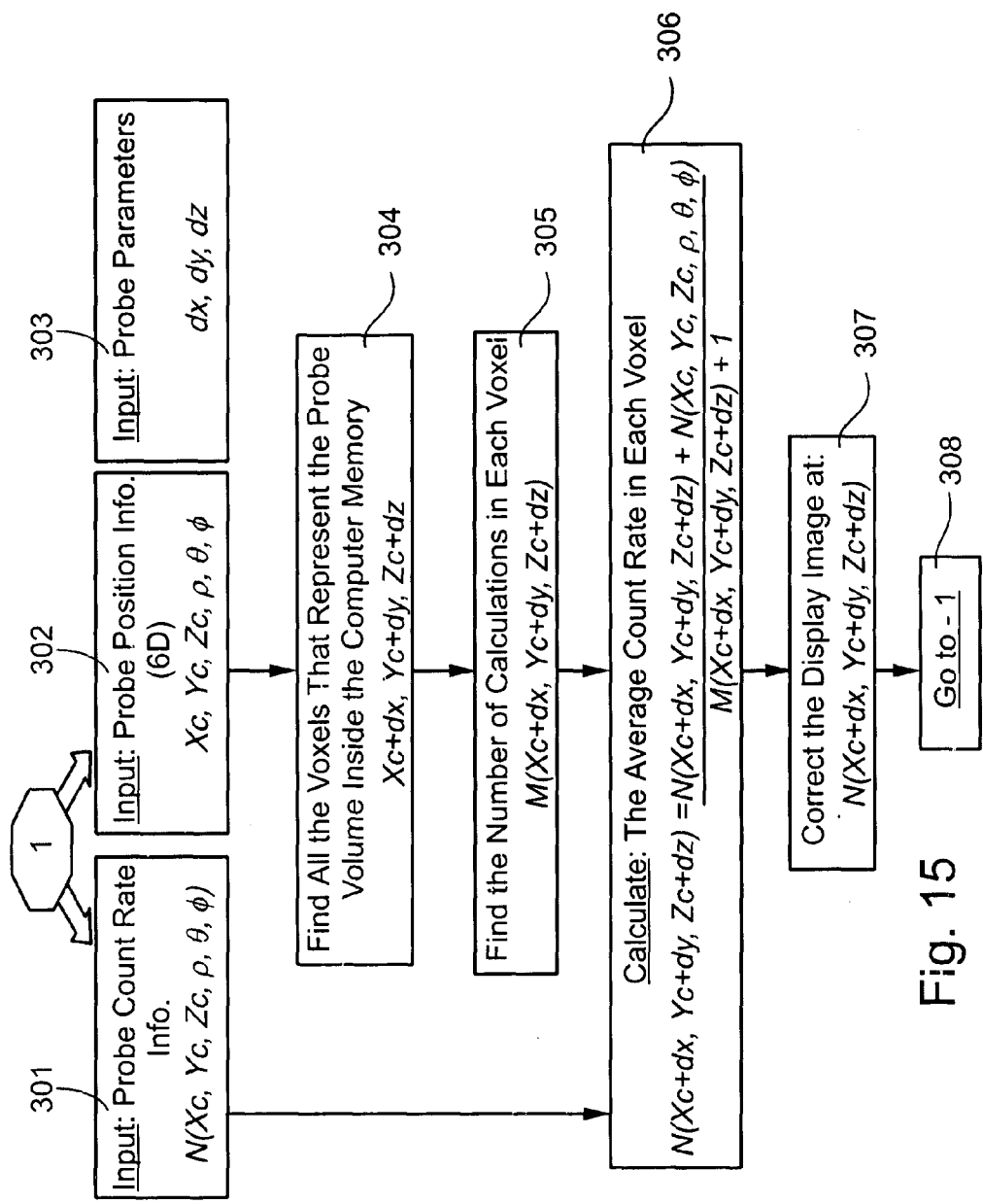
FIG. 15 is a simplified flow chart of an averaging algorithm used in the imaging system of FIG. 12, in accordance with a preferred embodiment of the present invention.
Figure 16:
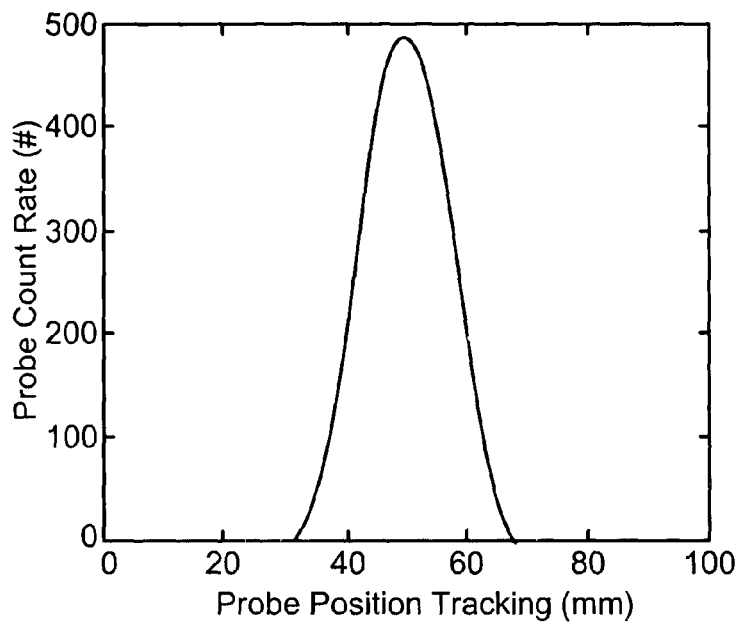
FIG. 16 is a simplified pictorial plot of detecting a radiation point source with the nuclear radiation probe of the system of FIG. 12, with averaging processing, in accordance with a preferred embodiment of the present invention.

The resulting graph of the averaging algorithm of FIG. 15, as applied to the example of FIG. 14, is shown in FIG. 16.

Figure 17:
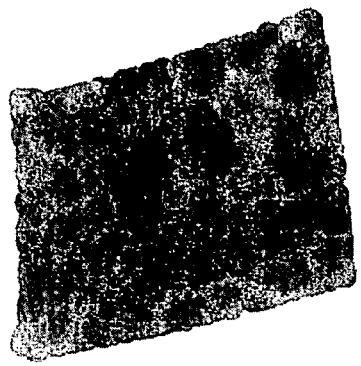
FIGS. 17 and 18 are simplified pictorial illustrations of hot cross and hot bar phantom images, respectively, of images produced by a gamma radiation probe of the system of FIG. 12.
Figure 18:
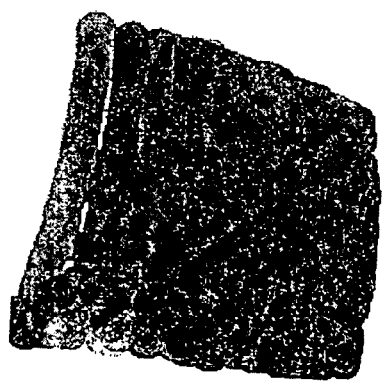

FIGS. 17 and 18 respectively show examples of a hot cross phantom image and a hot 4.77 mm bar phantom image, produced by a gamma radiation probe coupled with position tracking system 206 and the averaging algorithm of FIG. 15. The probe images were made by using a probe, EG&G Ortec NaI(Tl) model 905-1 (thickness=1", diameter=1") connected to a ScintiPack model 296. The position tracking system used was the Ascension miniBIRD, commercially available from Ascension Technology Corporation, P.O. Box 527, Burlington, Vt. 05402 USA (http://vww.ascension-tech.com/graphic.htm). The magnetic tracking and location systems of Ascension Technology Corporation use DC magnetic fields to overcome blocking and distortion from nearby conductive metals. Signals pass through the human body without attenuation.

In another embodiment of the invention, the imaging software algorithm 217 may employ a minimizing process to refine the curve of FIG. 14 as is now described with reference to FIG. 19.

Probe counter 215 feeds probe count rate information N(Xc, Yc, Zc, ρ, θ, φ) to processing unit 212 (step 401). Position sensor 204 feeds probe position information (Xc, Yc, Zc, ρ, θ, φ) to processing unit 212 (step 402). Probe parameters (such as its physical size, dx, dy, dz) are also input into processing unit 212 (step 403).

Processing unit 212 then finds all the voxels that represent the probe volume in the processing unit memory (step 404), i.e., Xc+dx, Yc+dy, Zc+dz. From the voxels that represent the probe volume in the processing unit memory, processing unit 212 finds those that have a higher count rate value N(Xc+dx, Yc+dy, Zc+dz) than the inputted probe count rate N(Xc, Yc, Zc, ρ, θ, φ) (step 405). Processing unit 212 then changes the higher count rate voxels to that of inputted probe count rate N(Xc, Yc, Zc, ρ, θ, φ) (step 406), and corrects the display image at the higher count rate voxels N(Xc+dx, Yc+dy, Zc+dz) (step 407). The algorithm then repeats itself for the next probe position (step 408).

Figure 19:
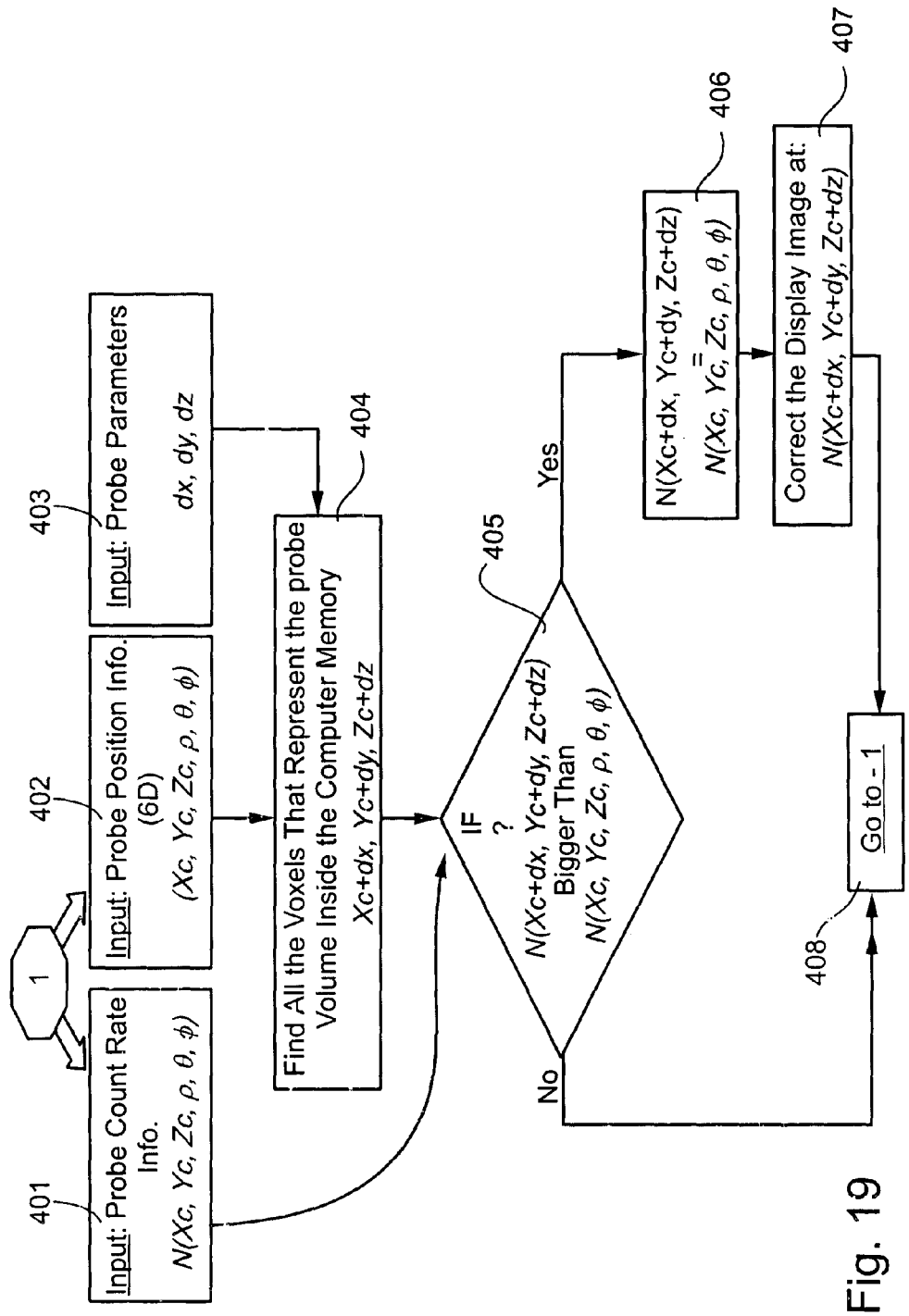
FIG. 19 is a simplified flow chart of a minimizing algorithm used in the imaging system of FIG. 12, in accordance with a preferred embodiment of the present invention.
Figure 20:
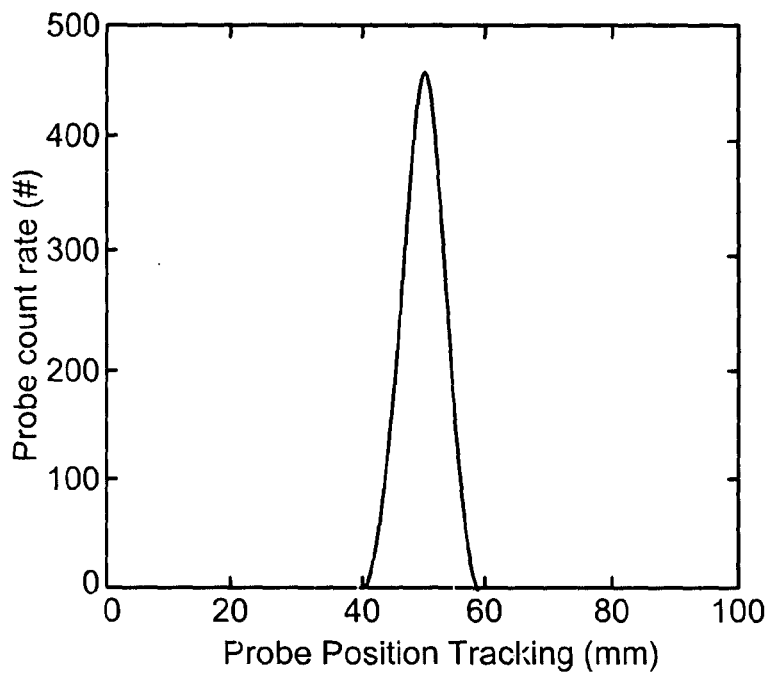
FIG. 20 is a simplified pictorial plot of detecting a radiation point source with the nuclear radiation probe of the system of FIG. 12, with minimizing processing, in accordance with a preferred embodiment of the present invention.

The resulting graph of the minimizing algorithm of FIG. 19, as applied to the example of FIG. 14, is shown in FIG. 20.

Figure 21:
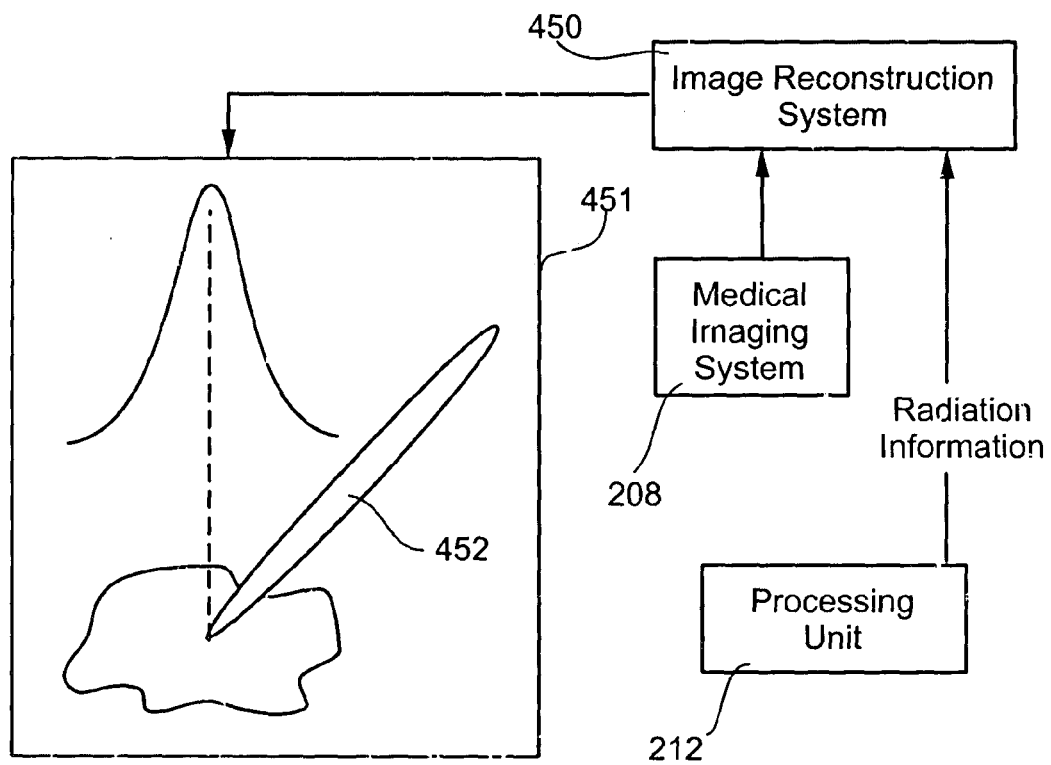
FIG. 21 is a simplified pictorial illustration of an image reconstruction system constructed and operative in accordance with a preferred embodiment of the present invention, which produces a combined image made up of medical images, the position of the peak radiation location and the location of a therapeutic instrument.

Reference is now made to FIG. 21, which illustrates an image reconstruction system 450, constructed and operative in accordance with a preferred embodiment of the present invention. Image reconstruction system 450 produces a combined image 451 made up of the images coming from the medical imaging system 208 with the position of the peak radiation location (and its uncertainty area) from processing unit 212, together with the location of a therapeutic instrument 452, such as a biopsy needle The combined image 451 allows the. physician to better assess the relative position of therapeutic instrument 452 in relation to the anatomical image (from medical imaging system 208) and the position of the radioactive area as inferred by the radiation detection algorithm.

In accordance with preferred embodiments of the present invention, image acquisition and reconstruction algorithms are provided, based on image acquisition with wide-aperture collimation and image reconstruction, which includes deconvolution. The overall algorithms are herethereto referred to as wide-aperture collimation—deconvolution algorithms.

In essence, the wide-aperture collimation—deconvolution algorithms enable one to obtain a high-efficiency, high resolution image of a radioactivity emitting source, by scanning the radioactivity emitting source with a probe of a wide-aperture collimator, and at the same time, monitoring the position of the radioactive emission probe, at very fine time intervals, to obtain the equivalence of fine-aperture collimation. The blurring effect of the wide aperture is then corrected mathematically.

The wide-aperture collimation—deconvolution algorithms are described hereinbelow, in conjunction with FIGS. 27A-27I, and FIG. 22. Experimental results, showing images produced by the wide-aperture collimation—deconvolution algorithms of the present invention, in comparison to a conventional gamma camera are seen in FIGS. 23A-26B, and FIG. 36, hereinbelow.

It will be appreciated that the wide-apeture collimation—deconvolution algorithms of the present invention apply also to systems on fixed gantries, such as gamma camera and SPECT.

Referring further to the drawings, FIGS. 27A-27I describe wide-aperture collimation—deconvolution algorithms, in accordance with preferred embodiments of the present invention. The wide-aperture collimation—deconvolution algorithms are designed for estimating the distribution of radiation sources in a control volume, thus constructing an image of the radiation sources in the control volume. For simplicity, it is assumed that the radiation sources comprise dot sources that radiate uniformly in all directions, are localized, and are smoothly distributed in the control volume.

Consider a single-pixel, wide-bore-collimator probe 707, seen in FIG. 27H, formed for example, as a lead tube collimator 708, having a length, $L_{collimator}$ of about 20 mm and a radiation detector 706, for example, a solid state CdZnTl crystal, at its base, with a diameter, $D_{detector}$ of about 10 mm, so that the ratio of $L_{collimator}$ to $D_{detector}$ is about 2. An angular opening δ of wide-bore-collimator probe 707 may be about 40 degrees; wide-bore-collimator probe 707 is sensitive to any incident photons within the confining of about a 40-degree angular opening. It will be appreciated that single-pixel, wide-bore-collimator probes of other dimensions and ratios of $L_{collimator}$ to $D_{detector}$ are similarly possible. For example, the ratio of $L_{collimator}$ to $D_{detector}$ may be about 1, or about 3.

By contrast, as seen in FIG. 27I, conventional gamma cameras have a multi-pixel small-aperture collimation probe, wherein a collimator—pixel arrangement 709 is about 2 mm in diameter and 40 mm in length, so that the ratio of $L_{collimator}$ to $D_{detector}$ is about 20. An angular opening ε of the small-aperture collimation probe is very small. In consequence, wide-bore-collimator probe 707 may be about 30 times more sensitive than the small-aperture collimation probe of collimator—pixel arrangement 709.

Yet, there are disadvantages to wide-bore-collimator probe 707:
1. a single-pixel probe does not lend itself to the generation of an image; and
2. a wide aperture blurs the information regarding the direction from which the radiation comes.

With regard to the first point, the generation of an image, as wide-bore-collimator probe 707 is moved in space, while its position and angular orientation are accurately tracked, at very short time intervals, for example, of about 100 or 200 ms, or any other short time interval, a one-, two-, or three-dimensional image of counting rate as a function of position can be obtained, by data processing.

More specifically, knowing the position and orientation of probe 707 at each time interval and the photon count rate at that position and orientation can be used to reconstruct the radiation density of an unknown object, even in three dimensions.

With regard to the second point, the blurring effect of the wide-angle aperture, while it is known that the information is blurred, or convolved, by the wide-aperture collimator, a deconvolution process may be used to obtain dependable results. Moreover, the convolving function for a wide aperture depends only on the geometry of the collimator and may be expressed as a set of linear equations that can be readily solved.

Thus, in accordance with the present invention, a wide-bore collimator probe, having a position tracking system, operating at very short time intervals, and connected to a data processor for wide-aperture collimation—deconvolution algorithms, can be used for the construction of an image of radiation density in one-, two-, or three-dimensions, with high degree of accuracy.

It will be appreciated that similar analyses may be employed for wide aperture probes having non-circular collimators. For example, the wide-aperture probe may have a rectangular collimator of a single cell or of a coarse grid of cells. Additionally, the collimator may be a wide-angle collimator. A corresponding deconvolution function may be used by the data processor.

Figure 27A:
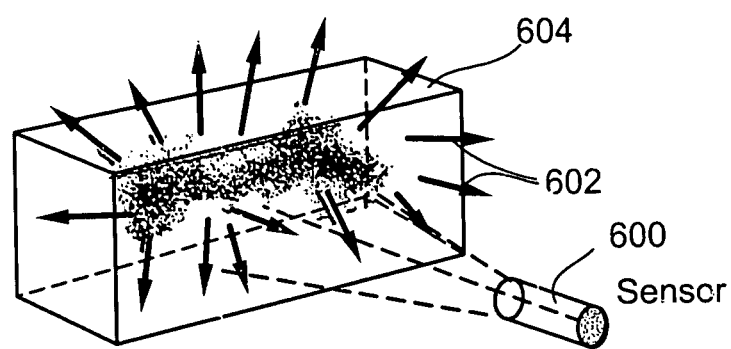
Figure 27B:
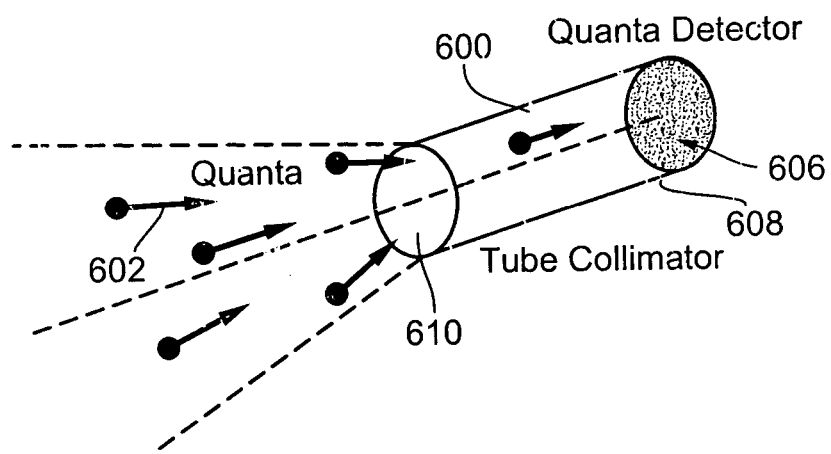

Reference is now made to FIGS. 27A and 27B, which illustrate a radiation sensor 600, preferably generally shaped as a tube collimator. Radiation quanta 602 are registered by the radiation sensor 600, as described hereinabove, thereby providing the average number of quanta per unit time. The radiation sensor 600 may be moved around a volume of interest 604, preferably, with six-dimensional freedom of motion, and six dimensional monitoring. However, it will be appreciated that a more limited motion and corresponding monitoring, for example, only in the X and ρ directions is possible. The position of the sensor 600 and its direction (as well as the position of the investigated volume 604) are assumed to be known at any given moment (FIG. 27A).

The tube collimator is preferably provided with a plane circular detector 606 of radiation quanta. The quanta detector 606 is preferably disposed on a rear end 608 of the tube and radiation quanta can reach the detector 606 only through an open front end 610 of the tube (FIG. 27B)

Figure 27C:
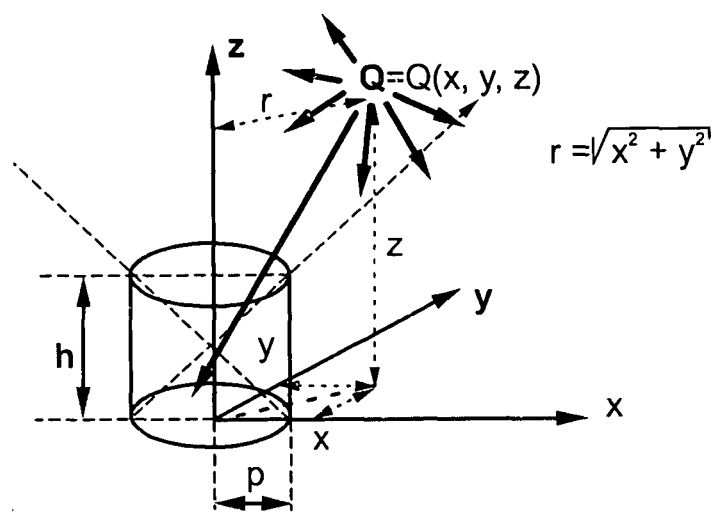

Reference is now made to FIG. 27C, which illustrates a system of coordinates (x, y, z) with the origin O in the center of the radiation sensor 600, the (x, y) plane being the plane of the detector, and the z axis being in the center of the collimator tube. The geometry parameters of the collimator tube—height h and radius ρ—are known.

From the rotational symmetry of the tube, it is clear that having a radiation source Q=Q(x, y, z) with the total intensity I uniformly radiating in all directions, the portion of the intensity registered by the quanta detector 606 of the radiation sensor 600 is determined only by the distance r from Q to the axis of the collimator (axis z) and the distance z from Q to the (x, y) plane. In other words, there is a function $\Phi(r, z)$, which is defined only by the collimator parameters ρ and h (corresponding expressions from ρ, h, r and z may be easily written in explicit form), such that the intensity of the radiation spot Q=Q(x, y, z)=Q(r, z) registered by detector 606 is proportional to $\Phi(r, z)$ and to the total intensity I of the radiation spot.

Figure 27D:
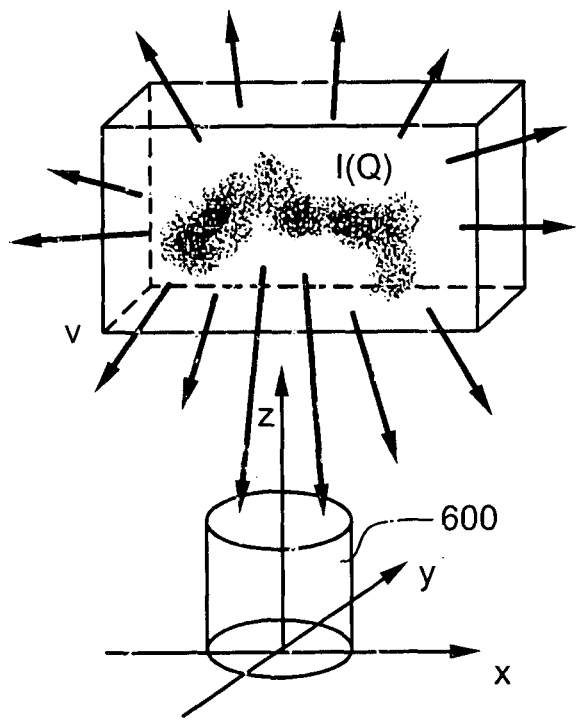

Reference is now made to FIG. 27D. It follows from the foregoing discussion, that if instead of one radiation spot there is a radiation distribution I(Q)=I(Q(r, z)) in a volume V, then the radiation intensity, registered by radiation sensor 600, is proportional (with some constant not depending on the radiation distribution and the sensor position) to the following integral:

$$\int_V I(Q(r,z))\Phi(r,z)\,dQ \tag{1}$$

An algorithm for estimating the intensity distribution I(Q) from the values obtained in the measurement scheme of Equation (1) is now discussed. For the sake of simplicity, the first case is discussed with reference to FIG. 27E for a two-dimensional problem, wherein intensities I(Q) are distributed in some 2-dimensional plane. The 3D problem is a direct generalization of the corresponding 2D problem, as is explained hereinbelow.

Figure 27E:
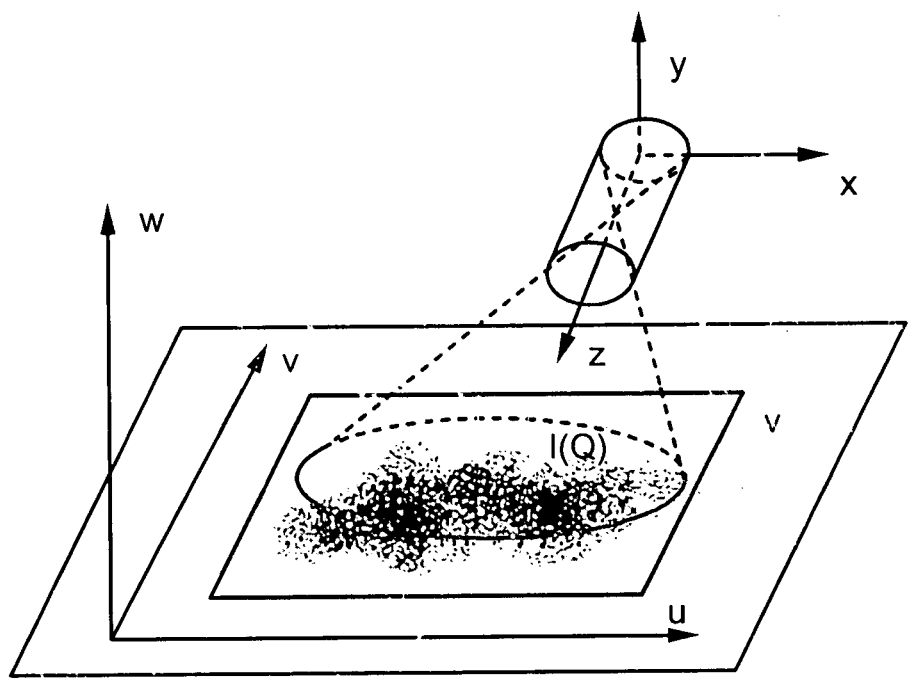

As seen in FIG. 27E, the radiation sources are distributed in a rectangular region V in a plane. Two systems of coordinates are considered. The first one is the sensor coordinate system (x, y, z) corresponding to the sensor 600. The second one is the radiation source coordinate system (u, v, w) corresponding to the radiation sources plane (u, v).

It is assumed that at each discrete time increment, the position of the origin of (x, y, z) system and the direction of the z-axis unit vector in (u, v, w) coordinates are known. In other words, the position and direction of the moving sensor in the (u, v, w) coordinate system is known, and the (u, v, w) coordinate system is assumed to be motionless.

The radiation sources are considered to be distributed in accordance with the distribution function I(Q) ) in some bounded, given rectangle V on the plane (u, v). I(Q)=I(u, v) is the unknown and sought-for radiation (or radiation intensity) distribution function defined in V.

To regularize the problem of estimation of the radiation distribution function I(Q), the function I(Q) will be considered to be given from some finite dimensional space H of functions defined in V. In other words, the function I(Q) itself will not be estimated but rather some finite dimensional approximation of the distribution I(Q).

Figure 27F:
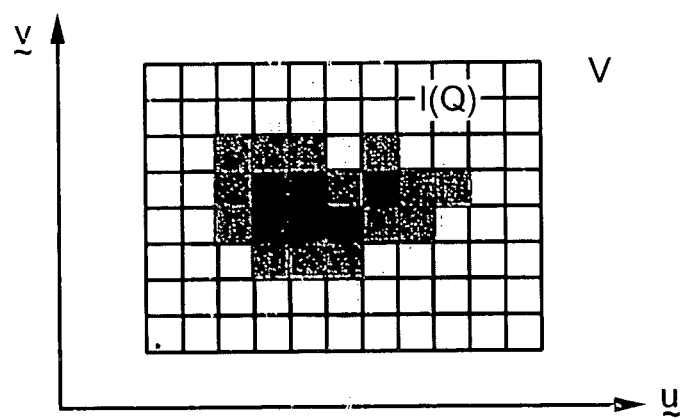

The simplest approach to finite dimensional approximation is to subdivide the rectangle V into sets of equal rectangular cells and consider the space H of step-functions corresponding to this subdivision (i.e., the space of functions that are constant in the cells of subdivision), as shown in FIG. 27F.

If the subdivision of rectangle V into small rectangles is sufficiently fine, then this step-function approximation is good enough for th estimation of radiation distribution I(Q).

Let each side of rectangle V be divided into n equal parts (FIG. 27F). Then $m=n^2$ is the dimension of the space H of step-functions on the corresponding subdivision.

The space H is naturally isomorphic to the m-dimensional space of n×n matrixes (with its natural scalar product $<\bullet,\bullet>$).

Let $I=(I_{i,j})_{i,j=1,\ldots,n}$ be the unknown element of H that it is desired to estimate. Suppose that element I is measured on K functionals $\{\Phi_k\}_{k=1\ldots K}$ of the form of the integral (1):

$$<I,\Phi_k>=\Sigma_{i,j=1\ldots n} I_{ij} \Phi_{ij}^{(k)} \quad (2)$$

where $\Phi_k = (\Phi_{ij}^{(k)})_{i,j=1,\ldots,n}$, $k=1,\ldots,K$ (after approximation of function I(Q), by the corresponding step-function, the integral (1) is transformed to the sum (2)).

Functionals $\Phi_k$, $k=1,\ldots,K$, correspond to K discrete positions of the sensor (FIG. 27E). Knowing the explicit expressions for functions $\square(r,z)$ from (1) and knowing for each time moment k, the position of the sensor relative to inspection region V, one can calculate all matrixes $\Phi_k = (\Phi_{ij}^{(k)})_{i,j=1,\ldots,n}$, $k=1,\ldots,K$.

Accordingly the following scheme of measurements are obtained:

$$\psi_k = <I,\Phi_k> + \epsilon_k, k=1,\ldots,K. \quad (3)$$

Here $\psi_k$ are results of measurements of the unknown element I of the space H, and $\epsilon_k$ are random errors ($\epsilon_k$—independent random variables, $E\epsilon_k=0$, $k=1,\ldots,K$).

Let M: H→H the operator in the space H of the form:

$$M=\Sigma_{k=1\ldots K} \Phi_k \otimes \Phi_k. \quad (4)$$

Then the best non-biased linear estimate $\hat{I}$ of the element I is given by the formula:

$$\hat{I}=M^{-1}\Psi, \quad (5)$$

where $M^{-1}$: H→H the inverse operator to the operator M of the form (4), and $$\Psi=\Sigma_{k=1\ldots K} \psi_k \Phi_k, \quad (6)$$

(where $\psi_k$ are the results of measurements of the form (3)).

One problem of using estimates (5) (besides computational problems if the dimension m of the space H is very large) is that the operator M: H→H of the form (3) is "bad invertible". In other words, the estimation problem is "ill-posed". It means that having a noise $\epsilon_k$ in the measurements scheme (3), even if the noise is small, may sometimes result in a very large estimation error dist(I, $\hat{I}$).

This means that the estimation problem requires additional regularization. This is a general problem of solving a large set of linear equations. There are several methods for solving such equations. Below is described one of the known methods for solving such equations but numerous other methods are also possible, theses include gradient decent methods such as in (http://www-visl.technion.ac.il/1999/99-03/www/) and other methods that are generally known in the art. Further, it is possible to improve the image reconstruction by taking into account the correlation between measurements as they are done with substantial overlap. Also, in the following description, a regular step function is assumed for the representation of the pixels or voxels, other basis may be used such as wavelet basis, Gaussian basis, etc., which may be better suited for some applications.

To obtain regularized estimate $\hat{I}_R$ instead of the estimate $\hat{I}$, the eigenvector decomposition of the operator M may be used:

Let $\phi_1, \phi_2, \ldots, \phi_m$ be eigenvectors of operator M: H→H corresponding to Eigenvalues $\lambda_1 \geq \lambda_2 \geq \ldots \geq \lambda_m \geq 0$.

Let R be some natural number, $1<R<m$ (R is the "regularization parameter"). Let $H^{(R)}$ be the subspace of the space H spanned by the first R eigenvectors $\phi_1, \ldots, \phi_R$.

$$H^{(R)} = sp\{\phi_k\}_{k=1\ldots R}. \quad (7)$$

Let $P^{(R)}$: H→$H^{(R)}$ be the orthogonal projection on subspace $H^{(R)}$.

The regularized estimate $\hat{I}_R$ may be obtained as follows:

Let $\Phi_k^{(R)} = P^{(R)} \Phi_k$, $k=1,\ldots,K$.

$$\Psi^{(R)} = \Sigma_{k=1\ldots K} \psi_k \Phi_k^{(R)}, \quad (8)$$

$M^{(R)}$: $H^{(R)} \to H^{(R)}$ the operator of the form:

$$M^{(R)} = \Sigma_{k=1\ldots K} \Phi_k^{(R)} \otimes \Phi_k^{(R)} \quad (9)$$

(operator $M^{(R)}$ is the restriction of the operator M of the form (4) to the subspace $H^{(R)}$ of the form (7)), then $\hat{I}^{(R)} = (M^{(R)})^{-1} \Psi^{(R)}$. \quad (10)

When the regularization parameter R is properly chosen (so that the eigenvalue $\lambda_R$ is not too small), then the estimate (10) becomes stable.

There are several possible approaches to choosing the parameter R. One approach is to leave R as a "program parameter" and to obtain the reasonable value "in experiment". Another approach is to choose some "optimal" value. This is possible if the covariation operators of the random noise $\delta_k$ in (3) are known, and information about the element I of the space H is known a priori.

The subdivision of rectangle V into a large number of equal rectangles has the disadvantage of making the dimension of the space H too big (especially in the 3D case). If each side of rectangle V is subdivided into n equal parts, then the dimension of the space H will be $n^2$ and the dimension of the matrices used in solving the corresponding estimation equations would be $n^2 \times n^2 = n^4$ (in the 3D case, $n^3 \times n^3 = n^6$). It is clear that for large n, this situation may cause serious memory and computation time.

In accordance with a preferred embodiment of the present invention, an irregular subdivision of the rectangle V is used. This irregular approach may significantly decrease the dimension of the problem and facilitate computer calculations.

More specifically, a drawback of the regular subdivision of the investigated region V, discussed hereinabove, is that a lot of cells that actually have no signal may be taken into account (FIG. 27F). It would be much better to have small cells only in regions with high signal and have big cells in regions with low signal.

Figure 27G:
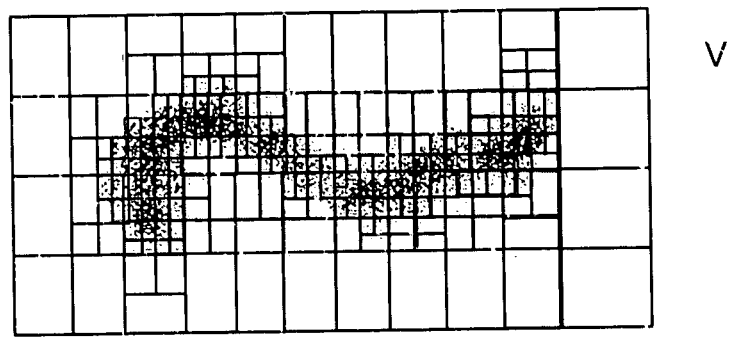

Reference is now made to FIG. 27G, which illustrates an advantageous irregular cell subdivision of rectangle V, in accordance with a preferred embodiment of the present invention.

In a first stage, regular subdivisions are made in "large" cells, and measurements and estimations are made as described hereinabove. In this manner, the intensity distribution is estimated in the large cells.

In a second stage, the large cells, which have an intensity larger than some threshold, are subdivided into 4 equal subcells (or 8 subcells in the 3D case). A suitable threshold may be obtained by taking the average intensity (of all large cells) minus two (or three) sigmas (standard deviation), for example. Measurements and estimations are made in these subdivisions as described hereinabove.

The act of subdivision and subsequent measurements and estimations are continued until a desired accuracy is reached at some smaller level of subdivision, typically defined by the computational and memory capabilities of the computer being used.

The 3D problem may be treated in the same way as the 2D case, the only difference being that instead of rectangle V, there is a parallelepiped V (FIG. 27D). Accordingly, the cells in each subdivision are also parallelepipeds.

In accordance with the present invention, the wide-aperture collimation—deconvolution algorithms described hereinabove may be used for a variety of imaging systems. For example, the algorithms may be used with single radiation detector probe, an array of radiation detector probes, large gamma cameras of various designs, such as multi-head cameras, general purpose cameras, and automatic white balance (AWB) scanners. The algorithms are suitable for SPECT and planar imaging, and may be used for all types of isotopes of with any type of photon energy.

From the foregoing discussion, the skilled artisan will appreciate that the algorithms described hereinabove may be used to predict the location of the radiation source and the uncertainty region (based on the system measurement errors) in the vicinity of the radiation source. The algorithms also guide the user to perform additional measurements to minimize the uncertainty region according to the requirements of the system operator.

The algorithms thus comprise a feedback system that employs analysis to determine the bounds of an uncertainty region about the radiation source, and which guides medical personnel to conduct additional scans in these uncertainty regions to improve accuracy, reduce error, and hence minimize the bounds of the uncertainty regions.

Continuous sampling with radiation probe 202 may provide localization of a tumor and a physiological radiation activity map of the tumor region. Higher safety and accuracy are gained by a greater number of scans.

Other deconvolution methods are known and are often used in image processing procedures. Examples of such deconvolution methods are described in U.S. Pat. No. 6,166,853 to Sapia et al., the disclosure of which is incorporated herein by reference. (However, it is appreciated that these are just examples and the present invention is not limited to the deconvolution methods mentioned in U.S. Pat. No. 6,166,853)

Figure 22:
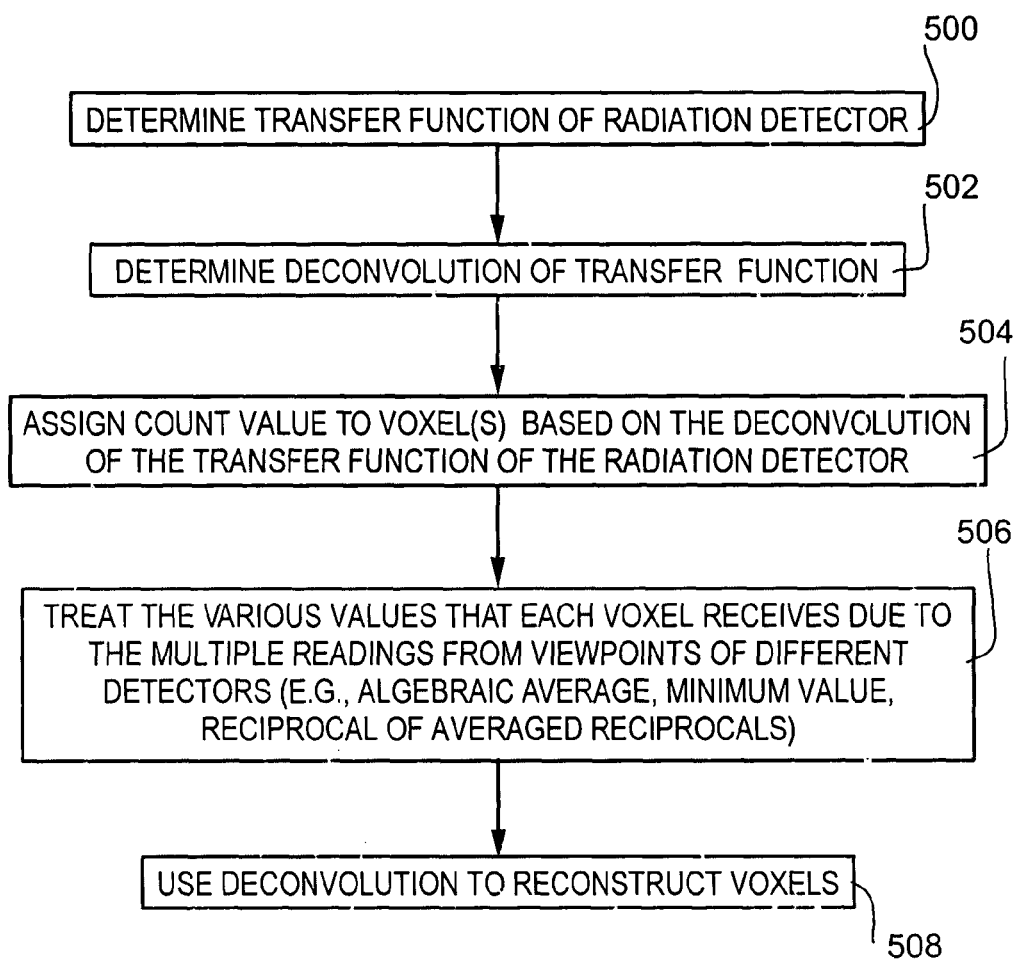
FIG. 22 is a simplified flow chart of a radiation map reconstruction algorithm, in accordance with a preferred embodiment of the present invention.

Reference is now made to FIG. 22 which illustrates a flow chart of a radiation map reconstruction algorithm, by another system of wide-aperture collimation—deconvolution algorithms, in accordance with another preferred embodiment of the present invention.

In typical image acquisition, light (or other electromagnetic wave energy) passes through a finite aperture to an image plane. The acquired image is a result of a convolution of the source object's light with the aperture of the imaging system. A system transfer-function may be generally obtained directly by taking the Fourier transform of the aperture. As is known in the art, the blurring effects due to convolution generally exist in two-dimensions only, i.e., the x-y planes. A point-spread-function (PSF) is an expression used to describe the convolutional blurring in two-imensions. The PSF physically results from imaging a point source. The Fourier transform of the PSF is the system transfer-function, which is obtained by convolving the system transfer-function with a Dirac-delta function. A point source is the physical equivalent of a Dirac-delta function, and, in the frequency domain, the Dirac-delta function is a unity operator across the spectrum. Therefore, the Fourier transform of the PSF should be the Fourier transform of the aperture. However, the PSF contains noise and blurring due to other effects such as aberrations.

The PSF contribution to the overall blurriness may be diminished or eliminated by deconvolution.

In the case of the present invention, the transfer function of the radiation detector may be determined by taking the Fourier transform of the aperture of the detector, and taking into account the noise and blurring due to other effects such as aberrations (step 500). An example of a transfer function may be a normal distribution. Using known mathematical techniques, the deconvolution of the transfer function may be determined (step 502).

The count readings of each spatial location of the detector constitute the sum of radiation counts from all the voxels (or pixels in the case of two-dimensional maps, the term "voxel" being used herein to include both pixels and voxels) within the detector's field of view. At least one voxel, or preferably each such voxel, may be assigned a count value based on the deconvolution of the unique transfer function of the radiation detector in use (step 504). An additional mathematical procedure may treat the various values that each voxel receives due to the multiple readings from viewpoints of different detectors (step 506). This treatment may constitute for example a simple algebraic average, minimum value or reciprocal of averaged reciprocals in order to produce a single value of readings in each voxel. The deconvolution is then used to reconstruct the voxels of the radiation map with diminished or no blurriness (step 508).

The algorithms described herein are applicable not only to the analysis of readings obtained using a directional radioactivity detector, rather they also apply for spatially sensitive (pixellated) radioactivity detectors. In this case, the readings of each pixel are algorithmically treated as described herein like for a directional radioactivity detector. The motivation behind using a spatially sensitive detector is to save on measurement time by receiving readings from a multitude of directions in parallel. This, in essence, creates a number of overlapping low resolution images which can then be processed to form a high resolution image. In addition, the spatially sensitive detector can be scanned to improve even further the resolution using the algorithms described hereinabove.

Thus, the same algorithms that apply for a directional detector apply for the spatially sensitive detector, only now instead of one radiation reading at each position, a large set of desecrate positions are processed in parallel. Each pixel can be seen as a separate detector with an angle of acceptance dictated by the geometry of a segmented collimator employed thereby. Each of the pixels occupies a different position in space and hence can be seen as a new position of a single directional probe by the algorithm described herein. It is also possible, like with the directional detector, to scan the whole set of pixels by scanning the spatially sensitive detector and to acquire a new set of data points from the new position. Once obtaining a low resolution image from each of the pixels of the spatially sensitive detector, a super resolution algorithm can be employed to generate an image of higher resolution. Suitable super resolution algorithms are described in, for example, J. Acoust Soc. Am., Vol. 77, No. 2, February 1985 Pages 567-572; Yokota and Sato, IEEE Trans. Acoust. Speech Signal Process. (April 1984); Yokota and Sato, Acoustical Imaging (Plenum, New York, 1982, Vol. 12; H. Shekarforoush and R. Chellappa, "Data-Driven Multi-channel Super-resolution with Application to Video Sequences", Journal of Optical Society of America-A, vol. 16, no. 3, pp. 481-492, 1999; H. Shekarforoush, J. Zerubia and M. Berthod, "Extension of Phase Correlation to Sub-pixel Registration", IEEE Trans. Image Processing, to appear, P. Cheeseman, R. Kanefsky, R. Kruft, J. Stutz, and R. Hanson, "Super-Resolved Surface Reconstruction From Multiple Images," NASA Technical Report FIA-94-12, December, 1994; A. M. Tekalp, M. K. Ozkan, and M. I. Sezan, "High-Resolution Image Reconstruction for Lower-Resolution Image Sequences and Space-Varying Image Restoration," IEEE International Conference on Acoustics, Speech, and Signal Processing (San Francisco, Calif.), pp. III-169-172, Mar. 23-26, 1992, http://www-visl.technion.ac.il/1999/99-03/www/. which are incorporated herein by reference.

Referring further to the drawings, FIGS. 28A-28F schematically illustrate a radioactive emission probe 700, preferably, handheld, for free-hand scanning, in accordance with preferred embodiments of the present invention.

As seen in FIG. 28A, handheld probe 700 is a lightweight nuclear imaging camera, adapted for free-hand movement and having a positioning device 714 incorporated thereto.

Handheld probe 700 includes a radiation detector 706, mounted onto a housing 702, wherein the various electronic components (not shown) are contained. Housing 702 is preferably formed of a rigid, lightweight plastic, a composite, or the like, and includes a handle 704, for easy maneuvering of probe 700.

A control unit 710, which may be mounted on housing 702, may include basic control knobs, such as "stop", "start", and "pause." Additionally or alternatively, control unit 710 may be a computer unit, such as a microcomputer or the like, having processing and memory units, contained within housing unit 702. Additionally, control unit 710 may include a display screen 718, mounted on housing unit 702, for displaying information such as gamma counts, gamma energies, device position, and the like. Display screen 718 may be interactive, for control and display. Control unit 710 may further include a data unit 720, for receiving a diskette, a minidisk, or the like. Preferably, data unit 720 is a read and write unit. An eject button 722 may be included with data unit 720.

A cable 724 may provide signal communication between handheld probe 700 and a main-data-collection-and-analysis-system 726, such as a PC computer or a server. Additionally or alternatively, signal communication with main-data-collection-and-analysis-system 726 may be wireless, for example, by radio frequency or infrared waves. Alternatively, hand-held probe 700 may be a stand-alone unit, operative with built-in computer unit 710. Additionally, data may be transferred to and from main-data-collection-and-analysis-system 726 via a diskette or a minidisk, from data unit 720.

A preferably rechargeable battery 716 may be attached to housing unit 702. Additionally or alternatively, a cable 712 may be used to provide power communication between handheld probe 700 and the grid (not shown), or between handheld probe 700 and main-data-collection-and-analysis-system 726.

Positioning device 714 is preferably a Navigation sensor, for determination of six coordinates X, Y and Z axes and rotational angles $\rho, \theta$ and $\phi$, as shown in FIG. 28F. Positioning device 714 may be mounted on housing 702, or located within it. Preferably, positioning device 714 is a magnetic tracking and location system, known as miniBIRD, commercially available from Ascension Technology Corporation, P.O. Box 527, Burlington, Vt. 05402 USA (http://www.ascension.tech.com/graphic.htm). Alternatively, any other known, preferably 6D tracking and positioning system may be used. Positioning device 714 maintains signal communication with either one or both of control unit 710 and main-data-collection-and-analysis-system 726.

As seen in FIGS. 28A and 28B, nuclear imaging detector 706 may be a disk, forming a single pixel, having a diameter D of about 10 mm, and a length L1 of about 5 mm. It will be appreciated that other dimensions, which may be larger or smaller, are also possible. Preferably, radiation detector 706 is connected to a preamplifier (not shown).

Additionally, as seen in FIGS. 28A and 28B, handheld probe 700 may include a tubular, wide-bore collimator 708, formed for example, of lead or of tungsten. The collimator may have a length L2 of about 10 to 30 mm, and preferably, about 15 mm. It will be appreciated that other dimensions, which may be larger or smaller, are also possible.

Alternatively, as seen in FIGS. 28C and 28D, collimator 708 may be a square grid of 4×4 cells 705, or 16×16 cells 705. Collimator grid 708 may have sides w of about 10 mm, and length L2 of about 20-40 mm. It will be appreciated that other dimensions, which may be larger or smaller, are also possible.

As seen in FIG. 28E, each cell 705 may include a plurality of radiation detector pixels 703, formed for example, as square pixels of 5×5 mm and length L1 also of about 5 mm. The reason for the division of nuclear detector 708 into pixels 703 is that while the wide aperture of a coarse collimator increases the counting efficiency, radiation detector uniformity is better maintained when the size of the radiation detectors is small. Thus, it is desired to combine a coarse collimator grid with a fine pixel size. Lead spacers are placed between the pixels. From spatial resolution consideration, each cell 705 preferably operates as a single pixel, but each pixel 703 within cell 705, must be calibrated individually, to correct for material nonuniformity, as will be described hereinbelow, in conjunction with FIG. 29B.

Preferably, radiation detector 706 is equipped with a positive contact array, for forming contact with each pixel 703, and a common negative contact. Preferably, each pixel 703 is connected to a preamplifier.

Preferably, radiation detector 706 is a single module array, for example, of 4×4, or of 16×16 pixels, of room temperature CdZnTe, obtained, for example, from IMARAD IMAGING SYSTEMS LTD., of Rehovot, ISRAEL, 76124, www.imarad.com.

Room temperature solid-state CdZnTe (CZT) is among the more promising nuclear detectors currently available. It has a better count-rate capability than other detectors on the market, and its pixilated structure provides intrinsic spatial resolution. Furthermore, because of the direct conversion of the gamma photon to charge-carriers, energy resolution is enhanced and there is better rejection of scatter events and improved contrast.

In accordance with the present invention, the detector may be optimized, in accordance with the teaching of "Electron lifetime determination in semiconductor gamma detector arrays," http://urila.tripod.com/hecht.htm, "GdTe and CdZnTe Crystal Growth and Production of Gamma Radiation Detectors," http://members.tripod.com/~urila/crystal.htm, and "Driving Energy Resolution to the Noise Limit in Semiconductor Gamma Detector Arrays," Poster presented at NSS2000 Conference, Lyon France, 15-20 Oct. 2000, http://urila.tripod.com/NSS.htm, all by Uri Lachish, of Guma Science, P.O.Box 2104, Rehovot 76120, Israel, urila@internet-zahav.net, all of whose disclosures are incorporated herein by reference.

Accordingly, radiation detector 706 may be a monolithic CdZnTe crystal, doped with a trivalent donor, such as indium. Alternatively, aluminum may be used as the trivalent donor. When a trivalent dopant, such as indium, replaces a bivalent cadmium atom within the crystal lattice, the extra electron falls into a deep trap, leaving behind an ionized shallow donor. The addition of more donors shifts the Fermi level from below the trapping band to somewhere within it. An optimal donor concentration is achieved when nearly all the deep traps become occupied and the Fermi level shifts to just above the deep trapping band.

Optimal spectral resolution may be achieved by adjusting the gamma charge collection time (i.e., the shape time) with respect to the electron transition time from contact to contact. Gamma photons are absorbed at different depth within the detector where they generate the electrons. As a result, these electrons travel a different distance to the counter electrode and therefore produce a different external signal for each gamma absorption event. By making the shape time shorter than the electron transition time, from contact to contact, these external signals become more or less equal leading to a dramatic improvement in resolution.

Furthermore, for a multi-pixel detector, the electrons move from the point of photon absorption towards the positive contact of a specific pixel. The holes, which are far slower, move towards the negative contact, and their signal contribution is distributed over a number of pixels. By adjusting the gamma charge collection time (i.e., the shape time) with respect to the electron transition time from contact to contact, the detector circuit collects only the electrons' contribution to the signal, and the spectral response is not deteriorated by the charge of the holes.

For an optimal detector, crystal electrical resistively may be, for example, about $5 \times 10^8$ ohm cm. The bias voltage may be, for example, −200 volts. The shape time may be, for example, $0.5 \times 10^{-6}$ sec. It will be appreciated that other values, which may be larger or smaller are also possible.

In accordance with a preferred embodiment of the present invention, control unit 710 includes data acquisition and control components, which further include a very small, single-module Detector Carrier Board (DCB). The DCB preferably includes a temperature control system, having a temperature sensor, a desired temperature setting, and a heat removal system, preferably operative by peltier cooling. Preferably, the DCB further includes a High Voltage (HV) power supply, a HV setting, a HV and dark current output-sensing, and power regulators, preferably having a range of about ±2V, a XAIM_MBAIS current driver, and noise filtering components.

Preferably, data acquisition and control components are based on Application Specific Integrated Circuit (ASIC) architecture for the control, calibration, and readout. ASIC data acquisition and control includes calibration of ASIC data, I/V conversion, amplification and shaping. Data identification includes threshold discrimination (i.e., noise rejection) and energy windows discrimination, wherein there may be one or several energy windows per radionuclide. Preferably, there are up to four energy windows per radionuclide, but it will be appreciated that another number is also possible.

Data acquisition relates to counting events per pixel, per energy window, for an acquisition period, which may be very short, for example, about 100 msec, in a continuous mode. It will be appreciated that larger or smaller counting periods are also possible.

The events per pixel 703, per energy window, is synchronized with signals from positioning device 714, preferably via a DIO card, either within control unit 710, or main-data collection-and-analysis-system 726, or both. Additionally, initialization information, including Digital to Analog Convertor (DAC) information, may be stored in software of main-data-collection-and-analysis-system 726 or within control system 710.

Preferably, an Integrated Drive Electronics (IDE) system provides the electronic interface.

Referring further to the drawings, FIGS. 29A-29B schematically illustrate the manner of calibrating handheld probe 700, in accordance with preferred embodiments of the present invention. Non-uniformity of the material leads to different sensitivities for each pixel. A correction is required to eliminate the sensitivity effect of the different pixels.

An energy spectrum for each pixel 703 of radiation detector 706 is obtained in a classical fashion. Radiation detector 706 is irradiated by a flood source of a known photon energy, for example, 24 KeV, and for each pixel 703, such as 703(1), 703(2), 703(3) ... 703(n), a summation of counts as a function of voltage is obtained, during a finite time interval. The location of the energy peak, corresponding to the peak photon energy, for example, 24 KeV is bounded, by an upper level (UL) and a lower level (LL) for that pixel 703(n), forming an energy window for the specific pixel. Only photons which fall within the bounded energy window for each pixel are counted, to exclude Compton scattering and pair production. A multi-energy source may be used, and several energy windows may be bounded for each pixel After the energy windows, representing specific energy peaks, are determined for each pixel, they are stored in a memory unit.

During acquisition, each collimator cell 705(n) is operative as a single pixel. Thus, the sensitivity correction factor has to be at a collimator-cell level, rather than at a pixel-level.

To calculate the sensitivity correction factor, an average counts per cell 705, is obtained as:

$$\text{average counts per cell } 705 = \frac{\text{sum of counts in all pixels 703 of detector 706}}{\text{number of collimator cells 705 in detector 706}}$$

$$\text{correction factor for cell } 705(n) = \frac{\text{average counts per cell 705}}{\text{counts in a cell 705(n)}}$$

During acquisition, the sum of counts within the bounded windows of all pixels in cell 705(n) is multiplied by the correction factor for that cell 705(n) to obtain a sensitivity corrected count rate.

Figure 30:
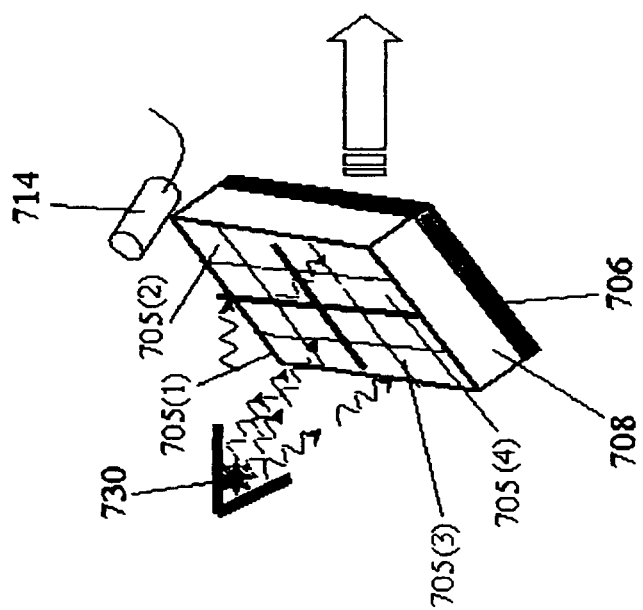
FIG. 30. schematically illustrates the manner of synchronizing event and position readings of the handheld probe of FIGS. 28A-28F, in accordance with a preferred embodiment of the present invention.

Referring further to the drawings, FIG. 30 schematically illustrates the manner of synchronizing event readings by radiation detector 706 and position readings by positioning device 714, in accordance with preferred embodiments of the present invention. Preferably, event readings, for each cell 705 is tabulated with the position reading, for each lime interval, such as $t_1$, $t_2$, $t_3$, after correction for sensitivity.

Figure 31A:
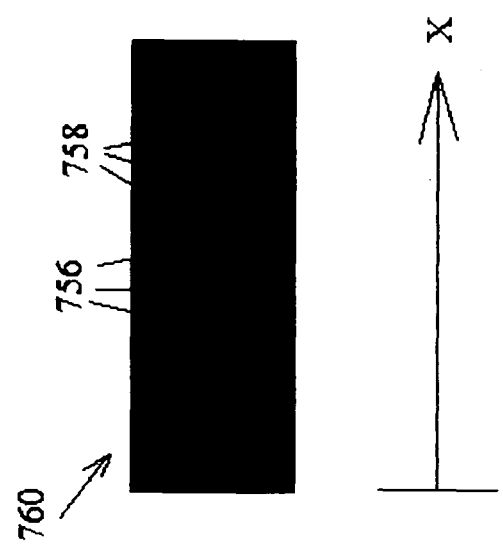
FIGS. 31A-31C describe a spatial resolution bar-phantom test of a radioactive emission probe, in accordance with a preferred embodiment of the present invention.
Figure 31B:
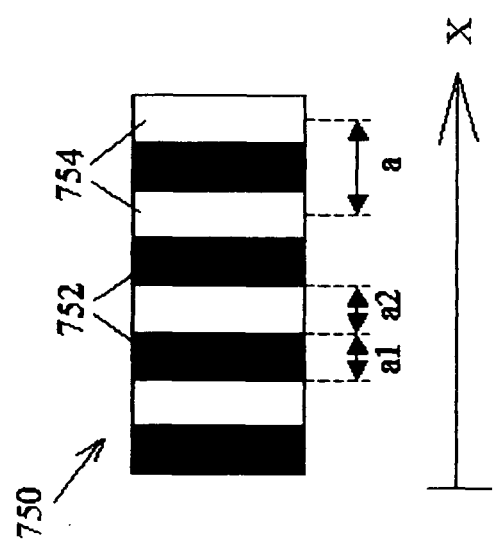
Figure 31C:
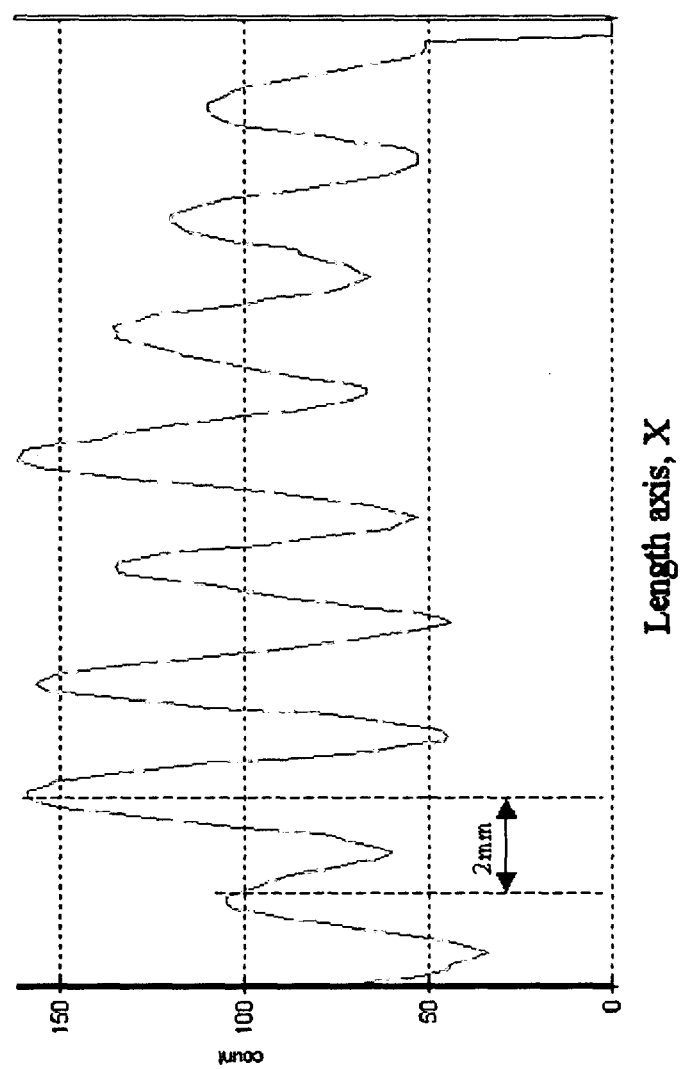
Figure 32A:
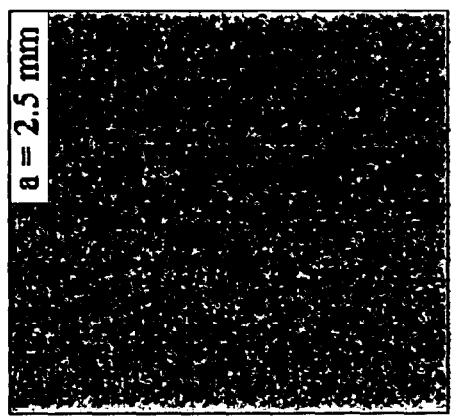
FIGS. 32A-32D describe a spatial resolution bar-phantom test of a prior-art probe.
Figure 32B:
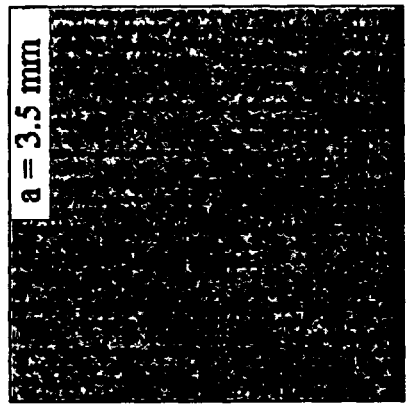
Figure 32C:
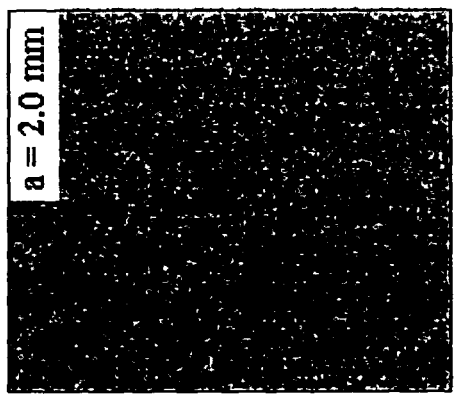
Figure 32D:
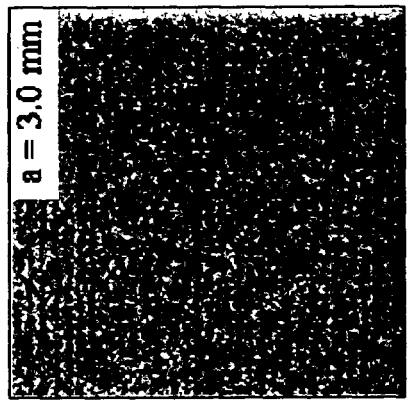

Referring further to the drawings, FIGS. 31A-31C describe a spatial resolution bar-phantom test of probe 700, in accordance with a preferred embodiment of the present invention. As in FIGS. 17 and 18, hereinabove, the aim of the bar phantom test is to evaluate image quality by measuring image resolution of a bar phantom. Spatial resolution is expressed in terms of the finest bar pattern, visible on nuclear images.

As seen in FIG. 31A, a bar phantom 750 was constructed of lead strips 752, encased in a plastic holder (not shown). The lead strips were of equal width and spacing. Thus, a 2-mm bar pattern consisted of 2-mm wide strips 752, separated by 2-mm spaces 754, along an x axis. The thickness of lead strips 752 was, sufficient to ensure that bars 752 are virtually opaque to the γ rays being imaged.

A uniform radiation field, formed of a sheet source (not shown), was placed directly behind the bar phantom 750, and bar phantom 750 was scanned with probe 700.

Probe 700 of the present embodiment comprised an eV Pen-type CdZnTe solid state detector with collimator diameter D, of 5 mm, and collimator length, L2 of 30 mm. The CdZnTe detector was attached to a charge sensitive preamp probe and connected to a Digital and analog V-target alpha system PC cards. The probe energy window calibration was performed at the beginning of the test by using EG&G Ortec Maestro 2K Tramp ISA Spectra Processing connected to the analog and the digital V-target alpha system cards. The probe position information was provided by MicroScribe-6DLX arm manufactured by Immersion Corporation. Acquisition time was 6 minutes.

FIG. 31B illustrates a bar phantom image 760, produced by probe 700, after 6 minutes of acquisition time, in accordance with the present invention. Image 760 shows bar images 756, and space images 758, of the 2-mm bar pattern, clearly demonstrating a high degree of spatial resolution.

FIG. 31C provides a similar observation, based counts as a function of length axis, X. The well-defined, narrow sinusoidal peaks of counts as a function of length axis demonstrate a high degree of spatial resolution for the 2-mm bar pattern.

Referring further to the drawings, FIGS. 32A-32D describe a spatial resolution bar-phantom test of a prior-art probe, a High Resolution Gamma Camera of a competitor. Although for the prior art probe, acquisition time was 3 hours, a bar pattern is barely observed for a 3-mm bar pattern of FIG. 32C, and clearly observed only for a 3.5 mm bar pattern of FIG. 32D. Table 1 provides a comparison with a prior art technology.

TABLE 1

| Imaging Technology | Detector-collimator arrangement | Acquisition Time | Maximum Spatial Resolution |
|---|---|---|---|
| a High-resolution Gamma-Camera of a competitor's | multi-pixel detector, tube collimators 1.9 mm in dia. 40 mm in length | 180 min. | Worse then 3 mm |
| Probe 700 of FIG. 28A | single-pixel detector 10 mm in dia. tube collimator 25 mm in length | 6 min. | 2 mm |
| Summary | | V-target probe is 30 time faster | V-target's resolution is 2 time better |

As seen in Table 1, there is a clear advantage to the probe of the present invention.

Good energy resolution of the detector is important for precise identification and separation of γ rays, for radionuclide identification and for scatter rejection. A major advantage of CdZnTe detector is better energy resolution, for example than that of the NaI(Tl) detector.

Figure 33A:
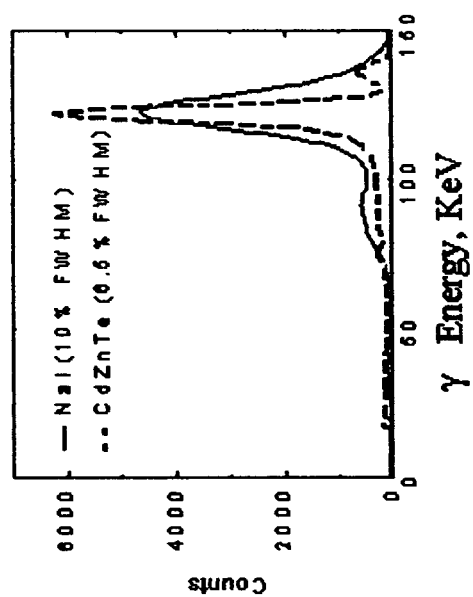
FIGS. 33A-33B illustrate the energy resolution of a single pixel of a radioactive emission probe, in accordance with the present invention.
Figure 33B:
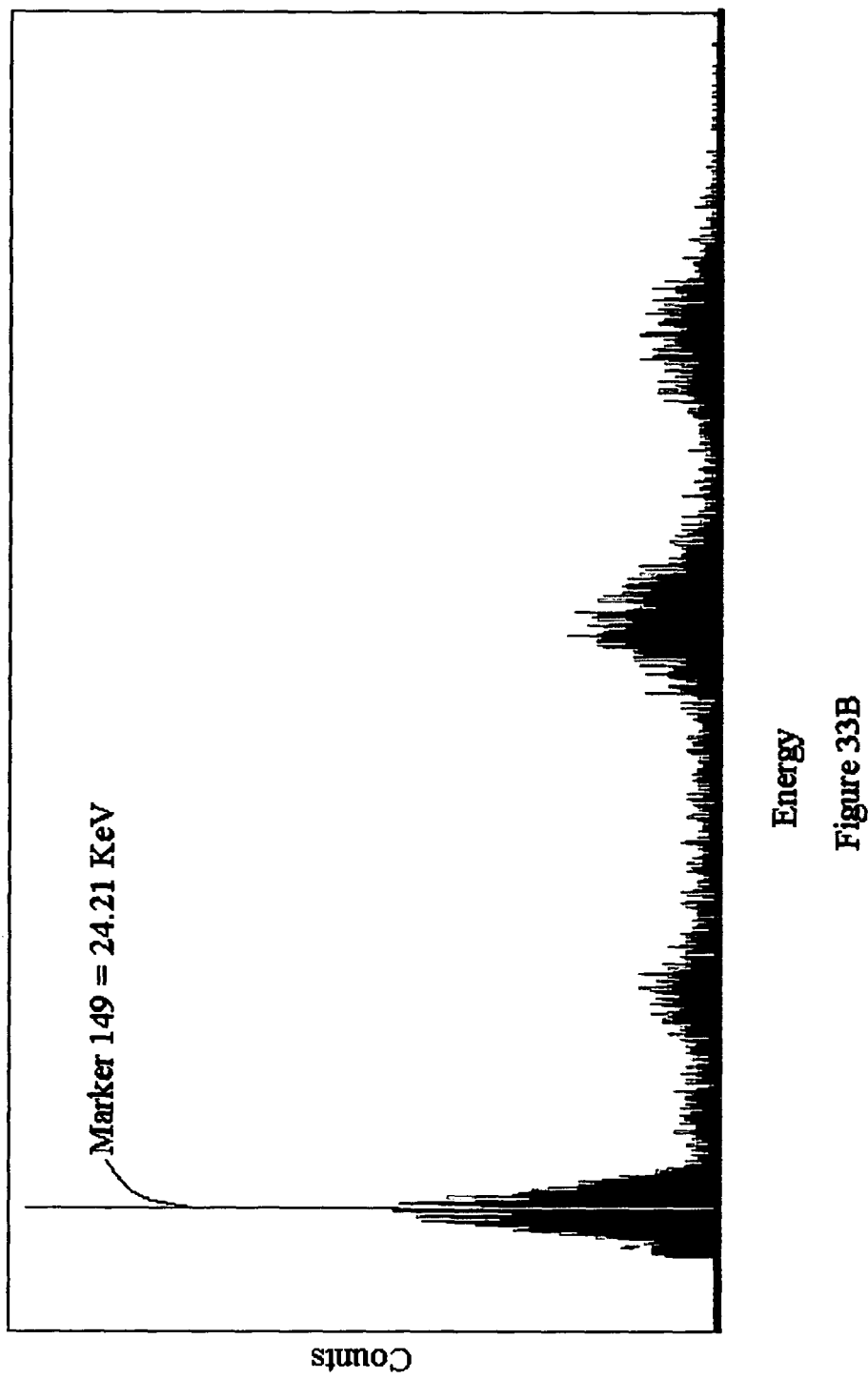

Referring further to the drawings, FIGS. 33A-33B illustrate the energy resolution of a single pixel 703 of probe 700, in accordance with the present invention.

FIG. 33A compares a spectrum of a single pixel of a CdZnTe detector with that obtained by a single pixel of an NaI(Tl) detector, at ~120 KeV, showing the difference in energy resolution between the two detectors. Clearly, the a CdZnTe detector provides a sharper, more well-defined energy peak, which is about ⅓ higher than the NaI(Tl) peak, and having a FWHM that is ⅔ that of the NaI(Tl) peak.

FIG. 33B provides a spectrum of a CdZnTe detector, showing good energy resolution at the low energy level of about 24 KeV.

Figure 34A:
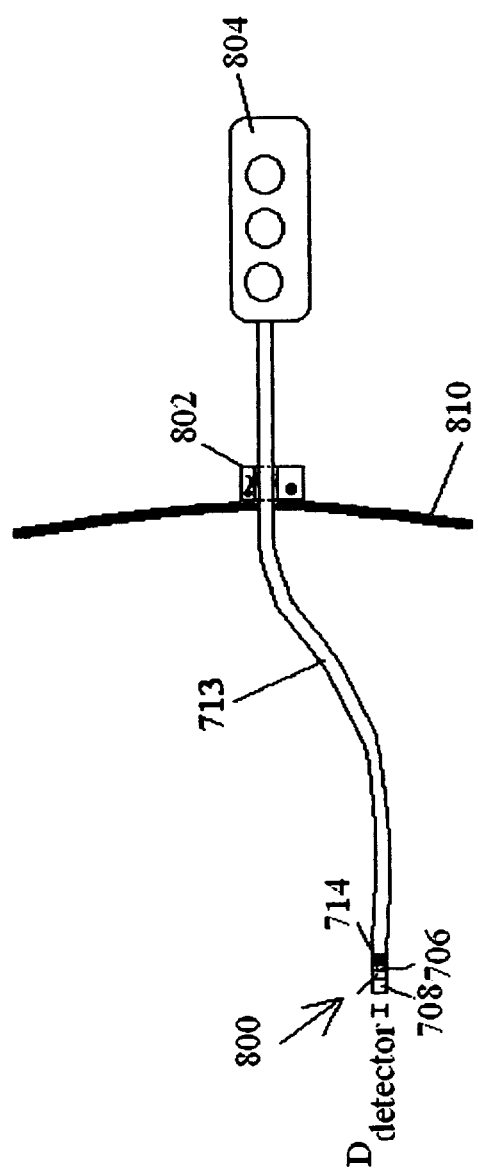

Referring further to the drawings, FIGS. 34A-34C schematically illustrate endoscopic radioactive emission probes 800, adapted to be inserted into the body, on a shaft or a catheter 713, via a trocar valve 802 in a tissue 810.

As seen in FIG. 34A, endoscopic radioactive emission probe 800 may include, for example, radiation detector 706, for example, of a single pixel, wide-bore collimator 708, position tracking system 714, and an extracorporeal control unit 804. Preferably, the diameter of radiation detector 706, $D_{detector}$, is less than 12 mm. In accordance with another embodiment of the present invention, radioactive emission probe 800 may be used in body lumens, for example, for scanning the stomach or the uterus.

As seen in FIG. 34B, endoscopic radioactive emission probe 800 may include several radiation detectors 706, for example, of a single pixel each, and having a dedicated collimator 708, each. Unlike the collimator grid structure of FIGS. 28C and 28D, the collimators of FIG. 34B are not parallel to each other, and each may point in a different direction. Alternatively, each radiation detector 706 may include a plurality of pixels.

As seen in FIG. 34C, endoscopic radioactive emission probe 800 may include several radiation detectors 706, which may include wide-angle collimators.

Figure 35:
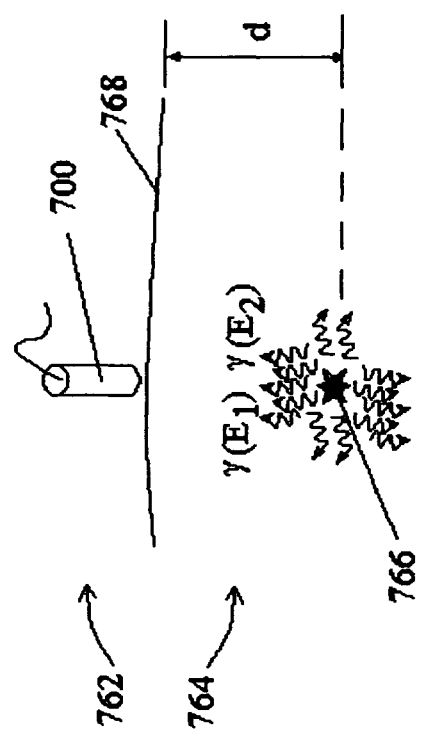
FIG. 35 illustrate a method of calculating the depth of a radiation source, in accordance with the present invention.

Referring further to the drawings, FIG. 35 schematically illustrates a manner of calculating a distance, d, between radioactive emission probe, such as probe 700 (FIGS. 28A-28F) and a radiation source 766, based on the attenuation of photons of different energies, which are emitted from the same source. Probe 700 is on an extracorporeal side 762 and radiation source 766 is on an intracorporeal side 764 of a tissue 768.

The transmitted intensity of a monochromatic gamma-ray bean of photon energy F, and intensity $I_0$ crossing an absorbing layer, such as a tissue layer, of a depth d, is a function of the photons energy E, the layer thickness d, and the total linear attenuation coefficient as a function of energy, $\mu_{total}$, of the material constituting the layer. The transmitted intensity is given by:

$$I(E)=I_0(E)\exp(-\mu_{total}(E)d) \quad \text{(Eq-1)}$$

The linear attenuation coefficient is expressed in $cm^{-1}$ and is obtained by multiplying the cross section (in $cm^2/gr$) with the absorbing medium density. The total linear attenuation coefficient accounts for absorption due to all the relevant interaction mechanisms: photoelectric effect, Compton scattering, and pair production.

The layer thickness d, which is the depth of the radiation source, can be measured using a radionuclide that emits two or more photon energies, since attenuation is a function of the photon energy.

For photons of different energies, originating from a same source, and having the same half-life, we get:

$$\frac{I(E_1)}{I(E_2)} = \frac{I_0(E_1)}{I_0(E_2)} \cdot \frac{e^{-\mu(E_1)\cdot d}}{e^{-\mu(E_2)\cdot d}} \quad \text{(Eq-2)}$$

$$A = \frac{I(E_1)}{I(E_2)} \,\&\, B = \frac{I_0(E_1)}{I_0(E_2)} \quad \text{(Eq-3)}$$

$$R = \frac{A}{B} = \frac{[I(E_1)/I(E_2)]}{[I_0(E_1)/I_0(E_2)]} \quad \text{(Eq-4)}$$

$$A = B \cdot \frac{e^{-\mu(E_1)\cdot d}}{e^{-\mu(E_2)\cdot d}} \Rightarrow R = \frac{e^{-\mu(E_1)\cdot d}}{e^{-\mu(E_2)\cdot d}} \quad \text{(Eq-5)}$$

$$R = e^{\{\mu(E_2)-\mu(E_1)\}d} \Rightarrow \ln(R) = \{\mu(E_2)-\mu(E_1)\}d \quad \text{(Eq-6)}$$

The source depth, d, can be calculated as:

$$d = \frac{\ln(R)}{\mu(E_2)-\mu(E_1)} = \frac{\ln\{[I(E_1)/I(E_2)]/[I_0(E_1)/I_0(E_2)]\}}{\mu(E_2)-\mu(E_1)} \quad \text{(Eq-7)}$$

The linear attenuation coefficients for specific energies are calculated from the photon mass attenuation and energy absorption coefficients table.

The ratio $I_0(E_1)/I_0(E_2)$ for a known isotope or isotopes is calculated from an isotope table and the ratio $I(E_1)/I(E_2)$ is measured at the inspected object edges.

Additionally, X-ray information, for example, mammography may be used, for more material linear attenuation coefficient, since X-ray imaging provides information about the material density.

For example, we may consider a lesion inside a soft tissue, such as a breast, at a distance d that holds an isotope of $^{123}$I, which emits two main photons, as follows:

$E_1$=27 keV with 86.5%; and
$E_2$=159 keV with 83.4%.

The soft tissue density is 0.8 g/cu³.

The linear attenuation coefficients for $E_1$ and $E_2$ are calculated from J. H Hubbell, "Photon Mass Attenuation and Energy—absorption Coefficients from 1 keV to 20 MeV", Int. J. Appl. Radiat. Isat. Vol. 33. pp. 1269 to 1290, 1982, as follows:

$\mu(E_1)$=0.474 cm/g→$\mu(E_1)$=0.474 cm/g·0.8 g/cm³=0.38 1/cm $\mu(E_2)$=0.1489 cm/g→$\mu(E_2)$=0.1489 cm/g·0.8 g/cm³=0.119 1/cm

The measured ratio between $I(E_1)$ to $I(E_2)$ on the attenuating soft tissue edge is 0.6153.

Using Eq-7, one gets that the lesion depth is: d=2 cm.

Alternatively, if the measured ration between $I(E_1)$ to $I(E_2)$ is 0.473 the extracted lesion depth is: d=3 cm.

It will be appreciated that when two or more isotopes used for obtaining the different photons, corrections for their respective half-lives may be required.

It will be appreciated that by calculating the depth of a radiation source at each position, one may obtain a radiation source depth map, in effect, a three-dimensional image of the radiation source. This information may be superimposed on the radiation source image, as produced by other methods of the present invention, as an independent check of the other methods. For example, a radiation source image produced by the wide-aperture collimation—deconvolution algorithms may be superimposed on a radiation source image produced by depth calculations of based on the attenuation of photons of different energies.

EXPERIMENTAL RESULTS

Figure 23B:
FIGS. 23A and 23B are illustrations of radiolabeled patterns observed in images produced by the system of the invention and by a conventional gamma camera, respectively, of an autonomous adenoma of a thyroid.
Figure 23A:

In a series of clinical experiments, some of the basic concepts of the invention have been tested on patients who were pre-injected with a suitable radiopharmaceutical for their particular pathology. Two-dimensional color-coded maps have been constructed based on a scan of a pre-determined lesion area by a hand-held radiation detector with a magnetic position-tracking system. The resulting maps, which represented the radiation count level, were compared to images of conventional gamma camera. The list of radiopharmaceuticals tested includes $^{18}$FDG, $^{99M}$Tc-MDP, $^{99M}$Tc sodium pertechnetate, $^{99M}$Tc erythrocytes. Similar radiolabeled patterns were observed in the images produced by the system of the invention and in the images produced by a conventional gamma camera in the following pathologies:

FIGS. 23A and 23B illustrate radiolabeled patterns observed in images produced by the system of the invention and by a conventional gamma camera, respectively, of an autonomous adenoma of a thyroid of a 58 year-old male.

Figure 24B:
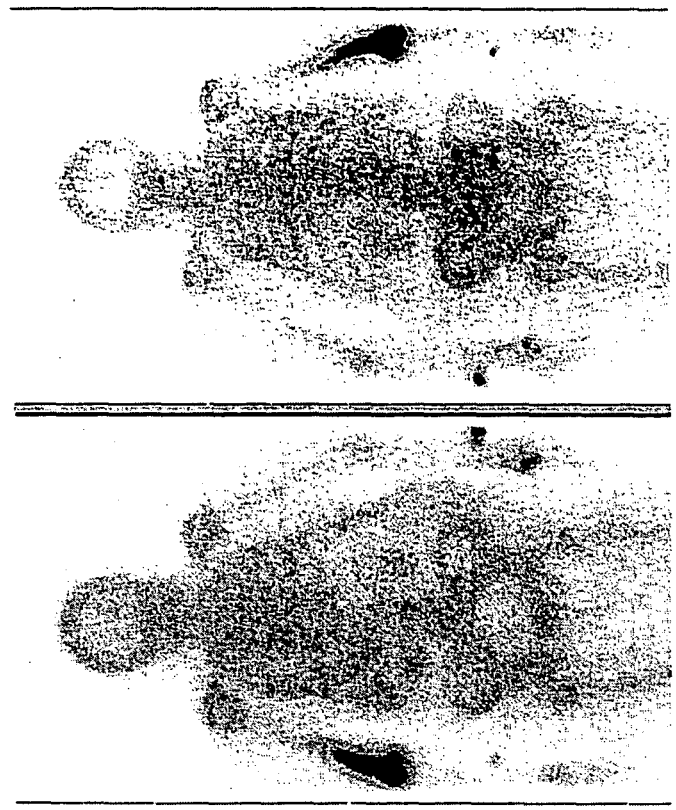
FIGS. 24A and 24B are illustrations of radiolabeled patterns observed in images produced by the system of the invention and by a conventional gamma camera, respectively, of suspected Paget's disease of a humerus.
Figure 24A:

FIGS. 24A and 24B illustrate radiolabeled patterns observed in images produced by the system of the invention and by a conventional gamma camera, respectively, of suspected Paget's disease of a humerus in an 89 year-old female.

Figure 25B:
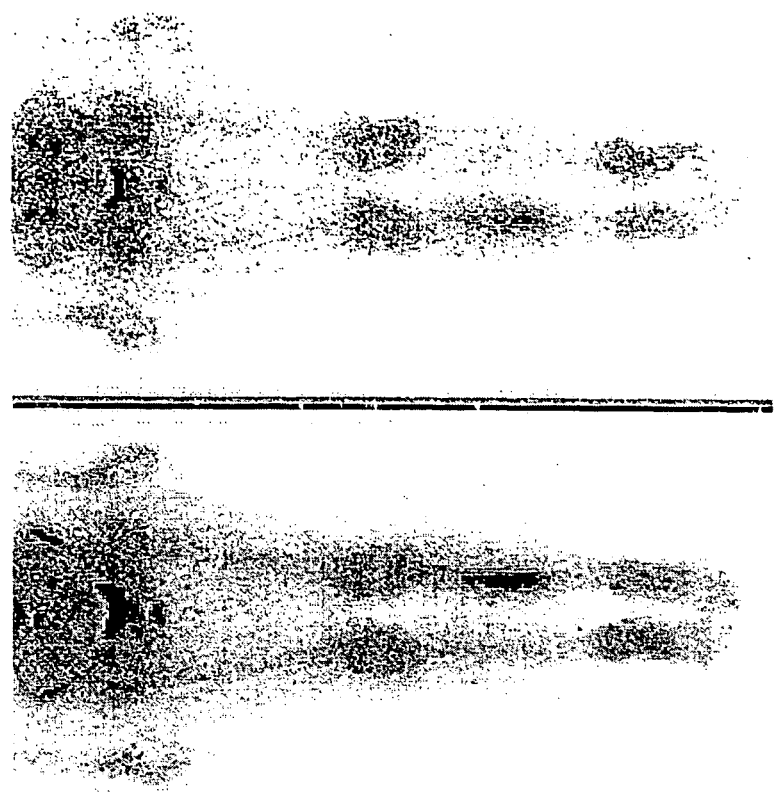
FIGS. 25A and 25B are illustrations of radiolabeled patterns observed in images produced by the system of the invention and by a conventional gamma camera, respectively, of chronic osteomyelitis.
Figure 25A:
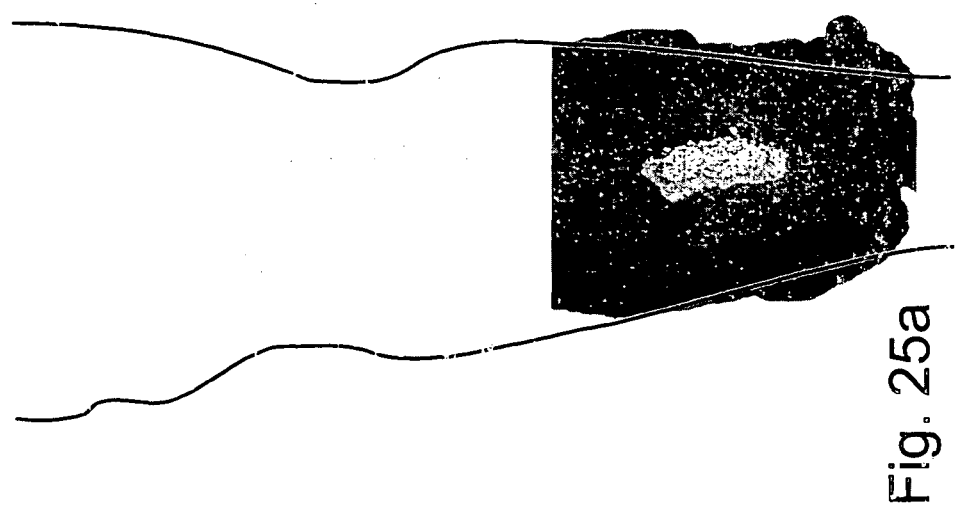

FIGS. 25A and 25B illustrate radiolabeled patterns observed in images produced by the system of the invention and by a conventional gamma camera, respectively, of chronic osteomyelitis in a 19 year-old female.

FIGS. 26A and 26B illustrate radiolabeled patterns observed in images produced by the system of the invention and by a conventional gamma camera, respectively, of skeletal metastasis from medulloblastoma in an 18 year-old male.

Figure 36:
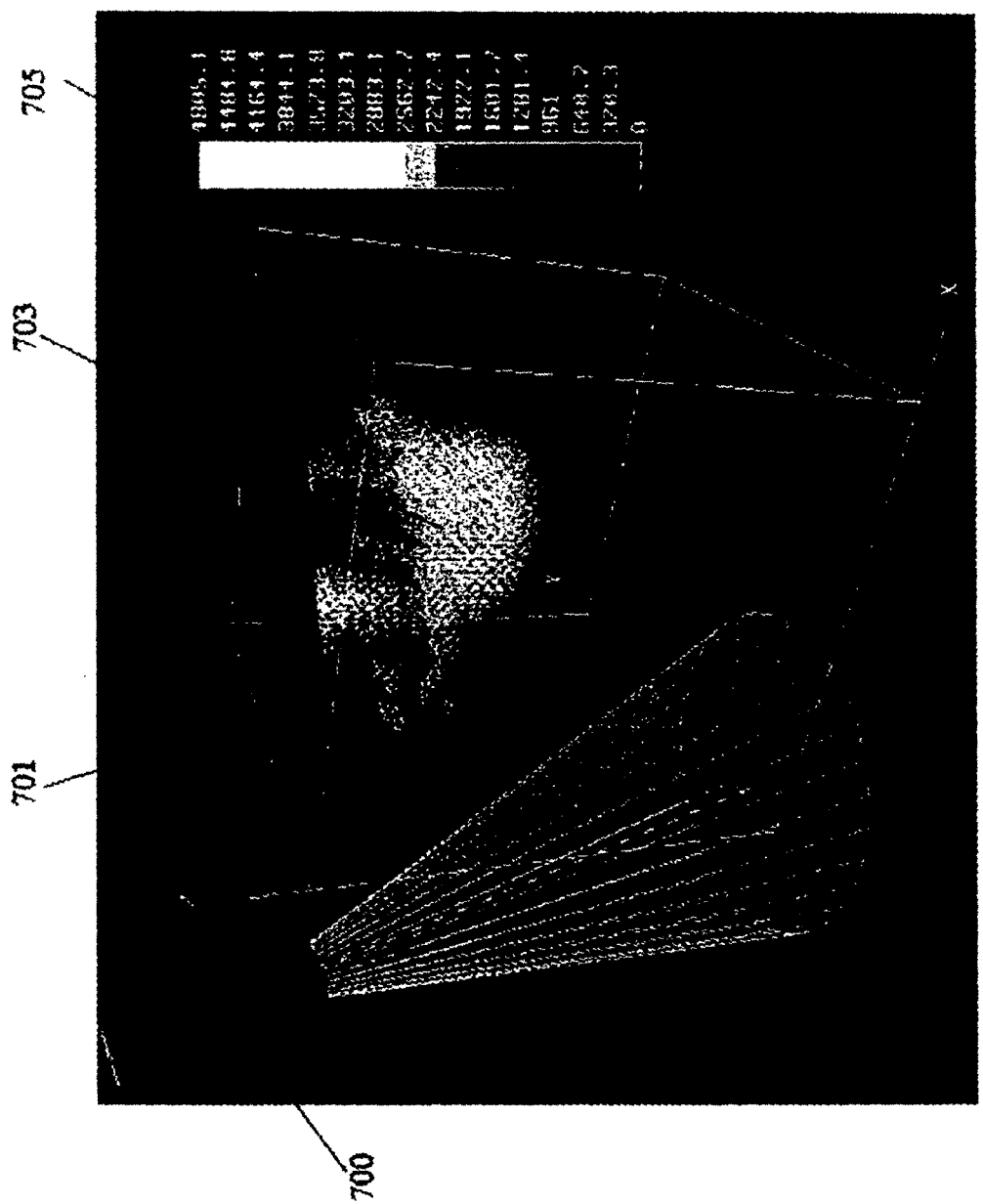
FIG. 36 illustrate a two-dimensional image of the radioactivity emitting source, produced by a free-hand scanning of a cancerous prostate gland, ex vivo, in accordance with the present invention.

FIG. 36 illustrates a control volume 701, and a three-dimensional image 703 of the radioactivity emitting source, produced by a free-hand scanning of a cancerous prostate gland, ex vivo, with hand-held probe 700 of FIG. 28A. The diameter of the detector was 10 mm, and the length of the collimator was 25 mm. The wide-aperture collimation—deconvoluting algorithm was used, for image reconstruction. A scale 705 illustrates brightness as a function of count rate density. The brighter the area, the higher the count density. The Figure shows the capability of hand-held probe 700 to detect cancerous tissue. The By comparison, the competitor's High-resolution, Gamma-Camera failed to detect any cancerous growth.

The following provides a list of known procedures which can take advantage of the system and method of the present invention:

In cancer diagnosis the syste m and method of the present invention can find uses for screening for cancer and (or) directing invasive diagnosis (biopsies) either from outside the body or by way of endoscopic approach. Examples include, but are not limited to, lung cancer biopsy, breast cancer biopsy, prostate cancer biopsy, cervical cancer biopsy, liver cancer biopsy, lymph node cancer biopsy, thyroid cancer biopsy, brain cancer biopsy, bone cancer biopsy, colon cancer biopsy, gastro intestine cancer endoscopy and biopsy, endoscopic screening for vaginal cancer, endoscopic screening for prostate cancer (by way of the rectum), endoscopic screening for ovarian cancer (by way of the vagina), endoscopic screening for cervical cancer (by way of the vagina), endoscopic screening for bladder cancer (by way of the urinary track), endoscopic screening for bile cancer (by way of the gastrointestinal track), screening for lung cancer, screening for breast cancer, screening for melanoma, screening for brain cancer, screening for lymph cancer, screening for kidney cancer, screening for gastro intestinal cancer (from the outside).

In the special case of MRI, the radiation detector can be combined and packaged together with a small RF coil for the transmission and reception or reception only of the MRI signals in a rectal probe configuration for prostate diagnosis and treatment or any other close confinement position such as the vagina, airways, the uper portion of the gastrointestinal track, etc)

Procedures known as directing localized treatment of cancer can also benefit from the system and method of the present invention. Examples include, but are not limited to, intra tumoral chemotherapy, intra tumoral brachytherapy, intra tumoral cryogenic ablation, intra tumoral radio frequency ablation, intra tumoral ultrasound ablation, and intra tumoral laser ablation, in cases of, for example, lung cancer, breast cancer, prostate cancer, cervical cancer, liver cancer, lymph cancer, thyroid cancer, brain cancer, bone cancer, colon cancer (by way of endoscopy through the rectum), gastric cancer (by way of endoscopy through the thorax), thoracic cancer, small intestine cancer (by way of endoscopy through the rectum or, by way of endoscopy through the thorax), bladder cancer, kidney cancer, vaginal cancer and ovarian cancer.

In interventional cardiology the following procedures can take advantage of the present invention wherein the method and system can be used to assess tissue perfusion, tissue viability and blood flow intra operatively during PTCA procedure (balloon alone or in conjunction with the placement of a stent), in cases of cardiogenic shock to assess damage to the heart, following myocardial infarct to asses damage to the heart, in assessing heart failure condition tissue in terms of tissue viability and tissue perfusion, in intra vascular tissue viability and perfusion assessment prior to CABG operation.

The radioactivity detector can be mounted on a catheter that is entered through the blood vessels to the heart to evaluate ischemia from within the heart in order to guide ablation probes or another type of treatment to the appropriate location within the heart. Another application which may benefit from the present invention is the localization of blood clots. For example, a radioactivity detector as described herein can be used to assess and differentiate between new clots and old clots. Thus, for example, the radioactivity detector can be placed on a very small caliber wire such as a guide wire that is used during PTCA in order to image blood-vessel clots. Blood-vessel clots can be searched for in the aortic arc as clots therein are responsible for about 75% of stroke cases.

Using the method and system of the present invention to assess tissue perfusion, tissue viability and blood flow intra operatively can also be employed in the following: during CABG operation to asses tissue viability, to mark infarct areas, during CABG operations to asses the success of the re vascularization.

The present invention has many other applications in the direction of therapeutics, such as, but not limited to, implanting brachytherapy seeds, ultrasound microwave radio-frequency cryotherapy and localized radiation ablations.

It will be appreciated that many other procedures may also take advantage of the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications in printed or electronic form, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of obtaining an image of a radioactivity emitting source in a patient's body comprising:
    scanning the radioactivity emitting source with a probe comprising at least one collimator defining a first angle from which the probe detects radiation events to obtain image data at a first resolution or less;
    monitoring one or more positions of said radioactive emission probe in different planes around said radioactivity emitting source;
    data processing said image data at a first resolution and said one or more positions, wherein said data processing comprises correcting blurring effects related to the direction from which radiation events are detected with the at least one collimator thereby generating similarity to detecting radiation events using a collimator with a second angle narrower than said first angle, said second angle obtaining image data at a second resolution, higher than said first resolution; and
    forming a three-dimensional model of said radioactivity emitting source by said data processing, wherein said three-dimensional model is in said second resolution.

2. The method of claim 1, wherein said image resolution comprises spatial resolution.

3. The method of claim 1, wherein said scanning and said monitoring are performed approximately at the same time.

4. The method of claim 1, wherein said monitoring comprises monitoring said one or more position at time intervals that are fine enough to obtain said similarity to detecting radiation events at a second angle narrower than said first angle, said second angle obtaining image data at a second resolution, higher than said first resolution.

5. The method of claim 4, wherein said time intervals comprise between 100-200 ms.

6. The method of claim 1, wherein said data processing comprises using a collimation—deconvolution algorithm to obtain said image data at a second resolution.

7. The method of claim 6, wherein said collimation—deconvolution algorithm is based on account estimation of a transfer function.

8. The method of claim 1, wherein said data processing comprises calculating a value of readings for each voxel based on multiple readings from view points of said probe; and using a collimation—deconvolution algorithm to reconstruct voxels of the radiation map with diminished or no blurriness.

9. A method of obtaining a high resolution image of a radioactivity emitting source in a patient's body comprising:

scanning a radioactive source from a multitude of different directions and/or distances using a radioactive probe comprising one or more collimators, each defining a collimation angle from which the probe detects radiation events so that fields of view from one or more of said collimation angles overlap, to acquire image data at a first resolution or less;

monitoring a position and orientation of said one or more collimators during said scanning; and forming a three-dimensional image of the radioactive source at a second resolution by data processing said image data at a first resolution and said monitored position and orientation to form images at said second resolution, wherein said second resolution is higher than said first resolution.

10. The method of claim 9, further comprising repeating said scanning from a new position to acquire a new set of data points from said new position and improving the resolution of said second resolution images based on said new position and new set of data points.

11. The method of claim 9, wherein said scanning comprises receiving readings from a multitude of directions in parallel.

12. The method of claim 9, wherein said forming comprises using a super resolution algorithm to generate said second resolution image from said first resolution image.

13. The method of claim 9, wherein said first resolution image comprises an image from each pixel of a spatially sensitive detector.

14. The method of claim 9, further comprising integrating data pertaining to a body portion as retrieved by said method and non-radioactive imaging to isolate the portion of the body emitting said radiation.

15. The method of claim 9, wherein said scanning comprises scanning in three dimensions.

16. The method of claim 9, wherein said scanning comprises scanning intracorporeally and extracorporeally in concert to increase the precision of determining the position of said radioactivity emitting source inside a body.

17. The method of claim 9, wherein said second resolution images have at least the equivalence of detection from an angle narrower than said collimation angle.

18. The method of claim 17, wherein at least one of said collimators has a ratio of length to diameter of between 1-3.

19. The method of claim 9, wherein said radioactive probe comprises a plurality of single pixel detector units configured to generate said low resolution image data from each of said pixels.

20. The method of claim 9, wherein said data processing comprises improving image resolution by an image acquisition and reconstruction algorithm, based on collimation—deconvolution algorithms.

21. The method of claim 9, wherein said radioactive probe comprises a plurality of radiation detectors.

22. The method of claim 9, wherein said radioactive probe is an intracorporeal radioactive emission probe mounted on a surgical instrument.

23. The method of claim 9, wherein said monitoring comprises tracking said probe at time intervals short enough to increase accuracy of construction of said second resolution images.

24. The method of claim 23, wherein said time interval comprises between 100 and 200 milliseconds.

25. The method of claim 9, wherein said radioactive probe is configured for variable course motion.

26. The method of claim 9, wherein said collimation angle comprises between 80 to 280 degrees.

27. The method of claim 9, wherein said radioactive source comprises an x-ray source.

28. The method of claim 9, wherein said radioactive source comprises a single photon emission of an isotope.

29. The method of claim 9, wherein said radioactive source comprises a positron emission.

* * * * *